(12) United States Patent
Hildebrand et al.

(10) Patent No.: US 7,541,429 B2
(45) Date of Patent: Jun. 2, 2009

(54) COMPARATIVE LIGAND MAPPING FROM MHC POSITIVE CELLS

(75) Inventors: William H. Hildebrand, Edmond, OK (US); Heather D. Hickman, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 224 days.

(21) Appl. No.: 09/974,366

(22) Filed: Oct. 10, 2001

(65) Prior Publication Data

US 2002/0197672 A1 Dec. 26, 2002

Related U.S. Application Data

(60) Provisional application No. 60/240,143, filed on Oct. 10, 2000, provisional application No. 60/299,452, filed on Jun. 20, 2001, provisional application No. 60/256,410, filed on Dec. 18, 2000, provisional application No. 60/256,409, filed on Dec. 18, 2000.

(51) Int. Cl.
*C07K 7/04* (2006.01)
*C07K 7/06* (2006.01)
*C07K 7/08* (2006.01)

(52) U.S. Cl. .................. 530/327; 530/328; 530/329

(58) Field of Classification Search ............. 530/327, 530/328, 329
See application file for complete search history.

(56) References Cited

U.S. PATENT DOCUMENTS

| | | | |
|---|---|---|---|
| 4,683,202 A | 7/1987 | Mullis | |
| 5,256,541 A | 10/1993 | Pouletty et al. | |
| 5,270,169 A | 12/1993 | Chang et al. | |
| 5,292,641 A | 3/1994 | Pouletty | |
| 5,482,841 A | 1/1996 | Buelow | |
| 5,710,248 A | 1/1998 | Grose | |
| 5,750,367 A | 5/1998 | Chan | |
| 5,776,746 A | 7/1998 | Denney, Jr. | |
| 5,798,209 A | 8/1998 | Chan | |
| 5,830,995 A | 11/1998 | Shoyab et al. | |
| 5,846,827 A | 12/1998 | Celis et al. | |
| 6,001,365 A | 12/1999 | Peterson et al. | |
| 6,232,445 B1 | 5/2001 | Rhode et al. | |
| 6,255,073 B1 | 7/2001 | Cai et al. | |
| 2002/0131960 A1* | 9/2002 | Sadelain et al. .......... 424/93.21 | |

FOREIGN PATENT DOCUMENTS

| | | |
|---|---|---|
| WO | WO 95/11702 | 5/1995 |
| WO | WO 97/46256 | 12/1997 |
| WO | WO 98/06749 | 2/1998 |
| WO | WO 00/23053 | 4/2000 |

OTHER PUBLICATIONS

"Molecular Cloning A Laboratory Manual", Maniatis et al., Selected Text "RNA-Dependent DNA Polymerase" p. 129, "Isolation of mRNA from Mammalian Cells" pp. 191-193, Cold Harbor Spring Laboratory (1982).
"Large Scale Production of Murine Monoclonal Antibodies Using Hollow Fiber Bioreactors", Evans et al., BioTechniques, 6(8):763-767 (1988).
"HIV-1 Reverse Transcriptase is a Target for Cytotoxic T Lymphocytes in Infected Individuals", Walker et al., Science, 240(4848):64-66 (1988).
"Assembly of MHC Class 1 Molecules Analyzed in Vitro", Townsend et al., Cell, 62(6):285-295 (1990).
"Allele-Specific Motifs Revealed by Sequencing of Self-Peptides Eluted from MHC Molecules", Falk et al., Nature, 351(6324):290-296, (1991).
"Characterization of Peptides Bound to the Class 1 MHC Molecule HLA-A2.1 by Mass Spectrometry", Hunt et al., Science, 255(5049):1261-1263 (1992).
"Peptide Binding to HLA-A2 and HLA-827 Isolated from *Escherichia coli*", Parker et al., The Journal of Biological Chemistry, 267(8):5451-5459 (1992).
"Endogenous Peptides of Soluble Major Histocompatibility Complex Class I Molecule, H-2Lds: Sequence Motif, Quantitative Binding, and Molecular Modeling of the Complex", Corr et al., J. Exp. Med., 176(6):1681-1692 (1992).
"The Specificity and Efficiency of Endogenous Peptides in the Induction of HLA Class I Alpha Chain Refolding", Tanigaki, Eur J. Immunol., 22(8):2177-2180 (1992).
"Can One Predict Antigenic Peptides for MHC Class I-Restricted Cytotoxic T Lymphocytes Useful for Vaccination?", Calin-Laurens et al., Vaccine, 11(9): 974-978 (1993).
"Direct Identification of an Endogenous Peptide Recognized by Multiple HLA-A2.1-Specific Cytotoxic T Cells", Henderson et al., Proc. Natl. Acad. Sci. USA, 90:10275-10279 (1993).
"Characterization of Endogenous Peptides Eluted from the Class I MHC Molecule HLA-B7 Determined by Mass Spectrometry and Computer Modeling", Huczko et al., J. Immunol., 151 (5):2572-2587 (1993).
"Flow-Cytometric Determination of Peptide-Class I Complex Formation Identification of p53 Peptides that Bind to HLA-A2", Zeh et al., Human Immunology, 39:79-86 (1994).

(Continued)

*Primary Examiner*—David A. Saunders
*Assistant Examiner*—F. Pierre VanderVegt
(74) *Attorney, Agent, or Firm*—Dunlap, Codding, P.C.

(57) ABSTRACT

The present invention relates generally to a methodology for the isolation, purification and identification of peptide ligands presented by MHC positive cells. In particular, the methodology of the present invention relates to the isolation, purification and identification of these peptide ligands from soluble class I and class II MHC molecules which may be uninfected, infected, or tumorgenic. The methodology of the present invention broadly allows for these peptide ligands and their comcomittant source proteins thereof to be identified and used as markers for infected versus uninfected cells and/or tumorgenic versus nontumorgenic cells with said identification being useful for marking or targeting a cell for therapeutic treatment or priming the immune response against infected cells.

15 Claims, 19 Drawing Sheets

OTHER PUBLICATIONS

"Peptide Binding to the Most Frequent HLA-A Class I Alleles Measured by Quantitative Molecular Binding Assays", Sette et al., Molecular Immunology, 31(11): 813-822 (1994).

"Binding of a Peptide Antigen to Multiple HLA Alleles Allows Definition of an A2-Like Supertype", del Guercio et al., J Immunol., 154(2):685-693 (1995).

"An HLA Class I Peptide-Binding Assay Based on Competition for Binding to Class I Molecules on Intact Human B Cells Identification of Conserved HIV-I Polymerase Peptides Binding to HLA-A0301", van der Burg et al., Human Immunology, 44:189-198 (1995).

"Measuring Interactions of MHC Class I Molecules using Surface Plasmon Resonance", Khilko et al., J. Immunol. Methods, 183(1):77-94 (1995).

"Peptide Motifs of HLA-B58, B60, B61 and B62 Molecules", Falk et al., Immunogenetics, 41(2-3):165-168 (1995).

"An Empirical Method for the Prediction of T-Cell Epitopes", Davenport et al., Immunogenetics, 42(5):392-397 (1995).

"Peptide Motifs of HLA-838 and 839 Molecules", Falk et al., Immunogenetics, 41(2-3):162-164, (1995).

"Detailed Motifs for Peptide Binding to HLA-A0201 Derived from Large Random Sets of Peptides Using Cellular Binding Assay", Drifthout et al., Human Immunology, 43(1):1-12, (1995).

"Analysis of the Structure of Naturally Processed Peptides Bound by Class I and Class II Major Histocompatibility Complex Molecules", Appella et al., EXS., 73:105-119 (1995).

"Mapping and Ranking of Potential Cytotoxic T Epitopes in the p53 Protein: Effect of Mutations and Polymorphism on Peptide Binding to Purified and Refolded HLA Molecules", Gnjatic et al., Eur. J. Immunol., 25(6):1638-1642 (1995).

"Simplified High-Sensitivity Sequencing of a Major Histocompatibility Complex Class I-Associated Immunoreactive Peptide Using Matrix-Assisted Laser Desorption/Ionization Mass Spectrometry", Woods et al., 226(1):15-25 (1995).

"Probing HLA-B7 Conformational Shifts Induced by Peptide-Binding Groove Mutations and Bound Peptide with Anti-HLA Monoclonal Antibodies", Smith et al., 157(6):2470-2478 (1996).

"Mass Spectrometry. Ionization Methods and Instrumentation", Chapman, Method Mol Biol., 61:9-28 (1996).

"HLA Allele Selection for Designing Peptide Vaccines", Kamalakar et al, Genetic Analysis: Biomolecular Engineering, 13:81-86 (1996).

"Class I-Restricted Presentation of an HIV-I gp41 Epitope Containing an N-Linked Glycosylation Site. Implications for the Mechanism of Processing of Viral Envelope Proteins", Ferris et al., J Immunol., 156(2):834-840 (1996).

"Evaluation of Hollow Fiber Bioreactors as an Alternative to Murine Ascites Production for Small Scale Monoclonal Antibody Production", Jackson et al., J. Immunol. Methods, 189(2):217-231 (1996).

"T-Cell Epitope Determination", Walden, Curr Opin Immunol., 8(1):68-74 (1996).

"Large-Scale Production of Class I Bound Peptides: Assigning a Signature to HLA-B1501", Prilliman et al., Immunogentics, 45(6):379-385 (1997).

"HLA Class I Binding Motifs Derived from Random Peptide Libraries Differ at the Cooh Terminus from Those of Eluted Peptides", Davenport et al., J. Exp. Med., 185(2): 367-371 (1997).

"Stability of Empty and Peptide-Loaded Class II Major Histocompatibility Complex Molecules at Neutral and Endosomal pH: Comparison to Class I Proteins", Reich et al., Proc. Natl. Acad. Sci. USA, 94:2495-2500 (1997).

"Human Peptide Transporter Deficiency: Importance of HLA-B in the Presentation of Tap-Independent EBV Antigens", de la Salle et al., J. Immunol., 158(10):4555-4563 (1997).

"A Novel, Highly Efficient Peptide-HLA Class I Binding Assay Using Unfolded Heavy Chain Molecules: Identification of HIV-1 Derived Peptides That Bind to HLA-A0201 HLA-A0301", Tan et al., J. Immunol. Methods, 205(2): 201-209 (1997).

"Large-Scale Production of Class I Bound Peptides: Assigning a Signature to HLA-B1501", Prilliman et al., Immunogenetics, 45(6):379-385 (1997).

"Synthetic Peptides Based on Chlamydia trachomatis Antigens Identify Cytotoxic T Lymphocyte Responses in Subjects from a Trachoma-Endemic Population", Holland et al., Clin. Exp. Immunol., 107(1):44-49 (1997).

"Complexity Among Constituents of the HLA-B1501 Peptide Motif", Prilliman et al., Immunogenetics, 48:89-97 (1998).

"A Microcapillary Column Switching HPLC-Electrospray Ionization MS System for the Direct Identification of Peptides Presented by Major Histocompatibility Complex Class I Molecules", van der Heeft et al., Anal. Chem., 70:3742-3751 (1998).

"Synthetic Peptides of Human Papillomavirus Type 18 E6 Harboring HLA-A2.1 Motif can Induce Peptide-Specific Cytotoxic T-Cells From Peripheral Blood Mononuclear Cells of Healthy Donors", Yoon et al., Virus Research, 54:23-29 (1998).

"MHCPEP, A Database of MHC-Binding Peptides: Update 1997", Brusic et al., Nucleic Acids Research, 26(1): 368-371 (1998).

"Prediction of MHC Class II-Binding Peptides Using an Evolutionary Algorithm and Artificial Neural Network", Brusic et al., Bioinformatics, 14(2): 121-130 (1998).

"Efficient Generation of Major Histocompatibility Complex Class I-Peptide Complexes Using Synthetic Peptide Libraries", Stevens et al., The Journal of Biological Chemistry, 273(5):2874-2884 (1998).

"Neural Network-Based Prediction of Candidate T-Cell Epitopes", Honeyman et al., Nat. Biotechnol., 16(10): 966-969 (1998).

"Direct Identification of Major Histocompatibility Complex Class I-Bound Tumor-Associated Peptide Antigens of a Renal Carcinoma Cell Line by a Novel Mass Spectrometric Method", Flad et al., Cancer Research, 58(24):5803-5811 (1998).

"Structure and Function of a Membrane-Bound Murine MHC Class I Molecule", Celia et al., Proc. Natl. Acad. Sci. USA, 96:5634-5639 (1999).

"Identification of HLA-A3 and -B7-Restricted CTL Response to Hepatitis C Virus in Patients with Acute and Chronic Heptitis C", Chang et al., J. Immunol., 162(2):1156-1164 (1999).

"HLA-B15 Peptide Ligands are Preferentially Anchored at Their C Termini", Prilliman et al., J. Immunol., 162(12):7277-7284 (1999).

"Structure and Function of a Membrane-Bound Murine MHC Class I Molecule", Proc. Natl. Acad. Sci. USA, 96:5634-5639 (1999).

"Alpha-2 Domain Polymorphism and HLA Class I Peptide Loading", Prilliman et al., Tissue Antigens, 54(5):450-460 (1999).

"Syfpeithi: A Database for MHC Ligands and Peptide Motifs", Rammensee et al., Immunogenetics, 50:213-219 (1999).

"Peptide Motif of the Class I Molecule HLA-B1503", Prilliman et al., Immunogenetics, 49:144-146 (1999).

"Clad Against All Clades- Can Vaccinomics Build a World HIV Vaccine?", Hollon, The Scientist, 14(18):1 (2000).

"Human Immunology—26th Annual Ashi Meeting Abstracts 2000", 61: Supplement 2 (2000).

"C-Terminal Epitope Tagging Facilitates Comparative Ligand Mapping from MHC Class I Positive Cells", Hickman et al., Human Immunology, 61:1339-1346 (2000).

"Production and Application of Individual HLA Protein", Hildebrand et al., Human Immunology, abstract, vol. 61, No. Suppl 2, p. S81 XP008007733(2000).

"FIMM, a database of functional molecular immunology", C Schonbach et al., Nucleic Acids Research, vol. 28, No. 1, Jan. 2000, pp. 222-224, XP002242984 Oxford, UK figure 1; table 1.

"Rapid Determination of HLA B 07 Ligands From the West Nile Virus NY99 Genome", De Groot et al., Emerging Infectious Diseases, 7(4):706-713 (2001).

"Examination of Possible Structural Constraints of MHC-Binding Peptides by Assessment of Their Native Structure Within Their Source Proteins", Schueler-Furman et al., Proteins: Structure, Function, and Genetics, 45:47-54 (2001).

"Use of Fluorescence Polarization to Monitor MHC-Peptide Interactions in Solution", Dedler et al, Journal of Immunological Methods, 255:57-66 (2001).

"Peptide/MHC Monomers can be Inserted into Artificial Lipid Bilayers as Artificial Antigen Presentation Constructs", Jiang et al., Section of Transplantation Immunology, BMT Department, M.D. Anderson Cancer Center, Houston, Texas, Abstract # 2126 (2001).

"Neural Network Method for Predicting Peptides That Bind Major Histocompatibility Complex Molecules", Gulukota et al., Methods Mol. Biol., 156:201-209 (2001).

"Structure of Peptides Associated with MHC Class I Molecules", Engelhard, V.H., Current Opinion in Immunology, vol. 6, pp. 13-23 (1994).

"Isolation and Analysis of Naturally Processed Viral Peptides as Recognized by Cytotoxic T Cells", Rotzschke et al., Nature, vol. 348, pp. 252-254 (Nov. 1990).

"Endogenous Peptides Bound to HLA-A3 Possess a Specific Combination of Anchor Residues that Permit Identification of Potential Antigenic Peptides", Dibrino et al., Proc. Natl. Acad. Sci. USA, vol. 90, pp. 1508-1512 (Feb. 1993).

"Unisyn Strives for Flexibility and Scale", Membrane & Separation Technology News, vol. 16, No. 7, pp. N/A (Mar. 1, 1998).

"BioPharm", Unisyn Technologies, Inc., vol. N/A, pp. 53 (Dec. 1996).

"Pet System Manual", Novagen, Inc., 6$^{th}$ Edition, pp. 4 and 23, see entire page selection (Aug. 1995).

"Fusion proteins in biotechnology and structural biology", Nilsson et al., Current Opinion in Structural Biology, vol. 2, pp. 569-575, see entire article, espec. p. 572 @ col. 1 (1992).

"Generic Liposome Reagent for Immunoassays", Plant et al., Analytical Biochemistry, vol. 176, Issue 2, pp. 420-426 (1989).

"Dissociation of the Peptide-MHC Class I Complex Limits the Binding Rate of Exogenous Peptide", Ojcius et al., Journal of Immunology, vol. 151, No. 11, pp. 6020-6026 (1993).

Dissociation of the Peptide/MHC Class I Complex: pH Dependence and Effect of Endogenous Peptides on the Activation Energy, Ojcius et al., Biochemical and Biophysical Research Communications, vol. 197, No. 3, pp. 1216-1222 (1993).

"Role of HLA-A Motifs in Identification of Potential CTL Epitopes Inhuman Papillomavirus Type 16 E6 and E7 Proteins", Kast et al., Journal of Immunology, vol. 152, No. 8, pp. 3904-3912 (1994).

"The Accessibility of Peptides Bound to the Mouse MHC Class II Molecule IE-d Studied by Fluorescence", Federation of European Biochemical Societies Letters, vol. 342, No. 3, pp. 230-234 (1994).

"A New Murine Lymphocytotoxic Monoclonal Antibody Recognizing HLA-A2, -A28 and -A9", Mizuno et al., Tissue Antigens, 48:224-227 9(1996).

"The Use of Magnetic Beads Coated with Soluble HLA Class I or Class II Proteins in Antibody Screening and for Specificity Determination of Donor-Reactive Antibodies", Sumitran-Karuppan et al., Transplantation, 61(10):1539-1546 (1996).

"Antibody Screening by enzyme-Linked Immunosorbent Assay Using Pooled Soluble HLA in Renal Transplant Candidates", Zaer et al., Transplantation, 63(1):48-51 (1997).

"In Vitro Induction of Specific Cytotoxic T Lymphocytes using Recombinant Single-Chain MHC Class I/Peptide Complexes", Lone et al., Journal of Immunotherapy, 21(4):283-294 (1998).

"A Mutant Human B$_2$-Microglobulin Can be Used to Generate Diverse Multmeric Class I Peptide Complexes as Specific Probes for T Cell Receptors", Walter et al., Journal of Immunological Methods 214:41-50 (1998).

"Molecular Cloning A Laboratory Manual", Maniatis et al., Selected Text "Synthesis and Cloning of DNA" vol. 1, pp. 211-246, Cold Harbor Spring Laboratory (1982).

"In Vitro Peptide Binding to Soluble Empty Class I Major Histocompatibility Complex Molecules Isolated From Transfected Drosophila Melanogaster Cells", Matsumura et al., The Journal of Biological Chemistry, vol. 267, ISS Nov. 25:23589-23595 (1992).

"A Soluble Divalent Class I Major Histocompatibility Complex Molecule Inhibits Aloreactive T Cells at Nonmolar Concentrations", Dal Porto et al., Proc. Natl., Acad. Sci. USA, 90:6671-6675 (1993).

"Targeted Amplification of Alternatively Spliced Transcripts of Major Histocompatibility Complex Class I Heavy Chain", Yang et al., Journal of Immunological Methods, 175:265-279 (1994).

"Prediction of Well-Conserved HIV-1 Ligands Using a Matrix-Based Algorithm, Epimatrix", Schafer et al., Vaccine, 16(19):1880-1884 (1998).

"Unisyn Strives for Flexibility and Scale", Prompt, Membrane and Separation Technology News, ISSN 0737-8483, Mar. 1, 1998.

* cited by examiner

FIG. 2

| | 1 | 2 | 3 | 4 | 5 | 6 | 7 | 8 | 9 |
|---|---|---|---|---|---|---|---|---|---|
| B*1501 | | | | | | | | | |
| Dominant | - | Q | K | - | - | - | - | - | Y |
| | | | F | | | | | | |
| | | | N | | | | | | |
| | | | R | | | | | | |
| | | | Y | | | | | | |
| Strong | - | M | P | P | G | - | - | - | F |
| | | L | H | D | I | | | | |
| | | V | A | G | | | | | |
| | | | | E | | | | | |

| | 1 | 2 | 3 | 4 | 5 | 6 | 7 | 8 | 9 |
|---|---|---|---|---|---|---|---|---|---|
| B*1501-HIS | | | | | | | | | |
| Dominant | - | Q | F | D | - | - | - | - | Y |
| | | | K | | | | | | F |
| | | | N | | | | | | |
| | | | P | | | | | | |
| | | | R | | | | | | |
| | | | Y | | | | | | |
| Strong | - | L | H | E | - | - | - | - | |
| | | M | A | P | | | | | |
| | | V | | G | | | | | |

| | 1 | 2 | 3 | 4 | 5 | 6 | 7 | 8 | 9 |
|---|---|---|---|---|---|---|---|---|---|
| B*1501-FLAG | | | | | | | | | |
| Dominant | - | Q | K | D | - | - | - | - | Y |
| | | M | F | | | | | | F |
| | | | N | | | | | | |
| | | | P | | | | | | |
| | | | R | | | | | | |
| | | | Y | | | | | | |
| Strong | - | L | D | E | - | - | - | - | |
| | | V | H | G | | | | | |
| | | | A | P | | | | | |

LIGAND    GPRTAALGLL

Source HLA/Purification    HLA-B*0702 from Sup-T1 subclone B*0702tHIS subclone 2.44
                           Brandee Run D
                           Purification number 1 (W6/32)
                           Fraction 30 Infected Protein Source             RETICULOCALBIN 2
GI or accession #          4506457
Ligand start amino acid    4
Ligand length              Decamer
Predicted binding (Parker) 800.000
Protein information from GI
LOCUS    NP_002893    317 aa    PRI    31-OCT-2000
DEFINITION reticulocalbin 2, EF-hand calcium binding domain; Reticulocalbin 2, EF-hand calcium binding domain (endoplasmic rreticulum calcium-binding protein, 55kD) [Homo sapiens].
COMMENT REVIEWED REFSEQ: This record has been curated by NCBI staff. The reference sequence was derived from 8669.1.

Summary: Reticulocalbin 2 is a calcium-binding protein located in the lumen of the ER. The protein contains six conserved regions with similarity to a high affinity Ca(+2)-binding motif, the EF-hand. The RCN2 gene maps to the same region as type 4 Bardet-Biedl syndrome (MIM:600374), suggesting a possible causative role for reticulocalbin 2 in the disorder.

Protein sequence
  1 mrlgprtaal gllllcaaaa gagkaeelhy plgerrsdyd reallgvqed vdeyvklghe
 61 eqqkrlqaii kkidldsdgf lteselsswi qmsfkhyamq eakqqfveyd knsddtvtwd
121 eyniqmydrv idfdentald daeeestfkl hlkdkkrfek anqdsgpgls leefiafehp
181 eevdymtefv iqealeehdk ngdgfvslee flgdyrwdpt anedpewilv ekdrfvndyd
241 kdndgrldpq ellpwvvpnn qgiaqceealh lidemdlngd kklseeeile npdllfltsea
301 tdygrqlhdd yfyhdel

FIG. 9

Entrez-Pubmed listings:

Carper D, John M, Chen Z, Subramanian S, Wang R, Ma W, Spector A. Gene expression analysis of an H(2)O(2)-resistant lens epithelial cell line. Free Radic Biol Med. 2001 Jul 1;31(1):90-7.

Nimmrich I, Erdmann S, Melchers U, Finke U, Hentsch S, Moyer MP, Hoffmann I, Muller O. Seven genes that are differentially transcribed in colorectal tumor cell lines. Cancer Lett. 2000 Nov 10;160(1):37-43.

Yu LR, Zeng R, Shao XX, Wang N, Xu YH, Xia QC. Identification of differentially expressed proteins between human hepatoma and normal liver cell lines by two-dimensional electrophoresis and liquid chromatography-ion trap mass spectrometry. Electrophoresis. 2000 Aug;21(14):3058-68

Honore B, Vorum H. The CREC family, a novel family of multiple EF-hand, low-affinity Ca(2+)-binding proteins localised to the secretory pathway of mammalian cells. FEBS Lett. 2000 Jan 21;466(1):11-8. Review.

Kent J, Lee M, Schedl A, Boyle S, Fantes J, Powell M, Rushmere N, Abbott C, van Heyningen V, Bickmore WA. The reticulocalbin gene maps to the WAGR region in human and to the Small eye Harwell deletion in mouse. Genomics. 1997 Jun 1;42(2):260-7.

Liu Z, Brattain MG, Appert H. Differential display of reticulocalbin in the highly invasive cell line, MDA-MB-435, versus the poorly invasive cell line, MCF-7. Biochem Biophys Res Commun. 1997 Feb 13;231(2):283-9.

Tachikui H, Navet AF, Ozawa M. Identification of the Ca(2+)-binding domains in reticulocalbin, an endoplasmic reticulum resident Ca(2+)-binding protein with multiple EF-hand motifs. J Biochem (Tokyo). 1997 Jan;121(1):145-9.

Weis K, Griffiths G, Lamond AI. The endoplasmic reticulum calcium-binding protein of 55 kDa is a novel EF-hand protein retained in the endoplasmicreticulum by a carboxyl-terminal His-Asp-Glu-Leu motif. J Biol Chem. 1994 Jul 2;269(29):19142-50.

Chen JJ, Reid CE, Band V, Androphy EJ. Interaction of papillomavirus E6 oncoproteins with a putative calcium-binding protein. Science. 1995 Jul 28;269(5223):529-31.

Summary of Entrez-pubmed entries:
Reticulocalbin is a 55kD protein located in the lumen of the ER and, as the name implies, it binds calcium. It is a member of a large family of similar proteins that are found along the secretory pathway in human cells. No one knows the exact function of this protein, but it is hypothesized that it is a calcium-dependent molecular chaperone. Interestingly, this protein has been described as being upregulated in a variety of cancerous cell lines, including colorectal tumors, metastatic breast cancers, and hepatomas. In several instances, there is a multi-fold increase in its expression in the cancerous lines. In the case of breast cancer cell lines, it is found only in the invasive, metastatic lines and thus has been implicated as a potentiator of metastasis. Another interesting point is that this protein was also identified independently as the E6BP, or E6 binding protein, which binds to the human papilloma virus E6 protein. The fact that this protein is an ER resident protein and that the B7-binding peptide is derived from the leader sequence which should be cleaved in the ER gives further support to the likelihood of presentation of this peptide should reticulocalbin be upregulated in any number of cancerous or virally infected cells.

FIGURE 10

User Parameters and Scoring Information

| | |
|---|---|
| method selected to limit number of results | explicit number |
| number of results requested | 20 |
| HLA molecule type selected | B7 |
| length selected for subsequences to be scored | 10 |
| echoing mode selected for input sequence | Y |
| echoing format | numbered lines |
| length of user's input peptide sequence | 317 |
| number of subsequence scores calculated | 308 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 4 | GPRTaALGLL | 800.000 |
| 2 | 244 | DGRLdPQELL | 60.000 |
| 3 | 19 | AAGAgKAEEL | 36.000 |
| 4 | 220 | TANEdPEWIL | 18.000 |
| 5 | 268 | ALHLiDEMDL | 12.000 |
| 6 | 160 | KANQdSGPGL | 12.000 |
| 7 | 166 | GPGLsLEEFI | 8.000 |
| 8 | 287 | EILEnPDLFL | 6.000 |
| 9 | 6 | RTAAlGLLLL | 4.000 |
| 10 | 260 | NQGIaQEEAL | 4.000 |

Peptide is expected to bind to B7 with high affinity. (Estimated half time of dissociation is 800.00)

Fig. 11

PEPTIDE BINDING PREDICTION USING RAMMENSEE'S SYPEITHI PREDICTION:

Search Report

Return to search conditions
HLA-B*0702 decamers

HLA-B*0702 decamers

| Pos | 1 | 2 | 3 | 4 | 5 | 6 | 7 | 8 | 9 | 0 | Score |
|---|---|---|---|---|---|---|---|---|---|---|---|
| 4 | G | P | R | T | A | A | L | G | L | L | 22 |
| 166 | G | P | G | L | S | L | E | E | F | I | 18 |
| 291 | N | P | D | L | F | L | T | S | E | A | 18 |
| 248 | D | P | Q | E | L | L | P | W | V | V | 17 |
| 1 | M | R | L | G | P | R | T | A | A | L | 15 |
| 6 | R | T | A | A | L | G | L | L | L | L | 15 |
| 35 | R | R | S | D | Y | D | R | E | A | L | 15 |
| 199 | D | K | N | G | D | G | F | V | S | L | 15 |
| 19 | A | A | G | A | G | K | A | E | E | L | 14 |
| 287 | E | I | L | E | N | P | D | L | F | L | 14 |
| 5 | P | R | T | A | A | L | G | L | L | L | 13 |
| 30 | Y | P | L | G | E | R | R | S | D | Y | 13 |
| 36 | R | S | D | Y | D | R | E | A | L | L | 13 |
| 48 | Q | E | D | V | D | E | Y | V | K | L | 13 |
| 72 | K | I | D | L | D | S | D | G | F | L | 13 |
| 130 | V | I | D | F | D | E | N | T | A | L | 13 |

Figure 12.

Peptide is predicted to bind HLA-B*0702 with a high affinity. Rammensee's prediction scores this peptide 22.

PAProC predicts the following (109) proteasomal cleavages (made by human proteasome type III) in Name (317 amino acids):

| | |
|---|---|
| 1 | MRI\|GPRTA \| ALGLLL\|LCAAAA |
| 21 | GAGK \| AE \| ELHY \| PLGE \| RRSDYD \| |
| 41 | REALLGV \| Q \| EDVD \| EYV \| K \| L \| GHE \| |
| 61 | E \| QQKR \| L \| Q \| AIIKK \| I \| DLD \| SDG \| F |
| 81 | L \| TE \| SEL \| S \| SW \| IQM \| S \| FKH \| YA \| M \| Q \| |
| 101 | EA \| KQQ \| FV \| EYD \| KN \| S \| D \| DTVTW \| D |
| 121 | EY \| NIQMYDRV \| I \| DF \| D \| ENTALD \| |
| 141 | D \| AE \| EE \| S \| F \| R \| K \| L \| HLK \| D \| KKR \| FE \| K |
| 161 | A \| N \| QDSG \| PGL \| SL \| E \| EFI \| AF \| E \| H \| P \| |
| 181 | EEVD \| YMTEF \| V \| I \| Q \| E \| ALEE \| HDK |
| 201 | NGDGFV \| SL \| E \| EFL \| GD \| Y \| RWDPT |
| 221 | AN \| EDPEWILV \| E \| KD \| RFV \| ND \| YD |
| 241 | KD \| NDG \| RLDPQELL \| PWVVPNN \| |
| 261 | QGIAQ \| E \| EALHLI \| D \| EMDLNG \| D |
| 281 | KK \| L \| SE \| E \| EILENPDLFL \| T \| SE \| A |
| 301 | T \| DYG \| RQL \| HD \| DY \| FYHDEL |

Fig. 13.

NetChop 2.0 Prediction Results

The predictions for proteasome cleavage sites of 1 sequence
Threshold used: 0.5
************************************** NetChop predictions **************************************
  317 Sequence
mrlgprtaalglllcaaaagagkaeelhyplgerrsdydreallgvqedvdeyvklgheeqgkrlgaiikkidldsdgf
S......S.S.SS.S.S...........S.S.....S......S...S.....SSS.................
lteselsswigmsfkhyamgeakqqfveydknsddtvtwdeynigmydrvidfdentalddaeeesfrklhlkdkkrfek
..S..S........S.......S..S.S.......SS........S.SS.......SS.S.S.....S.....S
anqdsgpglsleefiafehpeevdymtefvigealeehdkngdgfvsleeflgdyrwdptanedpewilvekdrfvndyd
..S...S.S..S...........SS..........S.S.S..S.S.S.....S........S..........S.
kdndgridpqellpwvvpnnqgiaqeealhlidemdingdkklseeeilenpdlfltseatdygrqlhddyfyhdel
S.S.....SS.........S.........S........S....S......SS.

Fig. 14.

OTHER PEPTIDES PREDICTED TO BE PRESENTED FROM THIS PROTEIN:

A*0201

Nonamers

| 1 | 2 | 3 | 4 | 5 | 6 | 7 | 8 | 9 | Score |
|---|---|---|---|---|---|---|---|---|-------|
| R | L | G | P | R | T | A | A | L | 27 |
| A | L | L | G | V | Q | E | D | V | 26 |
| I | L | V | E | K | D | R | F | V | 25 |
| T | A | A | L | G | L | L | L | L | 23 |
| R | L | Q | A | I | H | K | K | I | 23 |
| I | L | E | N | P | D | L | F | L | 23 |
| A | L | G | L | L | L | C | A | A | 22 |
| G | L | L | L | L | C | A | A | A | 21 |
| I | A | F | E | H | P | E | E | V | 21 |
| Y | D | R | E | A | L | L | G | V | 20 |
| S | L | E | F | F | H | A | F | E | 20 |
| L | L | C | A | A | A | G | A | E | 19 |
| A | G | A | G | K | A | E | E | L | 19 |
| I | A | Q | E | E | A | L | H | L | 19 |
| R | T | A | A | L | G | L | L | L | 18 |
| K | A | E | E | L | H | Y | P | L | 18 |
| K | N | G | D | G | F | V | S | L | 18 |
| S | L | E | E | F | L | G | D | Y | 18 |

Decamers

| 1 | 2 | 3 | 4 | 5 | 6 | 7 | 8 | 9 | 0 | Score |
|---|---|---|---|---|---|---|---|---|---|-------|
| A | M | Q | E | A | K | Q | Q | F | V | 22 |
| F | I | A | F | E | H | P | E | E | V | 22 |
| G | I | A | Q | E | E | A | L | H | L | 22 |
| A | L | H | L | I | D | E | M | D | L | 22 |
| R | T | A | A | L | G | L | L | L | A | 21 |
| A | L | G | L | L | L | C | A | A | A | 21 |
| L | L | L | C | A | A | A | G | A | E | 21 |
| Y | M | T | E | F | V | I | Q | E | A | 21 |
| I | A | Q | L | L | A | L | H | L | L | 21 |
| G | L | L | V | E | A | L | H | A | A | 20 |
| W | I | S | E | E | L | L | C | A | A | 20 |
| K | L | L | V | E | K | D | R | F | L | 20 |
| E | I | L | E | N | P | D | L | L | L | 19 |
| A | A | L | G | L | L | L | D | G | F | 19 |
| K | I | D | L | D | S | D | E | N | T | 19 |
| V | I | D | F | D | E | N | T | D | L | 19 |
| I | L | E | N | P | D | L | F | L | T | 18 |
| A | G | A | G | K | A | E | E | L | S | 18 |
| F | L | T | E | S | E | L | S | W | G | 18 |
| K | A | N | Q | D | S | G | P | G | L | 18 |
| L | I | D | E | M | D | L | N | G | D | 17 |
| M | R | L | G | P | R | T | A | A | L | 17 |
| L | L | L | C | A | A | A | A | A | G | 17 |

Nonamers

| 1 | 2 | 3 | 4 | 5 | 6 | 7 | 8 | 9 | Score |
|---|---|---|---|---|---|---|---|---|-------|
| S | L | E | E | F | L | G | D | Y | 28 |
| W | D | E | Y | N | I | Q | M | Y | 26 |
| E | D | D | R | R | V | N | D | Y | 26 |
| R | L | D | P | Q | E | L | L | P | 25 |
| A | G | K | A | E | E | L | H | Y | 22 |
| A | T | D | Y | G | R | V | E | H | 22 |
| E | E | K | P | E | E | I | D | Y | 20 |
| F | E | H | E | E | W | L | E | V | 20 |
| N | L | E | Y | E | I | L | G | N | 20 |
| L | D | D | R | V | K | L | L | H | 20 |
| V | Y | D | M | A | A | L | H | G | 19 |
| D | I | Q | F | V | I | K | E | Y | 18 |
| W | T | E | N | P | D | Q | F | A | 18 |
| M | L | N | — | — | — | L | L | L | 18 |
| I | — | E | — | — | — | — | — | — | 18 |

Decamers

| 1 | 2 | 3 | 4 | 5 | 6 | 7 | 8 | 9 | 0 | Score |
|---|---|---|---|---|---|---|---|---|---|-------|
| S | D | D | T | V | T | W | D | E | Y | 27 |
| T | W | E | E | Y | N | I | Q | M | Y | 26 |
| A | F | D | H | P | R | E | V | D | Y | 26 |
| A | T | D | Y | G | R | Q | L | M | D | 23 |
| G | A | G | K | A | E | E | I | H | Y | 21 |
| N | E | D | P | E | W | I | L | V | E | 21 |
| R | L | D | P | Q | E | L | L | P | W | 21 |
| D | W | D | S | D | G | F | R | T | H | 20 |
| S | V | H | Q | M | S | L | K | H | D | 20 |
| V | P | I | E | E | R | R | R | G | Q | 20 |
| Y | L | L | K | L | S | W | S | D | E | 19 |
| E | S | E | L | Q | Q | F | I | Q | Y | 18 |
| Q | E | A | H | Y | Q | P | V | E | A | 18 |
| A | H | E | Q | Q | K | R | P | G | L | 17 |
| H | N | E | S | G | P | L | L | E | E | 17 |
| N | Q | D | G | F | V | S | L | L | V | 17 |
| A | N | D | D | P | E | W | H | D | Y | 17 |
| V | E | K | D | R | F | V | N | D | P | 17 |
| D | K | N | N | D | G | R | L | L | P | 17 |
| A | Q | E | E | A | L | H | L | I | D | 17 |

View of previous fraction showing 484.72:
Fraction 29

No evidence of the peptide in this fraction.

View of post fraction showing 484.72:
Fraction 31

No evidence of the peptide in this fraction.

COMPARATIVE LIGAND MAPPING FROM MHC POSITIVE CELLS

CROSS-REFERENCE TO RELATED APPLICATIONS

This application claims the benefit of: provisional patent application U.S. Ser. No. 60/240,143, filed Oct. 10, 2000, entitled "C-TERMINAL EPITOPE TAGGING FACILITATES COMPARATIVE LIGAND MAPPING FROM MHC CLASS I POSITIVE CELLS"; provisional patent application U.S. Ser. No. 60/299,452, filed Jun. 20, 2001, entitled "HIV EPITOPES IDENTIFIED BY THE METHOD OF C-TERMINAL EPITOPE TAGGING FOR COMPARATIVE LIGAND MAPPING FROM MHC CLASS I POSITIVE CELLS"; provisional patent application U.S. Ser. No. 60/256,410, filed Dec. 18, 2000, entitled "HLA PRODUCTION FROM GENOMIC DNA"; provisional patent application U.S. Ser. No. 60/256,409, entitled "HLA PRODUCTION FROM cDNA" filed Dec. 18, 2000; and provisional patent application U.S. Ser. No. not yet assigned, entitled "PRODUCTION OF SOLUBLE HUMAN HLA CLASS I PROTEINS FROM GENOMIC DNA" filed Oct. 9, 2001 all of which are expressly incorporated herein by reference.

STATEMENT REGARDING FEDERALLY SPONSORED RESEARCH OR DEVELOPMENT

This work was funded in part by a contract from the National Institutes of Health: Contract number NO. 1-AI-95360 entitled "Mapping and Characterization of Viral Epitopes". As such, the Government may own certain rights in and to this application.

BACKGROUND OF THE INVENTION

1. Field of the Invention

The present invention relates generally to a methodology for the isolation, purification and identification of peptide ligands presented by MHC positive cells. In particular, the methodology of the present invention relates to the isolation, purification and identification of these peptide ligands from soluble class I and class II MHC molecules which may be uninfected, infected, or tumorigenic. The methodology of the present invention broadly allows for these peptide ligands and their concomitant source proteins thereof to be identified and used as markers for infected versus uninfected cells and/or tumorigenic versus nontumorigenic cells with said identification being useful for marking or targeting a cell for therapeutic treatment or priming the immune response against infected cells.

2. Description of the Background Art

Class I major histocompatibility complex (MHC) molecules, designated HLA class I in humans, bind and display peptide antigen ligands upon the cell surface. The peptide antigen ligands presented by the class I MHC molecule are derived from either normal endogenous proteins ("self") or foreign proteins ("nonself") introduced into the cell. Nonself proteins may be products of malignant transformation or intracellular pathogens such as viruses. In this manner, class I MHC molecules convey information regarding the internal fitness of a cell to immune effector cells including but not limited to, $CD8^+$ cytotoxic T lymphocytes (CTLs), which are activated upon interaction with "nonself" peptides, thereby lysing or killing the cell presenting such "nonself" peptides.

Class II MHC molecules, designated HLA class II in humans, also bind and display peptide antigen ligands upon the cell surface. Unlike class I MHC molecules which are expressed on virtually all nucleated cells, class II MHC molecules are normally confined to specialized cells, such as B lymphocytes, macrophages, dendritic cells, and other antigen presenting cells which take up foreign antigens from the extracellular fluid via an endocytic pathway. The peptides they bind and present are derived from extracellular foreign antigens, such as products of bacteria that multiply outside of cells, wherein such products include protein toxins secreted by the bacteria that often times have deleterious and even lethal effects on the host (e.g. human). In this manner, class II molecules convey information regarding the fitness of the extracellular space in the vicinity of the cell displaying the class II molecule to immune effector cells, including but not limited to, $CD4^+$ helper T cells, thereby helping to eliminate such pathogens the examination of such pathogens is accomplished by both helping B cells make antibodies against microbes, as well as toxins produced by such microbes, and by activating macrophages to destroy ingested microbes.

Class I and class II HLA molecules exhibit extensive polymorphism generated by systematic recombinatorial and point mutation events; as such, hundreds of different HLA types exist throughout the world's population, resulting in a large immunological diversity. Such extensive HLA diversity throughout the population results in tissue or organ transplant rejection between individuals as well as differing susceptibilities and/or resistances to infectious diseases. HLA molecules also contribute significantly to autoimmunity and cancer. Because HLA molecules mediate most, if not all, adaptive immune responses, large quantities of pure isolated HLA proteins are required in order to effectively study transplantation, autoimmunity disorders, and for vaccine development.

There are several applications in which purified, individual class I and class II MHC proteins are highly useful. Such applications include using MHC-peptide multimers as immunodiagnostic reagents for disease resistance/autoimmunity; assessing the binding of potentially therapeutic peptides; elution of peptides from MHC molecules to identify vaccine candidates; screening transplant patients for preformed MHC specific antibodies; and removal of anti-HLA antibodies from a patient. Since every individual has differing MHC molecules, the testing of numerous individual MHC molecules is a prerequisite for understanding the differences in disease susceptibility between individuals. Therefore, purified MHC molecules representative of the hundreds of different HLA types existing throughout the world's population are highly desirable for unraveling disease susceptibilities and resistances, as well as for designing therapeutics such as vaccines.

Class I HLA molecules alert the immune response to disorders within host cells. Peptides, which are derived from viral- and tumor-specific proteins within the cell, are loaded into the class I molecule's antigen binding groove in the endoplasmic reticulum of the cell and subsequently carried to the cell surface. Once the class I HLA molecule and its loaded peptide ligand are on the cell surface, the class I molecule and its peptide ligand are accessible to cytotoxic T lymphocytes (CTL). CTL survey the peptides presented by the class I molecule and destroy those cells harboring ligands derived from infectious or neoplastic agents within that cell.

While specific CTL targets have been identified, little is known about the breadth and nature of ligands presented on the surface of a diseased cell. From a basic science perspective, many outstanding questions have permeated through the art regarding peptide exhibition. For instance, it has been demonstrated that a virus can preferentially block expression of HLA class I molecules from a given locus while leaving expression at other loci intact. Similarly, there are numerous reports of cancerous cells that fail to express class I HLA at particular loci. However, there are no data describing how (or if) the three classical HLA class I loci differ in the immuno-regulatory ligands they bind. It is therefore unclear how class I molecules from the different loci vary in their interaction with viral- and tumor-derived ligands and the number of peptides each will present.

Discerning virus- and tumor-specific ligands for CTL recognition is an important component of vaccine design. Ligands unique to tumorigenic or infected cells can be tested and incorporated into vaccines designed to evoke a protective CTL response. Several methodologies are currently employed to identify potentially protective peptide ligands. One approach uses T cell lines or clones to screen for biologically active ligands among chromatographic fractions of eluted peptides. (Cox et al., Science, vol 264, 1994, pages 716-719, which is expressly incorporated herein by reference in its entirety) This approach has been employed to identify peptides ligands specific to cancerous cells. A second technique utilizes predictive algorithms to identify peptides capable of binding to a particular class I molecule based upon previously determined motif and/or individual ligand sequences. (De Groot et al., Emerging Infectious Diseases, (7) April, 2001, which is expressly incorporated herein by reference in its entirety) Peptides having high predicted probability of binding from a pathogen of interest can then be synthesized and tested for T cell reactivity in precursor, tetramer or ELISpot assays.

However, there has been no readily available source of individual HLA molecules. The quantities of HLA protein available have been small and typically consist of a mixture of different HLA molecules. Production of HLA molecules traditionally involves growth and lysis of cells expressing multiple HLA molecules. Ninety percent of the population is heterozygous at each of the HLA loci; codominant expression results in multiple HLA proteins expressed at each HLA locus. To purify native class I or class II molecules from mammalian cells requires time-consuming and cumbersome purification methods, and since each cell typically expresses multiple surface-bound HLA class I or class II molecules, HLA purification results in a mixture of many different HLA class I or class II molecules. When performing experiments using such a mixture of HLA molecules or performing experiments using a cell having multiple surface-bound HLA molecules, interpretation of results cannot directly distinguish between the different HLA molecules, and one cannot be certain that any particular HLA molecule is responsible for a given result. Therefore, a need existed in the art for a method of producing substantial quantities of individual HLA class I or class II molecules so that they can be readily purified and isolated independent of other HLA class I or class II molecules. Such individual HLA molecules, when provided in sufficient quantity and purity, would provide a powerful tool for studying and measuring immune responses.

Therefore, there exists a need in the art for improved methods of epitope discovery and comparative ligand mapping for class I and class II MHC molecules, including methods of distinguishing an infected/tumor cell from an uninfected/non-tumor cell. The present invention solves this need by coupling the production of soluble HLA molecules with an epitope isolation, discovery, and direct comparison methodology.

BRIEF DESCRIPTION OF THE DRAWINGS

FIG. 2. Edman sequence analysis of soluble B*1501, B*1501-HIS and B*1501-FLAG. Residue intensity was categorized as either dominant (3.5-fold or more picomolar increase over previous round) or strong (2.5 to 3.5-fold increase over prior round).

FIG. 9. Results of a PubMed BLAST search with the sequence GPRTAALGLL identified in FIG. 8.

FIG. 10. Summary of Results of Entrez-PubMed search for the word "reticulocalbin".

FIG. 11. Results of a peptide-binding algorithm performed using Parker's Prediction using the entire source protein, reticulocalbin, which generates a list of peptides which are bound by the B*0702 HLA allele.

FIG. 12. Results of a peptide-binding algorithm performed using Rammensee's SYPEITHI Prediction using the entire source protein, reticulocalbin, which generates a list of peptides which are bound by the B*0702 HLA allele.

FIG. 13. Results of a predicted proteasomal cleavage of the complete reticulocalbin protein using the cleavage predictor PaProC.

FIG. 14. Results of a predicted proteasomal cleavage of the complete reticulocalbin protein using the cleavage predictor NetChop 2.0.

FIG. 15. Several high affinity peptides deriving from reticulocalbin were identified as peptides predicted to be presented by HLA-A*0201 and A*0101.

DETAILED DESCRIPTION OF THE INVENTION

Figure 1:
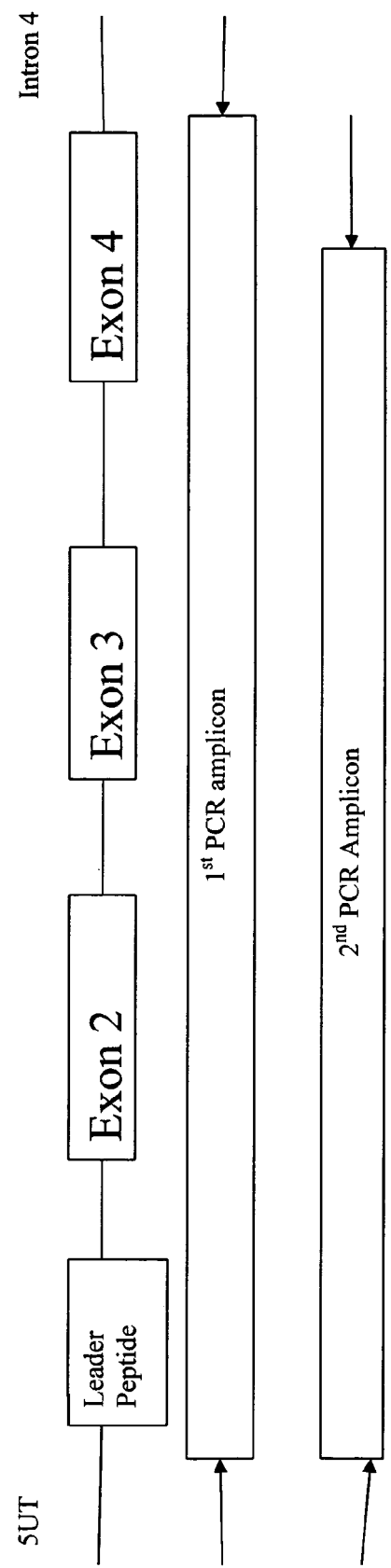
FIG. 1. Overview of 2 stage PCR strategy to amplify a truncated version of the human class I MHC.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

The present invention generally relates to a method of epitope discovery and comparative ligand mapping as well as methods of distinguishing infected/tumor cells from uninfected/non-tumor cells. The present method broadly includes the following steps: (1) providing a cell line containing a construct that encodes an individual soluble class I or class II MHC molecule (wherein the cell line is capable of naturally processing self or nonself proteins into peptide ligands capable of being loaded into the antigen binding grooves of the class I or class II MHC molecules); (2) culturing the cell line under conditions which allow for expression of the individual soluble class I or class II MHC molecule from the construct, with such conditions also allowing for the endogenous loading of a peptide ligand (from the self or non-self processed protein) into the antigen binding groove of each individual soluble class I or class II MHC molecule prior to secretion of the soluble class I or class II MHC molecules having the peptide ligands bound thereto; and (4) separating the peptide ligands from the individual soluble class I or class II MHC molecules.

The methods of the present invention may, in one embodiment, utilize a method of producing MHC molecules (from genomic DNA or cDNA) that are secreted from mammalian cells in a bioreactor unit. Substantial quantities of individual MHC molecules are obtained by modifying class I or class II MHC molecules so that they are capable of being secreted, isolated, and purified. Secretion of soluble MHC molecules overcomes the disadvantages and defects of the prior art in relation to the quantity and purity of MHC molecules produced. Problems of quantity are overcome because the cells producing the MHC do not need to be detergent lysed or killed in order to obtain the MHC molecule. In this way the cells producing secreted MHC remain alive and therefore continue to produce MHC. Problems of purity are overcome because the only MHC molecule secreted from the cell is the one that has specifically been constructed to be secreted. Thus, transfection of vectors encoding such secreted MHC molecules into cells which may express endogenous, surface bound MHC provides a method of obtaining a highly concentrated form of the transfected MHC molecule as it is secreted from the cells. Greater purity is assured by transfecting the secreted MHC molecule into MHC deficient cell lines.

Production of the MHC molecules in a hollow fiber bioreactor unit allows cells to be cultured at a density substantially greater than conventional liquid phase tissue culture permits. Dense culturing of cells secreting MHC molecules further amplifies the ability to continuously harvest the transfected MHC molecules. Dense bioreactor cultures of MHC secreting cell lines allow for high concentrations of individual MHC proteins to be obtained. Highly concentrated individual MHC proteins provide an advantage in that most downstream protein purification strategies perform better as the concentration of the protein to be purified increases. Thus, the culturing of MHC secreting cells in bioreactors allows for a continuous production of individual MHC proteins in a concentrated form.

The method of producing MHC molecules utilized in the present invention begins by obtaining genomic or complementary DNA which encodes the desired MHC class I or class II molecule. Alleles at the locus which encode the desired MHC molecule are PCR amplified in a locus specific manner. These locus specific PCR products may include the entire coding region of the MHC molecule or a portion thereof. In one embodiment a nested or hemi-nested PCR is applied to produce a truncated form of the class I or class II gene so that it will be secreted rather than anchored to the cell surface. In another embodiment the PCR will directly truncate the MHC molecule.

Locus specific PCR products are cloned into a mammalian expression vector and screened with a variety of methods to identify a clone encoding the desired MHC molecule. The cloned MHC molecules are DNA sequenced to insure fidelity of the PCR. Faithful truncated clones of the desired MHC molecule are then transfected into a mammalian cell line. When such cell line is transfected with a vector encoding a recombinant class I molecule, such cell line may either lack endogenous class I MHC molecule expression or express endogenous class I MHC molecules. One of ordinary skill of the art would note the importance, given the present invention, that cells expressing endogenous class I MHC molecules may spontaneously release MHC into solution upon natural cell death. In cases where this small amount of spontaneously released MHC is a concern, the transfected class I MHC molecule can be "tagged" such that it can be specifically purified away from spontaneously released endogenous class I molecules in cells that express class I molecules. For example, a DNA fragment encoding a HIS tail may be attached to the protein by the PCR reaction or may be encoded by the vector into which the PCR fragment is cloned, and such HIS tail, therefore, further aids in the purification of the class I MHC molecules away from endogenous class I molecules. Tags beside a histidine tail have also been demonstrated to work, and one of ordinary skill in the art of tagging proteins for downstream purification would appreciate and know how to tag a MHC molecule in such a manner so as to increase the ease by which the MHC molecule may be purified.

Cloned genomic DNA fragments contain both exons and introns as well as other non-translated regions at the 5' and 3' termini of the gene. Following transfection into a cell line which transcribes the genomic DNA (gDNA) into RNA, cloned genomic DNA results in a protein product thereby removing introns and splicing the RNA to form messenger RNA (mRNA), which is then translated into an MHC protein. Transfection of MHC molecules encoded by gDNA therefore facilitates reisolation of the gDNA, mRNA/cDNA, and protein. Production of MHC molecules in non-mammalian cell lines such as insect and bacterial cells requires cDNA clones, as these lower cell types do not have the ability to splice introns out of RNA transcribed from a gDNA clone. In these instances the mammalian gDNA transfectants of the present invention provide a valuable source of RNA which can be reverse transcribed to form MHC cDNA. The cDNA can then be cloned, transferred into cells, and then translated into protein. In addition to producing secreted MHC, such gDNA transfectants therefore provide a ready source of mRNA, and therefore cDNA clones, which can then be transfected into non-mammalian cells for production of MHC. Thus, the present invention which starts with MHC genomic DNA clones allows for the production of MHC in cells from various species.

A key advantage of starting from gDNA is that viable cells containing the MHC molecule of interest are not needed. Since all individuals in the population have a different MHC repertoire, one would need to search more than 500,000 individuals to find someone with the same MHC complement as a desired individual—such a practical example of this principle is observed when trying to find a donor to match a recipient for bone marrow transplantation. Thus, if it is desired to produce a particular MHC molecule for use in an experiment or diagnostic, a person or cell expressing the MHC allele of interest would first need to be identified. Alternatively, in the method of the present invention, only a saliva sample, a hair root, an old freezer sample, or less than a milliliter (0.2 ml) of blood would be required to isolate the gDNA. Then, starting from gDNA, the MHC molecule of interest could be obtained via a gDNA clone as described herein, and following transfection of such clone into mammalian cells, the desired protein could be produced directly in mammalian cells or from cDNA in several species of cells using the methods of the present invention described herein.

Current experiments to obtain an MHC allele for protein expression typically start from mRNA, which requires a fresh sample of mammalian cells that express the MHC molecule of interest. Working from gDNA does not require gene expression or a fresh biological sample. It is also important to note that RNA is inherently unstable and is not as easily obtained as is gDNA. Therefore, if production of a particular MHC molecule starting from a cDNA clone is desired, a person or cell line that is expressing the allele of interest must traditionally first be identified in order to obtain RNA. Then a fresh sample of blood or cells must be obtained; experiments using the methodology of the present invention show that $\geq 5$ milliliters of blood that is less than 3 days old is required to obtain sufficient RNA for MHC cDNA synthesis. Thus, by starting with gDNA, the breadth of MHC molecules that can be readily produced is expanded. This is a key factor in a system as polymorphic as the MHC system; hundreds of MHC molecules exist, and not all MHC molecules are readily available. This is especially true of MHC molecules unique to isolated populations or of MHC molecules unique to ethnic minorities. Starting class I or class II MHC molecule expression from the point of genomic DNA simplifies the isolation of the gene of interest and insures a more equitable means of producing MHC molecules for study; otherwise, one would be left to determine whose MHC molecules are chosen and not chosen for study, as well as to determine which ethnic population from which fresh samples cannot be obtained and therefore should not have their MHC molecules included in a diagnostic assay.

While cDNA may be substituted for genomic DNA as the starting material, production of cDNA for each of the desired HLA class I types will require hundreds of different, HLA typed, viable cell lines, each expressing a different HLA class I type. Alternatively, fresh samples are required from individuals with the various desired MHC types. The use of genomic DNA as the starting material allows for the production of clones for many HLA molecules from a single genomic DNA sequence, as the amplification process can be manipulated to mimic recombinatorial and gene conversion events. Several mutagenesis strategies exist whereby a given class I gDNA clone could be modified at either the level of gDNA or at the cDNA resulting from this gDNA clone. The process of producing MHC molecules utilized in the present invention does not require viable cells, and therefore the degradation which plagues RNA is not a problem.

The soluble class I MHC proteins produced by the method described herein is utilized in the methods of epitope discovery and comparative ligand mapping of the present invention. The methods of epitope discovery and comparative ligand mapping described herein which utilize secreted individual MHC molecules have several advantages over the prior art, which utilized MHC from cells expressing multiple membrane-bound MHCs. While the prior art method could distinguish if an epitope was presented on the surface of a cell, this prior art method is unable to directly distinguish in which specific MHC molecule the peptide epitope was bound. Lengthy purification processes might be used to try and obtain a single MHC molecule, but doing so limits the quantity and usefulness of the protein obtained. The novelty and flexibility of the current invention is that individual MHC specificities can be utilized in sufficient quantity through the use of recombinant, soluble MHC proteins.

Class I and class II MHC molecules are really a trimolecular complex consisting of an alpha chain, a beta chain, and the alpha/beta chain's peptide cargo (i.e. peptide ligand) which is presented on the cell surface to immune effector cells. Since it is the peptide cargo, and not the MHC alpha and beta chains, which marks a cell as infected, tumorigenic, or diseased, there is a great need to identify and characterize the peptide ligands bound by particular MHC molecules. For example, characterization of such peptide ligands greatly aids in determining how the peptides presented by a person with MHC-associated diabetes differ from the peptides presented by the MHC molecules associated with resistance to diabetes. As stated above, having a sufficient supply of an individual MHC molecule, and therefore that MHC molecule's bound peptides, provides a means for studying such diseases. Because the method of the present invention provides quantities of MHC protein previously unobtainable, unparalleled studies of MHC molecules and their important peptide cargo can now be facilitated.

Therefore, the present invention is also related to methods of epitope discovery and comparative ligand mapping which can be utilized to distinguish infected/tumor cells from uninfected/non-tumor cells by unique epitopes presented by MHC molecules in the disease or non-disease state.

Creation of sHLA Molecules from Genomic DNA (gDNA)

1. Genomic DNA Extraction. 200 μl of sample either blood, plasma, serum, buffy coat, body fluid or up to $5 \times 10^6$ lymphocytes in 200 μl Phosphate buffered saline were used to extract genomic DNA using the QIAamp® DNA Blood Mini Kit blood and body fluid spin protocol. Genomic DNA quality and quantity was assessed using optical density readings at 260 nm and 280 nm.

2.1 PCR Strategy. Primers were designed for HLA-A, -B and -C loci in order to amplify a truncated version of the human class I MHC using a 2 stage PCR strategy. The first stage PCR uses a primer set that amplify from the 5' Untranslated region to Intron 4. This amplicon is used as a template for the second PCR which results in a truncated version of the MHC Class I gene by utilizing a 3' primer that sits down in exon 4, the 5' primer remains the same as the $1^{st}$ PCR. An overview can be seen in FIG. 1. The primers for each locus are listed in TABLE I. Different HLA-B locus alleles require primers with different restriction cut sites depending on the nucleotide sequence of the allele. Hence there are two 5' and two 3' truncating primers for the -B locus.

TABLE I

| Primer name | Sequence 5'-3' | Locus | Cut site | Annealing site | Seq. ID NO. |
|---|---|---|---|---|---|
| PP5UTA | GCGCTCTAGACCCAGACGCCGAGGATGGCC | A | XbaI | 5UT | 1 |
| 3PPI4A | GCCCTGACCCTGCTAAAGGT | A | | Intron 4 | 2 |
| PP5UTB | GCGCTCTAGACCACCCGGACTCAGAATCTCCT | B | XbaI | 5UT | 3 |
| 3PPI4B | TGCTTTCCCTGAGAAGAGAT | B | | Intron 4 | 4 |
| 5UTB39 | AGGCGAATTCCAGAGTCTCCTCAGACGCG | B*39 | EcoRI | 5UT B39 | 5 |
| 5PKCE | GGGCGAATTCCCGCCGCCACCATGCGGGTCATGGCGCC | C | EcoRI | 5UT | 6 |
| 3PPI4C | TTCTGCTTTCCTGAGAAGAC | C | | Intron 4 | 7 |
| PP5UT | GGGCGAATTCGGACTCAGAATCTCCCCAGACGCCGAG | B | EcoRI | 5UT | 8 |
| PP3PEI | CCGCGAATTCTCATCTCAGGGTGAGGGGCT | A, B, C | EcoRI | Exon 4 | 9 |
| PP3PEIH | CCGCAAGCTTTCATCTCAGGGTGAGGGGCT | A, B, C | HindIII | Exon 4 | 10 |
| 3PEIHC7 | CCGCAAGCTTTCAGCTCAGGGTGAGGGGCT | Cw*07 | HindIII | Exon 4 | 11 |

2.2 Primary PCR. Materials: An Eppendorf Gradient Mastercycler is used for all PCR. (1) H$_2$O:Dionized ultrafiltered water (DIUF) Fisher Scientific, W2-4,41. (2) PCR nucleotide mix (10 mM each deoxyribonucleoside triphosphate [dNTP]), Boehringer Manheim, #1814, 362. (3) 10× Pfx Amplification buffer, pH 9.0, GibcoBRL®, part # 52806, formulation is proprietary information. (4) 50 mM MgSO$_4$, GibcoBRL®, part #52044. (5) Platinum® Pfx DNA Polymerase (B Locus only), GibcoBRL®, 11708-013. (6) Pfu DNA Polymerase (A and C Locus), Promega, M7741. (7) Pfu DNA Polymerase 10× reaction Buffer with MgSO$_4$, 200 mM Tris-HCL, pH 8.8,100 mM KCl, 100 mM (NH$_4$)$_2$SO$_4$, 20 mM MgSO$_4$, 1 mg/ml nuclease free BSA, 1% Triton®X-100. (8) Amplification primers (in ng/µl) (see TABLE I): A locus: 5' sense PP5UTA (300); 3' antisense PPI4A (300); B locus (Not B*39's): sense PP5UTB (300); antisense PPI4B (300); B locus (B*39's): sense 5UTB39 (300); antisense PPI4B (300); C Locus: sense 5PKCE (300); antisense PPI4C (300). (9) gDNA Template.

2.3 Secondary PCR (also used for colony PCR). (1) H$_2$O: Dionized ultrafiltered water (DIUF) Fisher Scientific, W2-4, 41. (2) PCR nucleotide mix (10 mM each deoxyribonucleoside triphosphate [dNTP]), Boehringer Manheim, #1814, 362. (3) Pfu DNA Polymerase (A and C Locus), Promega, M7741. (4) Pfu DNA Polymerase 10× reaction Buffer with MgSO$_4$, 200 mM Tris-HCL, pH 8.8,100 mM KCl, 100 mM (NH$_4$)$_2$SO$_4$, 20 mM MgSO$_4$, 1 mg/ml nuclease free BSA, 1% Triton®X-100. (5) Amplification primers (in ng/µl) see TABLE I: A-locus: 5' sense PP5UTA (300), 3' antisense PP3PEI (300); B-locus: sense PP5UTB (300), antisense PP3PEI (300); B-locus: sense PP5UT (300), antisense PP3PEIH (300); B-locus B39's: sense 5UTB39 (300), antisense PP3PEIH (300); C-locus: sense 5PKCE (300), antisense PP3PEI (300); C-locus Cw*7's: sense 5PKCE (300), antisense 3PEIHC7 (300). (6) Template 1:100 dilution of the primary PCR product.

2.4 Gel Purification of PCR products and vectors. (1) Dark Reader Tansilluminator Model DR-45M, Clare Chemical Research. (2) SYBR Green, Molecular Probes Inc. (3) Quantum Prep Freeze 'N Squeeze DNA Gel Rxtraction Spin Columns, Bio-Rad Laboratories, 732-6165.

2.5 Restriction digests, Ligation and Transformation. (1) Restriction enzymes from New England Biolabs: (a) EcoR I #R0101S; (b) Hind III #R0104S; (c) Xba I #R0145S. (2) T4 DNA Ligase, New England Biolabs, #M0202S. (3) pcDNA3.1(−), Invitrogen Corporation, V795-20. (4) 10× Buffers from New England Biolabs: (a) EcoR I buffer, 500 mM NaCl, 1000 mM Tris-HCL, 10 mM MgCL$_2$, 0.25% Triton-X 100, pH 7.5; (b) T4 DNA ligase buffer, 500 mM Tris-HCL, 100 mM MgCL$_2$, 100 mM DTT, 10 mM ATP, 250 ug/ml BSA, pH 7.5; (c) NEB buffer 2, 500 mM NaCl, 100 mM Tris-HCl, 100 mM MgCl$_2$, 10 mM DDT, pH 7.9. (5) 100× BSA, New England Biolabs. (6) Z-Competent E. coli Transformation Buffer Set, Zymo Research, T3002. (7) E. coli strain JM109. (8) LB Plates with 100 µg/ml ampicillin. (9) LB media with 100 µg/ml ampicillin.

2.6 Plasmid Extraction. Wizard Plus SV minipreps, Promega, #A1460.

2.7 Sequencing of Clones. (1) Thermo Sequenase Primer Cycle Sequencing Kit, Amersham Pharmacia Biotech, 25-2538-01. (2) CY5 labelled primers (see TABLE II). (3) AlfExpress automated DNA sequencer, Amersham Pharmacia Biotech.

TABLE II

| Primer Name | Sequence 5'-3' | Seq. ID NO: |
|---|---|---|
| T7Prom | TAATACGACTCACTATAGGG | 12 |
| BGHrev | TAGAAGGCACAGTCGAGG | 13 |
| PPI2E2R | GTCGTGACCTGCGCCCC | 14 |
| PPI2E2F | TTTCATTTTCAGTTTAGGCCA | 15 |
| ABCI3E4F | GGTGTCCTGTCCATTCTCA | 16 |

2.8 Gel Casting. (1) PagePlus 40% concentrate, Amresco, E562, 500 ml. (2) Urea, Amersham Pharmacia Biotech, 17-0889-01,500g. (3) 3 N'N'N'N'-tetramethylethyleneiamine (TEMED), APB. (4) Ammonium persulphate (10% solution), APB. (5) Boric acid, APB. (6) EDTA-disodium salt, APB. (7) Tris, APB. (8) Bind-Saline, APB. (9) Isopropanol, Sigma. (10) Glacial Acetic Acid, Fisher Biotech. (11) DIUF water, Fisher Scientific. (12) EtOH 200-proof.

2.9 Plasmid Preparation for Electroporation. Qiagen Plasmid Midi kit, Qiagen Inc., 12143.

3.0 Electroporation. (1) Biorad Gene Pulser with capacitance extender, Bio-Rad Laboratories. (2) Gene Pulser Cuvette, Bio-Rad Laboratories. (3) Cytomix: 120 mM KCl, 0.15 mM $CaCl_2$, 10 mM $K_2HPO_4$/$KH_2PO_4$, pH 7.6, 25 mM Hepes, pH 7.6, 2 mM EGTA, pH 7.6, 5 mM $MgCl_2$, pH 7.6 with KOH. (4) RPMI 1640+20% Foetal Calf Serum+Pen/strep. (5) Haemacytometer. (6) Light Microscope. (7) $CO_2$ 37° Incubator. (8) Cells in log phase.

Primary PCR

| A-Locus and C-Locus | |
|---|---|
| 10× Pfu buffer | 5 μl |
| 5' Primer (300 ng/μl) | 1 μl |
| 3' Primer (300 ng/μl) | 1 μl |
| dNTP's (10 mM each) | 1 μl |
| gDNA (50 ng/μl) | 10 μl |
| DIUF $H_2O$ | 31.4 μl |
| Pfu DNA Polymerase | 0.6 μl |
| 96° C. 2 min. | |
| 95° C. 1 min | |
| 58° C. 1 min | ×35 |
| 73° C. 5 min | |
| 73° C. 10 min | |

| B-locus | |
|---|---|
| 10× Pfx buffer | 5 μl |
| 5' Primer (300 ng/μl) | 1 μl |
| 3' Primer (300 ng/μl) | 1 μl |
| dNTP's (10 mM each) | 1.5 μl |
| $MgSO_4$ (50 mM) | 1 μl |
| gDNA (100 ng/μl) | 1 μl |
| DIUF $H_2O$ | 40 μl |
| Pfx DNA Polymerase | 0.5 μl |
| 94° C. 2 min. | |
| 94° C. 1 min | |
| 60° C. 1 min | ×35 |
| 68° C. 3.5 min | |
| 68° C. 5 min | |

Gel Purification of PCR (all PCR and Plasmids are Gel Purified)

Mix primary PCR with 5 μl of 1× SYBR green and incubate at room temperature for 15 minutes then load on a 1% agarose gel. Visualize on the Dark Reader and purify using the Quantum Prep Freeze and Squeeze extraction kit according to the manufacturers instructions.

Secondary PCR

| A, B and C Loci | |
|---|---|
| 10× Pfu buffer | 5 μl |
| 5' Primer (300 ng/μl) | 0.5 μl |
| 3' Primer (300 ng/μl) | 0.5 μl |
| dNTP's (10 mM each) | 1 μl |
| 1:100 1° PCR | 10 μl |
| DIUF $H_2O$ | 37.5 μl |
| Pfu DNA Polymerase | 0.5 μl |
| 96° C. 2 min. | |
| 95° C. 1 min | |
| 58° C. 1 min | ×35 |
| 73° C. 4 min | |
| 73° C. 7 min | |

Restriction digests

| | |
|---|---|
| 2° PCR (gel purified) | 30 μl |
| Restriction enzyme 1 | × μl |
| Restriction enzyme 2 | × μl |
| 10× buffer | 5 μl |
| 100× BSA | 0.5 μl |
| DIUF $H_2O$ | 10.5 μl |

The enzymes used will be determined by the cut sites incorporated into the PCR primers for each individual PCR. The expression vector pcDNA3.1 (−) will be cut in a similar manner.

Ligation

| | |
|---|---|
| PcDNA3.1(−) cut with same enzymes as PCR | 50 ng |
| Cut PCR | 100 ng |
| 10× T4 DNA ligase buffer | 2 μl |
| T4 DNA Ligase | 1 μl |
| DIUF $H_2O$ | up to 20 μl |

Transformation

Transform JM109 using competent cells made using Z-competent *E. coli* Transformation Kit and Buffer Set and follow the manufacturers instructions.

Colony PCR

This will check for insert in any transformed cells. Follow the same protocol for the secondary PCR.

Mini Preps of Colonies with Insert

Use the Wizard Plus SV minipreps and follow the manufacturers instructions. Make glycerol stocks before beginning extraction protocol.

Sequencing of Positive Clones

Using the Thermo Sequenase Primer Cycle Sequencing Kit

| | |
|---|---|
| A, C, G or T mix | 3 μl |
| CY5 Primer 1 pm/μl | 1 μl |
| DNA template 100 ng/μl | 5 μl |
| 96° C. 2 min | |
| 96° C. 30 sec | ×25 |
| 61° C. 30 sec | |

Add 6 μl formamide loading buffer and load 10 μl onto sequencing gel. Analyse sequence for good clones with no misincorporations.

Midi Preps

Prepare plasmid for electroporation using the Qiagen Plasmid Midi Kit according to the manufacturers instructions.

Electroporation

Electroporations are performed as described in "The Bw4 public epitope of HLA-B molecules confers reactivity with natural killer cell clones that express NKb1, a putative HLA receptor. Gumperz, J. E., V. Litwin, J.H. Phillips, L. L. Lanier and P. Parham. J. Exp. Med. 181:1133-1144, 1995, which is expressly incorporated herein by reference."

Screening for Production of Soluble HLA

An ELISA is used to screen for the production of soluble HLA. For biochemical analysis, monomorphic monoclonal antibodies are particularly useful for identification of HLA locus products and their subtypes.

W6/32 is one of the most common monoclonal antibodies (mAb) used to characterize human class I major histocompatibility complex (MHC) molecules. It is directed against monomorphic determinants on HLA-A, -B and -C HCs, which recognizes only mature complexed class I molecules and recognizes a conformational epitope on the intact MHC molecule containing both beta2-microglobulin (β2m) and the heavy chain (HC). W6/32 binds a compact epitope on the class I molecule that includes both residue 3 of beta2m and residue 121 of the heavy chain (Ladasky JJ, Shum BP, Canavez F, Seuanez H N, Parham P. Residue 3 of beta2-microglobulin affects binding of class I MHC molecules by the W6/32 antibody. Immunogenetics April 1999;49(4):312-20.). The constant portion of the molecule W6/32 binds to is recognized by CTLs and thus can inhibit cytotoxicity. The reactivity of W6/32 is sensitive to the amino terminus of human beta2-microglobulin (Shields M J, Ribaudo R K. Mapping of the monoclonal antibody W6/32: sensitivity to the amino terminus of beta2-microglobulin. Tissue Antigens May, 1998;51(5):567-70). HLA-C could not be clearly identified in immunoprecipitations with W6/32 suggesting that HLA-C locus products may be associated only weakly with b2m, explaining some of the difficulties encountered in biochemical studies of HLA-C antigens [Stam, 1986 #1]. The polypeptides correlating with the C-locus products are recognized far better by HC-10 than by W6/32 which confirms that at least some of the C products may be associated with b2m more weakly than HLA-A and -B. W6/32 is available biotinylated (Serotec MCA81B) offering additional variations in ELISA procedures.

HC-10 is reactive with almost all HLA-B locus free heavy chains. The A2 heavy chains are only very weakly recognized by HC-10. Moreover, HC-10 reacts only with a few HLA-A locus heavy chains. In addition, HC-10 seems to react well with free heavy chains of HLA-C types. No evidence for reactivity of HC-10 with heavy-chain/b2m complex has been obtained. None of the immunoprecipitates obtained with HC-10 contained b2m [Stam, 1986 #1]. This indicates that HC-10 is directed against a site of the HLA class I heavy chain that includes the portion involved in interaction with the β2m. The pattern of HC-10 precipitated material is qualitatively different from that isolated with W6/32.

TP25.99 detects a determinant in the alpha3 domain of HLA-ABC. It is found on denatured HLA-B (in Western) as well as partially or fully folded HLA-A,B,& C. It doesn't require a peptide or β2m, i.e. it works with the alpha 3 domain which folds without peptide. This makes it useful for HC determination.

Anti-human β2m (HRP) (DAKO P0174) recognizes denatured as well as complexed β2m. Although in principle anti-β2m reagents could be used for the purpose of identification of HLA molecules, they are less suitable when association of heavy chain and β2m is weak. The patterns of class I molecules precipitated with W6/32 and anti-β2m are usually indistinguishable [Vasilov, 1983 #10].

Rabbit anti-β2-microglobulin dissociates β2-microglobulin from heavy chain as a consequence of binding (Rogers, M. J., Appella, E., Pierotti, M. A., Invernizzi, G., and Parmiani, G. (1979) Proc Natl. Acad. Sci. U.S.A. 76, 1415-1419). It also has been reported that rabbit anti-human β2-microglobulin dissociactes β2-microglobulin from HLA heavy chains upon binding (Nakamuro, K., Tanigaki, N., and Pressman, D. (1977) Immunology 32, 139-146.). This anti-human β2m antibody is also available unconjugated (DAKO A0072).

The W6/32-HLA sandwich ELISA. Sandwich assays can be used to study a number of aspects of protein complexes. If antibodies are available to different components of a heteropolymer, a two-antibody assay can be designed to test for the presence of the complex. Using a variation of these assays, monoclonal antibodies can be used to test whether a given antigen is multimeric. If the same monoclonal antibody is used for both the solid phase and the label, monomeric antigens cannot be detected. Such combinations, however, may detect multimeric forms of the antigen. In these assays negative results may be generated both by multimeric antigen held in unfavorable steric positions as well as by monomeric antigens.

The W6/32—anti-β2m antibody sandwich assay is one of the best techniques for determining the presence and quantity of sHLA. Two antibody sandwich assays are quick and accurate, and if a source of pure antigen is available, the assay can be used to determine the absolute amounts of antigen in unknown samples. The assay requires two antibodies that bind to non-overlapping epitopes on the antigen. This assay is particularly useful to study a number of aspects of protein complexes.

To detect the antigen (sHLA), the wells of microtiter plates are coated with the specific (capture) antibody W6/32 followed by the incubation with test solutions containing antigen. Unbound antigen is washed out and a different antigen-specific antibody (anti-β2m) conjugated to HRP is added, followed by another incubation. Unbound conjugate is washed out and substrate is added. After another incubation, the degree of substrate hydrolysis is measured. The amount of substrate hydrolyzed is proportional to the amount of antigen in the test solution.

The major advantages of this technique are that the antigen does not need to be purified prior to use and that the assays are very specific. The sensitivity of the assay depends on 4 factors: (1) The number of capture antibody; (2) The avidity of the capture antibody for the antigen; (3) The avidity of the second antibody for the antigen; (4) The specific activity of the labeled second antibody.

Using an ELISA protocol template and label a clear 96-well polystyrene assay plate. Polystyrene is normally used as a microtiter plate. (Because it is not translucent, enzyme assays that will be quantitated by a plate reader should be performed in polystyrene and not PVC plates).

Coating of the W6/32 is performed in Tris buffered saline (TBS); pH 8.5 A coating solution of 8.0 µg/ml of specific W6/32 antibody in TBS (pH 8.5) is prepared. (blue tube preparation stored at −20° C. with a concentration of 0.2 mg/ml and a volume of 1 ml giving 0.2 mg per tube).

TABLE III

| No. of plates | Total Volume | W6/32 antibody | TBS pH 8.5 |
| --- | --- | --- | --- |
| 1 | 10 ml | 400 µl | 9.6 ml |
| 2 | 20 ml | 800 µl | 19.2 ml |
| 3 | 30 ml | 1200 µl | 28.8 ml |
| 4 | 40 ml | 1600 µl | 38.4 ml |
| 5 | 50 ml | 2000 µl | 48.0 ml |

Although this is well above the capacity of a microtiter plate, the binding will occur more rapidly. Higher concentrations will speed the binding of antigen to the polystyrene but the capacity of the plastic is only about 100 ng/well (300 ng/cm$_2$), so the extra protein will not bind. (If using W6/32 of unknown composition or concentration, first titrate the amount of standard antibody solution needed to coat the plate versus a fixed, high concentration of labeled antigen. Plot the values and select the lowest level that will yield a strong signal. Do not include sodium azide in any solutions when horseradish peroxidase is used for detection.

Immediately coat the microtiter plate with 100 µl of antigen solution per well using a multichannel pipet. Standard polystyrene will bind antibodies or antigens when the proteins are simply incubated with the plastic. The bonds that hold the proteins are non-covalent, but the exact types of interactions are not known. Shake the plate to ensure that the antigen solution is evenly distributed over the bottom of each well. Seal the plate with plate sealers (sealplate adhesive sealing film, nonsterile, 100 per unit; Phenix; LMT-Seal-EX) or sealing tape to Nunc-Immuno™ Modules (# 236366). Incubate at 4° C. overnight. Avoid detergents and extraneous proteins. Next day, remove the contents of the well by flicking the liquid into the sink or a suitable waste container. Remove last traces of solution by inverting the plate and blotting it against clean paper toweling. Complete removal of liquid at each step is essential for good performance.

Wash the plate 10 times with Wash Buffer (PBS containing 0.05% Tween-20) using a multi-channel ELISA washer. After the last wash, remove any remaining Wash Buffer by inverting the plate and blotting it against clean paper toweling. After the W6/32 is bound, the remaining sites on the plate must be saturated by incubating with blocking buffer made of 3% BSA in PBS. Fill the wells with 200 µl blocking buffer. Cover the plates with an adhesive strip and incubate overnight at 4° C. Alternatively, incubate for at least 2 hours at room temperature which is, however, not the standard procedure. Blocked plates may be stored for at least 5 days at 4° C. Good pipetting practice is most important to produce reliable quantitative results. The tips are just as important a part of the system as the pipette itself. If they are of inferior quality or do not fit exactly, even the best pipette cannot produce satisfactory results. The pipette working position is always vertical: Otherwise causing too much liquid to be drawn in. The immersion depth should be only a few millimeters. Allow the pipetting button to retract gradually, observing the filling operation. There should be no turbulence developed in the tip, otherwise there is a risk of aerosols being formed and gases coming out of solution.

When maximum levels of accuracy are stipulated, prewetting should be used at all times. To do this, the required set volume is first drawn in one or two times using the same tip and then returned. Prewetting is absolutely necessary on the more difficult liquids such as 3% BSA. Do not prewet, if your intention is to mix your pipetted sample thoroughly with an already present solution. However, prewet only for volumes greater than 10 µl. In the case of pipettes for volumes less than 10 µl the residual liquid film is as a rule taken into account when designing and adjusting the instrument. The tips must be changed between each individual sample. With volumes <10 µl special attention must also be paid to drawing in the liquid slowly, otherwise the sample will be significantly warmed up by the frictional heat generated. Then slowly withdraw the tip from the liquid, if necessary wiping off any drops clinging to the outside.

To dispense the set volume hold the tip at a slight angle, press it down uniformly as far as the first stop. In order to reduce the effects of surface tension, the tip should be in contact with the side of the container when the liquid is dispensed. After liquid has been discharged with the metering stroke, a short pause is made to enable the liquid running down the inside of the tip to collect at its lower end. Then press it down swiftly to the second stop, in order to blow out the tip with the extended stroke with which the residual liquid can be blown out. In cases that are not problematic (e.g. aqueous solutions) this brings about a rapid and virtually complete discharge of the set volume. In more difficult cases, a slower discharge and a longer pause before actuating the extended stroke can help. To determine the absolute amount of antigen (sHLA), sample values are compared with those obtained using known amounts of pure unlabeled antigen in a standard curve.

For accurate quantitation, all samples have to be run in triplicate, and the standard antigen-dilution series should be included on each plate. Pipetting should be preformed without delay to minimize differences in time of incubation between samples. All dilutions should be done in blocking buffer. Thus, prepare a standard antigen-dilution series by successive dilutions of the homologous antigen stock in 3% BSA in PBS blocking buffer. In order to measure the amount of antigen in a test sample, the standard antigen-dilution series needs to span most of the dynamic range of binding. This range spans from 5 to 100 ng sHLA/ml. A stock solution Ê of 1 µg/ml should be prepared, aliquoted in volumes of 300 µl and stored at 4° C. Prepare a 50 ml batch of standard at the time. (New batches need to be compared to the old batch before used in quantitation).

Use a tube of the standard stock solution Ê to prepare successive dilutions. While standard curves are necessary to accurately measure the amount of antigen in test samples, they are unnecessary for qualitative "yes/no" answers. For accurate quantitation, the test solutions containing sHLA should be assayed over a number of at least 4 dilutions to assure to be within the range of the standard curve. Prepare serial dilutions of each antigen test solution in blocking buffer (3% BSA in PBS). After mixing, prepare all dilutions in disposable U-bottom 96 well microtiter plates before adding them to the W6/32-coated plates with a multipipette. Add 150 µl in each well. To further proceed, remove any remaining blocking buffer and wash the plate as described above. The plates are now ready for sample addition. Add 100 µl of the sHLA containing test solutions and the standard antigen dilutions to the antibody-coated wells.

Cover the plates with an adhesive strip and incubate for exactly 1 hour at room temperature. After incubation, remove the unbound antigen by washing the plate 10× with Wash Buffer (PBS containing 0.05% Tween-20) as described. Prepare the appropriate developing reagent to detect sHLA. Use the second specific antibody, anti-human β2m-HRP (DAKO P0174/0.4 mg/ml) conjugated to Horseradish Peroxidase (HRP). Dilute the anti-human β2m-HRP in a ratio of 1:1000 in 3% BSA in PBS. (Do not include sodium azide in solutions when horseradish peroxidase is used for detection).

TABLE IV

| No. of plates | Total Volume | anti-β2m-HRP antibody | 3% BSA in PBS |
|---|---|---|---|
| 1 | 10 ml | 10 µl | 10 ml |
| 2 | 20 ml | 20 µl | 2 ml |
| 3 | 30 ml | 30 µl | 30 ml |
| 4 | 40 ml | 40 µl | 40 ml |
| 5 | 50 ml | 50 µl | 50 ml |

Add 100 µl of the secondary antibody dilution to each well. All dilutions should be done in blocking buffer. Cover with a new adhesive strip and incubate for 20 minutes at room temperature. Prepare the appropriate amount of substrate prior to the wash step. Bring the substrate to room temperature.

OPD (o-Phenylenediamine) is a peroxidase substrate suitable for use in ELISA procedures. The substrate produces a soluble end product that is yellow in color. The OPD reaction is stopped with 3 N $H_2SO_4$, producing an orange-brown product and read at 492 nm. Prepare OPD fresh from tablets (Sigma, P6787; 2 mg/tablet). The solid tablets are convenient to use when small quantities of the substrate are required. After second antibody incubation, remove the unbound secondary reagent by washing the plate 10× with Wash Buffer (PBS containing 0.05% Tween-20). After the final wash, add 100 µl of the OPD substrate solution to each well and allow to develop at room temperature for 10 minutes. Reagents of the developing system are light-sensitive, thus, avoid placing the plate in direct light. Prepare the 3 N $H_2SO_4$ stop solution. After 10 minutes, add 100 µl of stop solution per 100 µl of reaction mixture to each well. Gently tap the plate to ensure thorough mixing.

Read the ELISA plate at a wavelength of 490 nm within a time period of 15 minutes after stopping the reaction. The background should be around 0.1. If your background is higher, you may have contaminated the substrate with a peroxidase. If the substrate background is low and the background in your assay is high, this may be due to insufficient blocking. Finally analyze your readings. Prepare a standard curve constructed from the data produced by serial dilutions of the standard antigen. To determine the absolute amount of antigen, compare these values with those obtained from the standard curve.

Creation of Transfectants and Production of Soluble Class I Molecules

Transfectants were established as previously described (Prilliman, KR et al., Immunogenetics 45:379, 1997, which is expressly incorporated herein by reference) with the following modifications: a cDNA clone of B*1501 containing the entire coding region of the molecule was PCR amplified in order to generate a construct devoid of the cytoplasmic domain using primers 5PXI (59-GGGCTCTAGAGGACTCAGAATCTCCCCAGAC GCCGAG-39; SEQ ID NO:19) and 3PEI (59-CCGCGAATTCTCATCTCAGGGTGAG-39; SEQ ID NO:52) as shown in TABLE V. Constructs were also created containing a C-terminal epitope tag consisting of either 6 consecutive histidines or the FLAG epitope (Asp-Tyr-Lys -Asp-Asp-Asp-Asp-Lys; SEQ ID NO:53). TABLE V Primers utilized to create B*1501-HIS and B*1501-FLAG were 5PXI and 3PEIHIS(59-CCGCGAATTCTCAGTG-GTGGTGGTGGTGGTGCCATCTCAGGGTGAG-39; SEQ ID NO: 26) or 3PEIFLAG (59-CCGCGAATTCT-CACTTGTCATCGTCGTCCTTG TAATCCCATCT-CAGGGTGAG-39; SEQ ID NO:27). PCR amplicons were purified using a Qiagen Spin PCR purification kit (Qiagen, Levsden, The Netherlands) and cloned into the mammalian expression vector pCDNA 3.1 (Invitrogen, Carlsbad, Calif., USA). TABLE V. After confirmation of insert integrity by bidirectional DNA sequencing, constructs were electroporated into the class I negative B-Iymphoblastoid cell line 721.221 (Prilliman, KR et al., 1997, previously incorporated herein by reference). Transfectants were maintained in medium containing G418 post-electroporation and subcloned in order to isolate efficient producers of soluble class I as determined by ELISA (Prilliman, KR et al, 1997, previously incorporated herein by reference).

TABLE V

| Primer name | Sequence | Full-length or Truncating | Notes | | Seq. ID NO: |
|---|---|---|---|---|---|
| HLA5UT | GGGCGTCGACGGACTCAGAATCTCCCCAGACGCCGAG | either | 5' primer, Sal I cut site | | 17 |
| 5UTA | GCGCGTCGACCCCAGACGCCGAGGATGGCC | either | 5' primer, Sal I cut site | A-locus specific | 18 |
| 5PXI | GGGCTCTAGAGGACTCAGAATCTCCCCAGACGCCGAG | either | 5' primer, Xba I cut site | | 19 |
| CLSP23 | CCGCGTCGACTCAGATTCTCCCCAGACGCCGAGATG | full-length | 5' primer, Sal I cut site | C-locus specific | 20 |
| LDC3UTA | CCGCAAGCTTAGAAACAAAGTCAGGGTT | full-length | 3' primer, HindIII cut site | A-locus specific | 21 |
| CLSP1085 | CCGCAAGCTTGGCAGCTGTCTCAGGCTTTACAAG(CT)G | full-length | 3' primer, HindIII cut site | C-locus specific | 22 |
| 3UTA | CCGCAAGCTTTTGGGGAGGGAGCACAGGTCAGCGTGGGAAG | full-length | 3' primer, HindIII cut site | A-locus specific | 23 |
| 3UTB | CCGCAAGCTTCTGGGGAGGAAACATAGGTCAGCATGGGAAC | full-length | 3' primer, HindIII cut site | B-locus specific | 24 |
| 3PEI | CCGCGAATTCTCATCTCAGGGTGAG | truncating | 3' primer, EcoRI cut site | | 25 |
| 3PEIHIS | CCGCGAATTCTCAGTGGTGGTGGTGGTGGTGCCATCTCAGGGTGAG | truncating | 3' primer, EcoRI cut site | adds hexa-histidine tail | 26 |
| 3PEIFLAG | CCGCGATTCTCACTTGTCATCGTCGTCCTTGTAATCCCATCTCAGGGTGAG | truncating | 3' primer, EcoRI cut site | adds FLAG-epitope | 27 |
| 5PKOZXB | GGGCTCTAGACCGCCGCCACCATGCGGGTCATGGCGCC | either | 5' primer, Xba I cut site | C-locus specific | 28 |

Soluble B*1501, B*1501-HIS, and B*1501-FLAG were produced by culturing established transfectants in CP3000 hollow-fiber bioreactors as previously described by Prilliman et al, 1997, which has previously been incorporated herein by reference. Supernatants containing soluble class I molecules were collected in bioreactor harvests and purified on W6/32 affinity columns. At least 2 column purifications were performed per molecule.

Ligand Purification, Edman Sequencing, and Reverse-phase HPLC Separation of Peptides Peptide ligands were purified from class I molecules by acid elution (Prilliman, K R et al., Immunogenetics 48:89, 1998 which is expressly incorporated herein by reference) and further separated from heavy and light chains by passage through a stirred cell (Millipore, Bedford, Mass., USA) equipped with a 3-Kd cutoff membrane (Millipore). Approximately $\frac{1}{100}$ volume of stirred cell flow through containing peptide eluted from either B*1501, B*1501-HIS, or B*1501-FLAG was subjected to 14 cycles of Edman degradation on a 492A pulsed liquid phase protein sequencer (Perkin-Elmer Applied Biosystems Division, Norwalk, Conn., USA) without the derivitization of cysteine. Edman motifs were derived by combining from multiple column elutions the picomolar yields of each amino acid and then calculating the fold increase over previous round as described in (Prilliman, K R et al, 1998, previously incorporated herein by reference) and are shown in FIG. 2.

Pooled peptide eluate was separated into fractions by RP-HPLC as previously described (Prilliman, K R et al, 1998, previously incorporated herein by reference). Briefly, 400-mg aliquots of peptides were dissolved in 100 ml of 10% acetic acid and loaded onto a 2.1 3 150 mm C18 column (Michrom Bioresources, Auburn, Calif., USA) using a gradient of 2%-10% acetonitrile with 0.06% TFA for 0.02 min followed by a 10%-60% gradient of the same for 60 min. Fractions were collected automatically at 1-min intervals with a flow rate of 180 ml/min.

Mass Spectrometric Ligand Analysis

RP-HPLC fractions were speed-vacuumed to dryness and reconstituted in 40 ml 50% methanol, 0.5% acetic acid. Approximately 6 ml from selected fractions were sprayed into an API-III triple quadrupole mass spectrometer (PE Sciex, Foster City, Calif., USA) using a NanoES ionization source inlet (Protana, Odense, Denmark). Scans were collected while using the following instrument settings: polarity—positive; needle voltage—1375 V; orifice voltage—65 V; N2 curtain gas—0.6 ml/min; step size—0.2 amu; dwell time—1.5 ms; and mass range—325-1400. Total ion traces generated from each molecule were compared visually in order to identify ions overlapping between molecules. Following identification of ion matches, individual ions were selected for MS/MS sequencing.

Sequences were predicted using the BioMultiView program (PE Sciex) algorithm predict sequence, and fragmentation patterns further assessed manually. Determinations of ion sequence homology to currently compiled sequences were performed using advanced BLAST searches against the nonredundant, human expressed sequence tag, and unfinished high throughput genomic sequences nucleotide databases currently available through the National Center for Biotechnology Information (National Institutes of Health, Bethesda, Md., USA).

The methodology of the present invention provides a direct comparative analysis of peptide ligands eluted from class I HLA molecules. In order to accomplish such comparative analyses, hollow-fiber bioreactors for class I ligand production were used along with reverse-phase HPLC for fractionating eluted ligands, and mass spectrometry for the mapping and sequencing of peptide ligands. The application of comparative ligand mapping also is applicable to cell lines that express endogenous class I. Prior to peptide sequence determination in class I positive cell lines, the effects of adding a C-terminal epitope tag to transfected class I molecules was found to have no deleterious effects. Either a tag consisting of 6 histidines (6-HIS) or a tag containing the epitope Asp-Tyr-Lys-Asp-Asp-Asp-Asp-Lys (FLAG; SEQ ID NO:53) was added to the C-terminus of soluble B*1501 through PCR. These constructs were then transfected into class I negative 721.221 cells and peptides purified as previously established (Prilliman, KR et al, 1998, previously incorporated herein by reference). Comparison of the two tailed transfectants with the untailed, soluble B*1501 allowed for the determination that tag addition had no effect on peptide binding specificity of the class I molecule and consequently had no deleterious effects on direct peptide ligand mapping and sequencing.

Edman Motifs

The most common means for discerning ligands presented by a particular class I molecule is Edman sequencing the pool of peptides eluted from that molecule. In order to demonstrate that tailing class I molecules with Cterminal tags does not disrupt endogenous peptide loading, Edman sequences of the peptide pools from B*1501, B*1501-HIS, and B*1501-FLAG was compared with previously published B*1501 data FIG. 2. Motifs were assigned to each of the various B*1501 molecules as shown in FIG. 2. At the anchor position 2 (P2) a dominant Q and subdominant M was seen in motifs as previously published by Falk et al. (Immunogenetics 41:165, 1995) and Barber et al. (J Exp Med 184:735, 1996). A more disparate P3 is seen in all molecules with F, K, N, P, R, and Y appearing; these results have also been previously reported by Falk and Barber. Again, a dominant Y and F are seen as the C-terminal anchors at P9 in all three molecules. The motif data for all three molecules are in close accord, therefore, with the published standard motifs.

Mass Spectrometric Profiles

Comparison of motifs for the surface bound, nontailed, and tailed B*1501 molecules identified no substantial differences in the pooled peptides bound by the various forms of B*1501 tested. However, the aim of the present invention is to subtractively compare the individual peptides bound by class I molecules from diseased and healthy cells. Subtractive analysis is accomplished through the comparison of mass spectrometric ion maps and, as such, the ion maps of tailed and untailed class I molecules were compared in order to determine the effect of tailing upon comparative peptide mapping.

Figure 3:
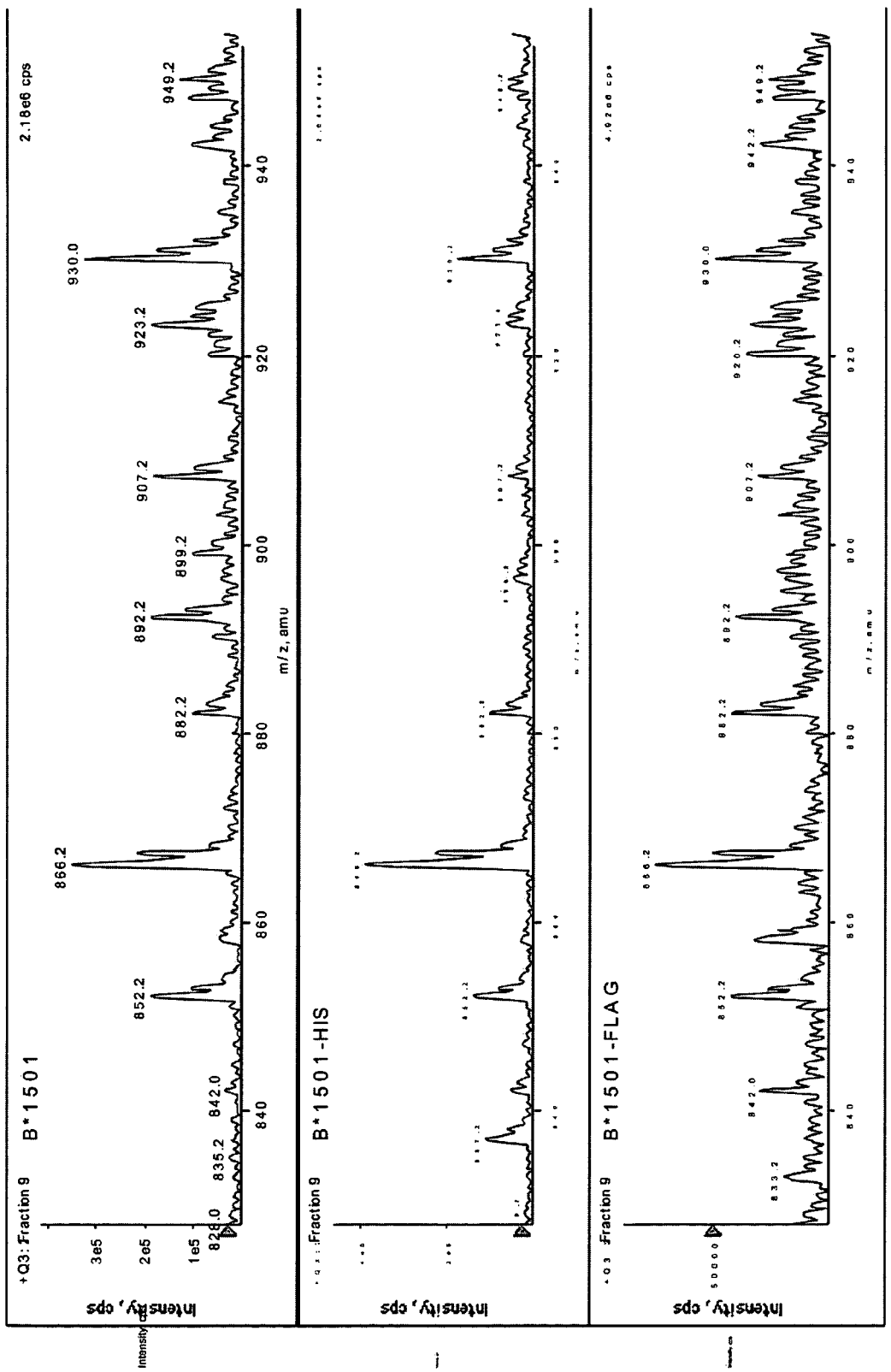
FIG. 3. Representative MS ion maps from soluble B*1501, B*1501-HIS and B*1501-FLAG illustrating ion overlap between the molecules. Pooled, acid-eluted peptides were fractionated by RP-HPLC, and the individual fractions were MS scanned.

Peptides derived from tailed and untailed B*1501 were separated into fractions via reverse phase HPLC (RP-HPLC). Each fraction was then scanned using an API-III mass spectrometer in order to identify ions present in each fraction. Overall ion scans from RP-HPLC fractions 9, 10, 11, 18, 19, and 20 were produced and visually compared in order to assess ions representing peptides overlapping between the three molecules. FIG. 3. depicts a representative section of the ion maps generated from each of the molecules. This comparison shows that the same pattern of ions is produced by the different B*1501 molecules analyzed here. The manual comparison of ion maps from each of the three fractions found little to no difference in the peptides bound by each of the three molecules.

Ligand Sequences

Figure 4:
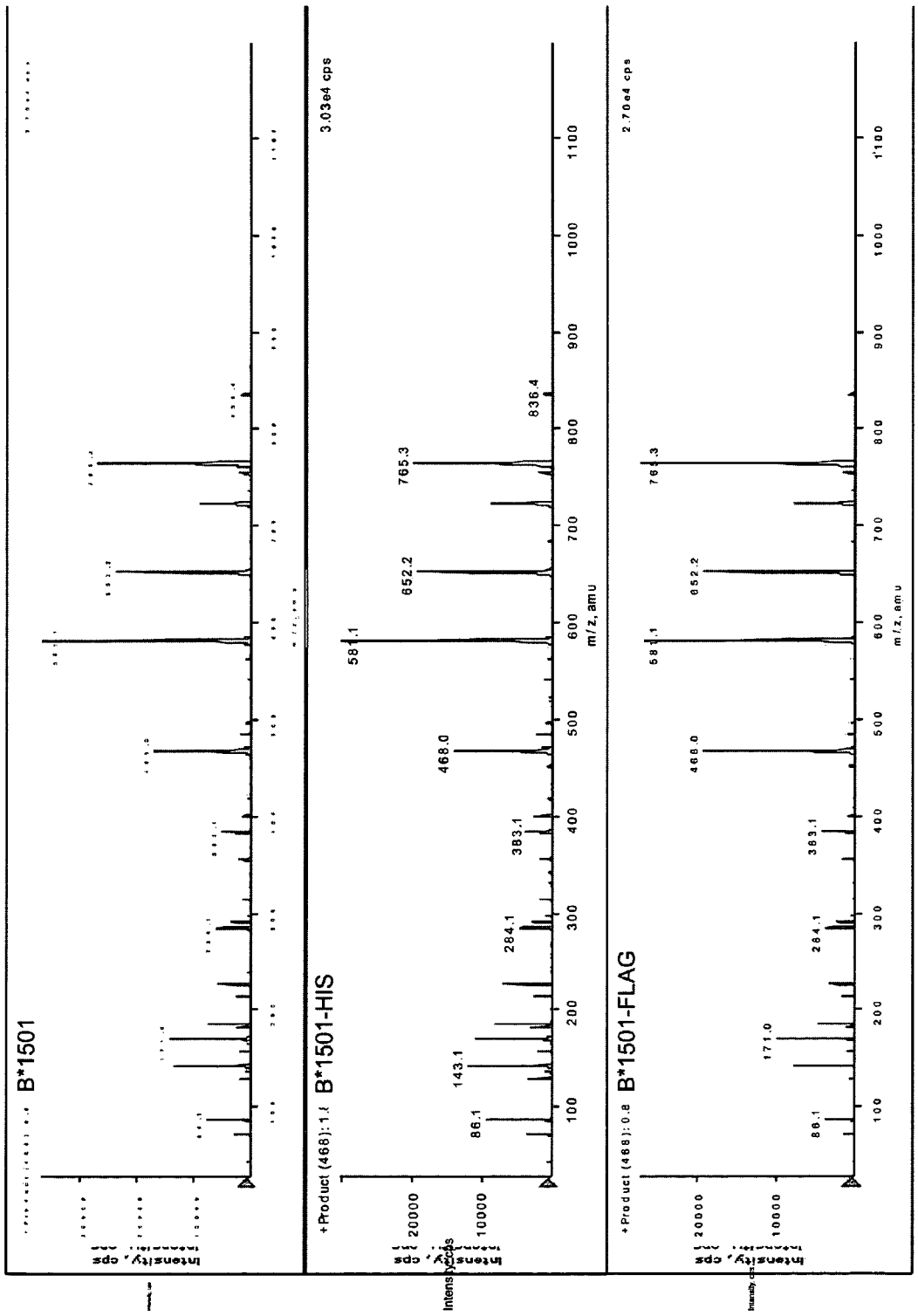
FIG. 4. Fragmentation pattern generated by MS/MS on an ion selected from fraction 11 of B*1501, B*1501-HIS and B*1501-FLAG peptides illustrating a sequence-level overlap between the three molecules.

After identification of ion matches in MS chromatograms of each of the three molecules, individual ions were chosen for sequencing by tandem mass spectrometry in order to determine if ions were indeed matched at the peptide-sequence level. Ten ions from each fraction were initially selected for MS/MS sequence generation. Fragmentation patterns for each of the ions from each molecule were manually compared and identical fragmentation patterns were counted as peptide-sequence level matches, as illustrated in FIG. 4. Of the peptide fragmentation patterns examined, 52/57 (91%) were exact matches between the untailed molecules and the 6-HIStailed protein (TABLE VI). A more disparate pattern of fragmentation was identified in the FLAG-tailed ions selected for MS/MS sequencing: of the 57 ions selected for MS/MS fragmentation comparison, 39 (70%) fragmentation patterns matched between the FLAG-tailed and untailed molecules. Overall, 91 out of 113 (81%) spectra examined were in accord between the tailed molecules and soluble B*1501.

TABLE VI

| Molecules | Ions Examined | Ion Matches | Percent Matched |
|---|---|---|---|
| B*1501-HIS | 57 | 52 | 91% |
| B*1501-FLAG | 56 | 39 | 70% |
| B*1501-Tagged | 113 | 91 | 81% |

Several ligand sequences were clearly determined from the fragmentation patterns produced. The ligand QGLISRGYSY (SEQ ID NO:54), deriving from human periplakin, was sequenced from those peptides eluted in fraction 18. A second ligand, AVRDISEASVF (SEO ID NO:55), an 11-mer matching a span of the 40S ribosomal protein S26, was identified in fraction 20. Notably, these two peptides lacked the strong consensus glutamine expected by the motif data, a phenomenon previously reported by our laboratory when sequencing B*1501-eluted ligands (Prilliman, KR et al, 1997, previously incorporated herein by reference). Both these ligands, however, terminate with an aromatic tyrosine or phenylalanine; these amino acids were both predicted to be strong anchors by Edman sequencing data and by previously published observations (Prilliman, KR et al, 1998, previously incorporated herein by reference).

One embodiment of the present invention contemplates characterizing peptide ligands bound by a given class I molecule by transfecting that molecule into a class I negative cell line and affinity purification of the class I molecule and bound peptide. Complications arise, however, when cell lines are chosen for study that already possess class I molecules. In this case, antibodies specific for one class I molecule must be used to selectively purify that class I molecule from others expressed by the cell. Because allele-specific antibodies recognize epitopes in and around the peptide binding groove, variations in the peptides found in the groove can alter antibody affinity for the class I molecule (Solheim, J C et al., J Immunol 151:5387, 1993; and Bluestone, J A et al., J Exp Med 176:1757, 1992). Altered antibody recognition can, in turn, bias the peptides available for elution and subsequent sequence analysis.

In order to selectively purify from a class I positive cell a transfected class I molecule and its peptide ligands in an unbiased way, it was necessary to alter the embodiment for class I purification in a non-class I positive cell. The C-terminal addition of a FLAG and 6-HIS tag to a class I molecule that had already been extensively characterized, B*1501 was shown to have little or no effect on peptide binding. This methodology was designed to allow purification of a single class I specificity from a complex mixture of endogenously expressed class I molecules. Ligands eluted from the tailed and untailed B*1501 molecule were compared to assess the effect of a tail addition on the peptide repertoire.

Pooled Edman sequencing is the commonly used method to determine the binding fingerprint of a given molecule, and this methodology was used to ascertain the large-scale effect of tail addition upon peptide binding. We subjected 1/100 of the peptides eluted from each class I MHC molecule to Edman degradation and derived motifs for each of the molecules. Both the HIS- and FLAG-tailed motifs matched published motifs for the soluble and membrane-bound B*1501. Each of the molecules exhibited motifs bearing a dominant P2 anchor of Q, a more disparate P3 in which multiple residues could be found, and another dominant anchor of Y or F at P9. Small differences in the picomolar amounts of each of the amino acids detected during Edman sequencing have been noted previously in consecutive runs with the same molecule and most likely reflect differences in cell handling and/or peptide isolation rather than disparities in bound peptides. Highly similar peptide motifs indicated that the peptide binding capabilities of class I MHC molecules are not drastically altered by the addition of a tag.

In order to insure the ligands were not skewed after tag addition, MS and MS/MS were used for the mapping and sequencing of individual peptides, respectively. Peptide mixtures subjected to MS provided ion chromatograms (FIG. 3) that were used to compare the degree of ion overlap between the three examined molecules. Extensive ion overlap indicates that the peptides bound by these tailed and untailed B*1501 molecules were nearly identical.

Selected ions were then MS/MS sequenced in order to confirm that mapped ion overlaps indeed represented exact ligand matches through comparison of fragmentation patterns between the three molecules (FIG. 4). Approximately 60 peptides were chosen initially for MS/MS—ten from each fraction. Overall, fragmentation patterns were exact matches in a majority of the peptides examined (TABLE VI). Fragmentation patterns categorized as nonmatches resulted from a mixture of peptides present at the same mass to charge ratio, one or more of which was present in the tagged molecule and not apparent in the spectra of the same ion from B*1501. Of the sequence-level matches, ligands derived from HIS-tailed molecules more closely matched those derived from B*1501 than those eluted from FLAG-tailed molecules. In total, 52/57 HIS peptides were exact matches, whereas 39/56 FLAG peptides were equivalent. Thus, the data indicates that the 6-HIS tag is less disruptive to endogenous peptide binding than is the FLAG-tag, although neither tag drastically altered the peptides bound by B*1501.

A handful of individual ligand sequences present in fractions of peptides eluted from all three molecules were determined by MS/MS. The two clearest sequences, AVRDISEASVF (SEQ ID NO:55) and QGLISRGYSY (SEQ ID NO:54), demonstrate that tailed class I molecules indeed load endogenous peptide ligands. This supports the hypothesis that addition of a C-terminal tag does not abrogate the ability of the soluble HLA-B*1501 molecule to naturally bind endogenous peptides. Further, both peptide sequences closely matched those previously reported for B*1501 eluted peptides having a disparate N-terminus paired with a more conserved C-terminus consisting of either a phenylalanine or a tyrosine. Given the homologous Edman sequence, largely identical fragmentation patterns, and the peptide ligands shared between the three molecules, we conclude that addition of a C-terminal tag does not significantly alter the peptides bound by B*1501.

Figure 5:
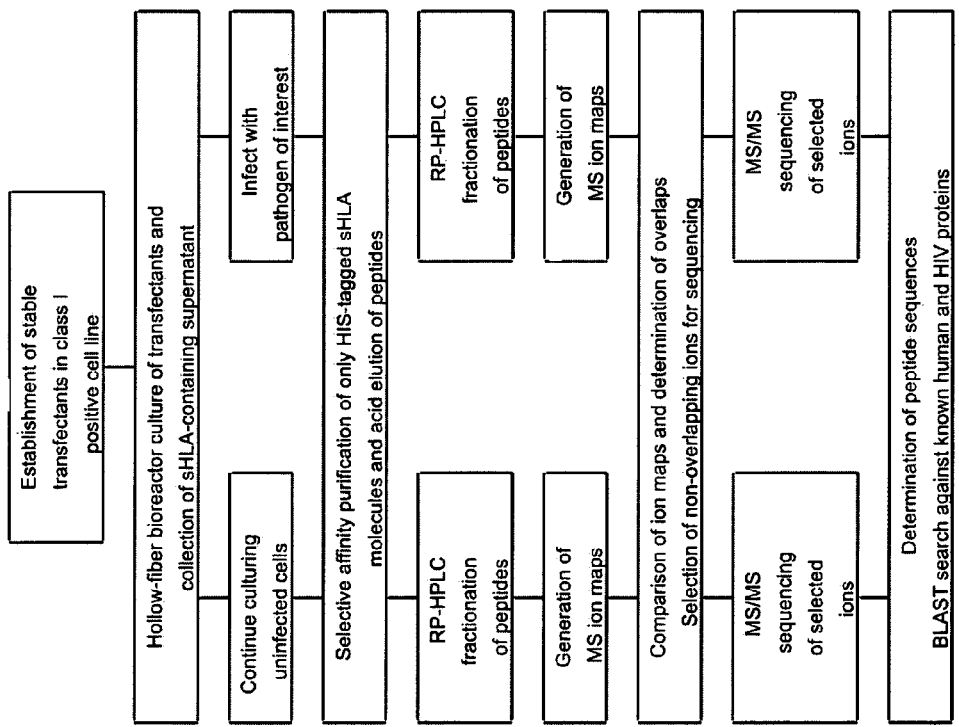
FIG. 5. Flow chart of the epitope discovery of C-terminal-tagged sHLA molecules. Class I positive transfectants are infected with a pathogen of choice and sHLA preferentially purified utilizing the tag. Subtractive comparison of MS ion maps yields ions present only in infected cell, which are then MS/MS sequenced to derive class I epitopes.

Mapping and subtractively comparing eluted peptides is a direct means for identifying differences and similarities in the individual ligands bound by a class I HLA molecule. Indeed, subtractive comparisons demonstrate how overlapping ligands bind across closely related HLA-B15 subtypes as well as pointing out which ligands are unique to virus-infected cells. Direct comparative analyses of eluted peptide ligands is well suited for a number of purposes, not the least of which is viral and cancer CTL epitope discovery. Addition of a C-terminal epitope tag provides a feasible method for production and purification of class I molecules, and therefore, peptide ligands in cell lines capable of sustaining viral infection or harboring neoplastic agents, as illustrated in FIG. 5. Direct peptide analysis from such lines should yield important information on host control of pathogenic elements as well as provide important building blocks for rational vaccine development.

The present invention further relates in particular to a novel method for detecting those peptide epitopes which distinguish the infected/tumor cell from the uninfected/non-tumor cell. The results obtained from the present inventive methodology cannot be predicted or ascertained indirectly; only with a direct epitope discovery method can the unique epitopes described herein be identified. Furthermore, only with this direct approach can it be ascertained that the source protein is degraded into potentially immunogenic peptide epitopes. Finally, this unique approach provides a glimpse of which proteins are uniquely up and down regulated in infected/tumor cells.

The utility of such HLA-presented peptide epitopes which mark the infected/tumor cell are three-fold. First, diagnostics designed to detect a disease state (i.e., infection or cancer) can use epitopes unique to infected/tumor cells to ascertain the presence/absence of a tumor/virus. Second, epitopes unique to infected/tumor cells represent vaccine candidates. Here, we describe epitopes which arise on the surface of cells infected with HIV. Such epitopes could not be predicted without natural virus infection and direct epitope discovery. The epitopes detected are derived from proteins unique to virus infected and tumor cells. These epitopes can be used for virus/tumor vaccine development and virus/tumor diagnostics. Third, the process indicates that particular proteins unique to virus infected cells are found in compartments of the host cell they would otherwise not be found in. Thus, we identify uniquely upregulated or trafficked host proteins for drug targeting to kill infected cells.

The present invention describes, in particular, peptide epitopes unique to HIV infected cells. Peptide epitopes unique to the HLA molecules of HIV infected cells were identified by direct comparison to HLA peptide epitopes from uninfected cells.

As such, and only by example, the present method is shown to be capable of identifying: (1) HLA presented peptide epitopes, derived from intracellular host proteins, that are unique to infected cells but not found on uninfected cells, and (2) that the intracellular source-proteins of the peptides are uniquely expressed/processed in HIV infected cells such that peptide fragments of the proteins can be presented by HLA on infected cells but not on uninfected cells.

The method of the present invnetion also, therefore, describes the unique expression of proteins in infected cells or, alternatively, the unique trafficking and processing of normally expressed host proteins such that peptide fragments thereof are presented by HLA molecules on infected cells. These HLA presented peptide fragments of intracellular proteins represent powerful alternatives for diagnosing virus infected cells and for targeting infected cells for destruction (i.e., vaccine development).

A group of the host source-proteins for HLA presented peptide epitopes unique to HIV infected cells represent source-proteins that are uniquely expressed in cancerous cells. For example, through using the methodology of the present invention a peptide fragment of reticulocalbin is uniquely found on HIV infected cells. A literature search indicates that the reticulocalbin gene is uniquely upregulated in cancer cells (breast cancer, liver cancer, colorectal cancer). Thus, the HLA presented peptide fragment of reticulocalbin which distinguishes HIV infected cells from uninfected cells can be inferred to also differentiate tumor cells from healthy non-tumor cells. Thus, HLA presented peptide fragments of host genes and gene products that distinguish the tumor cell and virus infected cell from healthy cells have been directly identified. The epitope discovery method of the present invention is also capable of identifiying host proteins that are uniquely expressed or uniquely processed on virus infected or tumor cells. HLA presented peptide fragments of such uniquely expressed or uniquely processed proteins can be used as vaccine epitopes and as diagnostic tools.

The methodology to target and detect virus infected cells may not be to target the virus-derived peptides. Rather, the methodology of the present invention indicates that the way to distinguish infected cells from healthy cells is through alterations in host encoded protein expression and processing. This is true for cancer as well as for virus infected cells. The methodology according to the present invention results in data which indicates without reservation that proteins/peptides distinguish virus/tumor cells from healthy cells.

Example of Comparative Ligand Mapping in Infected and Uninfected Cells Creation of Soluble Class I Construct EBV-transformed cell lines expressing alleles of interest (particularly A*0201, B*0702, and Cw*0702) were grown and class I HLA typed through the sequenced-based-typing methodology described in Turner et al. 1998, J. Immunol, 161 (3) 1406-13) and U.S. Pat. No. 6,287,764 Hildebrand et al. both of which are expressly incorporated herein in their entirety by reference. Total RNA was 5pXI and 3pEI, producing a product lacking the cytoplasmic and transmembrane domains. Alternatively, a 3' primer encoding a hexa-histidine or FLAG epitope tag was placed on the C-terminus using the primers, 3pEIHIS or 3pEIFLAG (TABLE V). For the C-locus, a 5' primer was used encoding the Kozak consensus sequence. (Davis, et al. 1999. *J. Exp. Med.* 189: 1265-1274). Each construct was cut with the appropriate restriction endonculease (see TABLE V) and cloned into the mammalian expression vector pCDNA 3.1-(Invitrogen, Carlsbad, Calif.) encoding either a resistance gene for G418 sulfate or Zeocin (Invitrogen).

Transfection in Sup-T1 cells. Sup-T1 T cells were cultured in RPMI 1640+20% fetal calf serum at 37° C. and 5% $CO_2$. Cells were split daily in order to maintain log-phase growth. Plasmid DNA was purified using either Qiagen Midi-prep kits (Qiagen, Santa Clarita) or Biorad Quantum Prep Midiprep Kit (Biorad, Hercules, Calif.) according to the manufacturer's protocol and resuspended in sterile DNAse-free water. Cells were electroporated with 30 µgs of plasmid DNA at a voltage of 400 mV and a capacitance of 960 µF. Decay constants were monitored throughout electroporation and only transfections with decay times under 25 mS were carried through to selection. Selection was performed on day 4 post-transfection with 0.45 mg/mL Zeocin (Invitrogen) selective medium containing 30% fetal calf with the pH adjusted visually to just higher than neutral. Cells were resuspended in selective medium at $2\times10^6$ cells per ml, fed until they no longer turned the wells yellow (using the pH indicated Phenol Red (Mediatech)), and allowed to sit until cells began to divide. After the appearance of active division, cells were slowly fed with selective medium until they reached medium (T-75) tissue culture flasks. Cells were then subcloned at limiting dilutions of 0.5, 1, and 1.5 cells per well in 96-well tissue culture plates. Cells were allowed to sit until well turned yellow, they were then gradually moved to 24 well plates and small (T-25) tissue culture flasks. Samples were taken for soluble class I ELISA, and the best producers of class I were frozen for later use at $5 \times 10^{\wedge}6$ cells/ml and stored at $-135°$ C.

Soluble MHC class I ELISA. ELISAs were employed to test the concentration of the MHC class I/peptide complexes in cell culture supernatants. The monoclonal antibody W6/32 (ATCC, Manassas, Va.) was used to coat 96-well Nunc Starwell Maxi-sorp plates (VWR, West Chester, Pa.). One hundred μls of test sample containing class I was loaded into each well of the plate. Detection was with anti-βB2 microglobulin (light chain) antibody conjugated to horse-radish peroxidase followed by incubation with OPD (Sigma, St. Louis, Mo.). ELISA values were read by a SpectraMax 340 00A, Rom Version 2.04, February, 1996, using the program Softmax Pro Version 2.2.1 from Molecular Devices. For determination of MHC class I complex in carboys prior to affinity purification (see below), each sample was tested in triplicate on at least 2 separate plates. Uninfected and infected harvest concentrations were read on the same plate and uninfected samples were brought to 1% Triton X 100 prior to loading on the ELISA plate. This was in an attempt to minimize variability in mass spectra generate due to large differences in the amount of peptide loaded onto affinity columns.

Full-length construct creation. Full-length constructs (in the pCDNA3.1-/G418 sulfate resistance vector) were created and transfected into the class I negative B-LCL 721.221 and T2. Both cell lines were cultured in RPMI-1640+10% fetal calf serum until growing at log phase. Cells were electroporated at 0.25 V and 960 μF capacitance. After 2 days, the cells were pelleted and resuspended in selective medium consisting of RPMI-1640+20% FCS+1.5 mg/ml G418 sulfate (Mediatech, Herndon, Va.). Cells were treated in the same manner as above (Sup-T1 transfection) after this point.

Cell pharm production. Eight liters of Sup-T1 soluble MHC class I transfectants cultured in roller bottles in RPMI-1640+15% FCS+100 U penicillin/streptomycin were centrifuged for 10 min at 1100× g. Supernatant was discarded and a total of $3 \times 10^{\wedge}9$ total cells were resuspended in 200 mls of conditioned medium. Infected cells were then added to a feed bottle and inoculated through the ECS feed pump of a Unisyn CP2500 cell pharm (Unisyn, Hopkington, Mass.) into 30 kD molecular-weight cut-off hollow-fiber bioreactors previously primed with RPMI-1640 containing 20% fetal calf serum. Cells were allowed to incubate overnight in the bioreactor at a temperature of 37° C. and at a pH of 7.20 maintained automatically through $CO_2$ injection into the medium reservoir of the system. No new medium was introduced into the system during this time period and the ICS recirculation was maintained at a low value of 400 mls/minute. ECS feed was begun 12 hours post inoculation at a rate of 100 mls/day with 15% FCS supplemented RPMI-1640; ICS feed was likewise begun at a rate of 1 L/day. ECS recirculation was initiated at day 2 post-inoculation at a rate of 4 L/day. ECS and ICS samples were taken at 24-hour intervals and sHLA ELISAs (see above) and glucose tests performed. ECS and ICS feed rates as well as ECS and ICS recirculation rates were adjusted based on increasing concentrations of sHLA in the harvest and decreasing levels of glucose in the ICS medium.

Virus production and infection HIV MN-1 production. HIV MN-1 cloned virus (Genbank Accession Number M17449) was thawed from frozen stock and used to infect $25 \times 10^{\wedge}6$ non-transfected Sup-T1 (Denny C T, et. al. 1986. Nature. 320:549.51, which is expressly incorporated herein in its entirety by reference) T cells using standard methods. Cells were cultured in RPMI-1640+20% fetal bovine serum (MediaTech) for 5 days and observed for syncitia formation. Upon formation of syncitia, new cells were added in fresh RPMI-1640/20% FCS. Culture was continued for 5 more days when 100 mls of infected cells were removed. Supernatant was passed through a 0.45 um filter and cell-free virus was aliquotted and stored at $-80°$ C. This process was continued until an appropriate amount of virus was harvested.

HIV-1 NL4-3 production. The infectious molecular clone pNL4-3 (Genbank Accession Number AF324493) was transformed into the *Esherichia coli* strain Top10F' (Invitrogen, Carlsbad, Calif.). Plasmid DNA was midiprepped from transformed cells using either the Qiagen Midi Prep Kit (Qiagen, Santa Clarita, Calif.) or the Biorad Quantum Prep Midiprep Kit (Biorad, Hercules, Calif.) according to the manufacturer's instructions. Plasmid DNA was used to transfect 293T cells (GenHunter Corporation, Nashville, Tenn.) using Roche's Fugene 6 reagent (Roche, Basel, Switzerland) following the manufacturer's protocol. Virus-containing supernatant was harvested at 24, 48, and 72 hours, clarified by centrifugation at 500× g for 10 min, aliquotted, and stored at $-80°$ C. Sup-T1 transfectants containing either soluble A*0201, B*0702, or Cw*0702 were cocultured with virus resulting in high-titre virus. After 72 hours, infected cells were centrifuged at 1100× g for 10 minutes. Supernatant containing cell-free virus was removed, passed through a 0.45 μm filter, aliquotted, and stored at $-80°$ C. Virally-infected cells were resuspended in freeze medium (RPMI-1640+20% FCS+10% DMSO) at approximately $6 \times 10^{\wedge}6$ cells per ml and stored at $-80°$ C.

Viral Titer Determination. One vial of frozen viral stock derived from either strain of HIV was thawed and used in a $TCID_{50}$ assay scored two ways: 1) wells containing at least 3 syncitia were considered positive or 2) wells containing over 50 ng/ml p24 antigen as determined by ELISA were considered positive. The $TCID_{50}$ was then calculated using the Spearman-Karber method (DAIDS Virology Manual for HIV Laboratories, January 1997). The average of both scoring methods was used as the final titer of the virus. As a second means of viral titer monitoring, viral stock was used undiluted in a p24 ELISA (Beckman Coulter, Miami, Fla.) in order to determine the ngs of p24 present in cell-free virus.

P24 ELISA. Determination of HIV p24 major core protein was determined by the commercially available Beckman Coulter p24 ELISA according to the manufacturer's instructions with the exceptions of the following modifications: samples were treated with 10% Triton-X 100 prior to removal from a BSL-3 facility, therefore the inactivation medium included in the kit was not used. Secondly, samples were serially diluted in water prior to use.

Hollow-fiber bioreactor culture of infected cells. All work including large-scale culture of HIV was performed in a Biosafety Level 3 Laboratory in accordance with guidelines set forth by the National Institutes of Health. HIV MN-1 frozen viral stock aliquots were thawed and pooled to a 100 ml total volume, containing approximately $5.5 \times 10^{\wedge}6$ $TCID_{50}$'s. Eight liters of Sup-T1 soluble MHC class I transfectants cultured in roller bottles in RPMI-1640+15% FCS+100 U penicillin/streptomycin were centrifuged for 10 min at 1100× g. Supernatant was discarded and a total of $3 \times 10^{\wedge}9$ total cells were resuspended in 200 mls of conditioned medium. The 100 mls of cell-free HIV MN-1 was then added to the resuspended cells and incubated at 37° C. in % 5 $CO_2$ for 2 hours with gentle shaking every 20 minutes. Infected cells were then added to a feed bottle and inoculated through the ECS feed pump of a Unisyn CP2500 cell pharm (Unisyn, Hopkington, Mass.) into: 30 kD molecular-weight cut-off hollow-fiber bioreactors previously primed with RPMI-1640 containing 20% fetal calf serum. Cells were allowed to incubate overnight in the bioreactor at a temperature of 37° C. and at a pH of 7.20 maintained automatically through $CO_2$ injection into the medium reservoir of the system. No new medium was introduced into the system during this time period and the recirculation was maintained at a low value of 400 mls/minute. ECS feed was begun 12 hours post inoculation at a rate of 100 mls/day with 15% FCS supplemented RPMI-1640; ICS feed was likewise begun at a rate of 1 L/day. ECS and ICS samples were taken at 24-hour intervals, inactivated by addition of Triton-X 100 to 1%, and sHLA ELISAs, p24 ELISAs, and glucose tests performed as described above. ECS and ICS feed rates as well as ECS and ICS recirculation rates were adjusted based on increasing concentrations of sHLA in the harvest and decreasing levels of glucose in the ICS medium.

Soluble HLA purification. Soluble-HLA containing supernatant was removed in 1.9 L volumes from infected hollow-fiber bioreactors. Twenty-percent Triton-X 100 was sterilized and placed in 50 ml aliquots in 60 mls syringes; 2 syringes were injected into each 1.9 L harvest bottle as it was removed from the cell pharm, resulting in a final TX 100 percentage of 1%. Bottles were inverted gently several times to mix the TX 100 and stored at 4° C. for a minimum of 1 week. After 1 week, harvest was centrifuged at 2000× g for 10 minutes to remove cellular debris and pooled into 10 L carboys. An aliquot was then removed from the pooled, HIV-inactivated supernatant and used in a quantitative $TCID_{50}$ assay (as described above) and used to initiate a coculture with Sup-T1's. Only after demonstration of a completely negative coculture as well as $TCID_{50}$ were harvests removed from the BSL-3.

Class I/Peptide Production and Peptide Characterization Handling of MHC classI/peptide complexes from infected cells. Each 10 L of cell pharm harvest was separated strictly on a temporal basis during the cell pharm run. (This was an attempt to assess any epitopic changes that might occur temporally during infection as opposed to those that might occur more globally.) Harvest was treated exactly as described above, except for the removal of a 2 ml aliquot for tests in both a $TCID_{50}$ assay and cell coculture assay to determine infectivity of the virus.

Affinity purification of infected and uninfected MHC class I complexes. Uninfected and infected harvest removed from CP2500 machines were treated in an identical manner post-removal from the cell pharm. Approximately 50 mgs total class I as measured by W6/32 ELISA (see above) were passed over a Pharmacia XK-50 (Amersham-Pharmacia Biotech, Piscataway, N.J.) column packed with 50 mls Sepharose Fast Flow 4B matrix (Amersham) coupled to W6/32 antibody. Bound class I complexes were washed first with 1 L 20 mM sodium phosphate wash buffer, followed by a wash with buffer containing the zwitterionic detergent Zwittergent 3-08 (Calbiochem, Merck KgaA, Darmstadt, Germany) at a concentration of 10 mM, plus NaCl at 50 mM, and 20 mM sodium phosphate. The zwittergent wash was monitored by UV absorption at a wavelength of 216 nm for removal of Triton-X 100 hydrophobically bound to the peptide complexes. After 1 L of wash had passed over the column (more than a sufficient amount for the UV to return to baseline), zwittergent buffer was removed with 2 L of 20 mM sodium phosphate wash buffer. Peptides were eluted post wash with freshly made 0.2N acetic acid, pH 2.7.

Peptide isolation and separation. Post-elution, peptide-containing eluate fractions were brought up to 10% glacial acetic acid concentration through addition of 100% glacial acetic acid. Fractions were then pooled into a model 8050 stirred cell (Millipore, Bedford, Mass.) ultrafiltration device containing a 3 kD molecular-weight cutoff regenerated cellulose membrane (Millipore). The device was capped and tubing parafilmed to prevent leaks and placed in a 78° C. water bath for 10 minutes. Post-removal, the peptide-containing elution buffer was allowed to cool to room temperature. The stirred cell was operated at a pressure of 55 psi under nitrogen flow. Peptides were collected in 50 ml conical centrifuge tubes (VWR, West Chester, Pa.), flash frozen in supercooled ethanol, and lyophilized to dryness. Peptides were resuspended either in 10% acetic acid or 10% acetonitrile. Peptides were purified through a first-round of HPLC on a Haisil C-18 column (Higgins Analytical, Moutain View, Calif.), with an isocratic flow of 100% B (100% acetonitrile, 0.01% TFA) for 40 minutes. Following elution, peptide-containing fractions were pooled, speed-vacuumed to dryness, and resuspended in 150 μls of 10% acetic acid. Two μgs of the base methyl violet were added to the peptide mixture in 10% acetic acid and this was loaded onto a Haisil C-18 column for fractionation. Peptides were fractionated by one of two methods, the latter resulting in increased peptide resolution. The first fractionation program was 2-10% B in 2 minutes, 10-60% B in 60 minutes, with 1 minute fraction collection. The second RP-HPLC gradient consisted of a 2-14% B in 2 minutes, 14-40% B in 60 minutes, 40-70% B in 20 minutes, with 1 minute fraction collection. Peptides eluting in a given fraction were monitored by UV absorbance at 216 nm. Separate but identical (down to the same buffer preparations) peptide purifications were done for each peptide-batch from uninfected and infected cells.

Mass-spectrometric mapping of fractionated peptides. Fractionated peptides were mapped by mass spectrometry to generate fraction-based ion maps. Fractions were speed-vacuumed to dryness and resuspended in 12 μls 50:50 methanol:water+0.05% acetic acid. Two μls were removed and sprayed via nanoelectrospray (Protana, Odense, Denmark) into a Q-Star quadrupole mass spectrometer with a time-of-flight detector (Perseptive SCIEX, Foster City, Calif.). Spectra were generated for masses in the range of 50-1200 amu using identical mass spectrometer settings for each fraction sprayed. Spectra were then base-line subtracted and analyzed using the programs BioMultiview version 1.5beta9 (Perseptive SCIEX) or BioAnalyst version 1.0 (Persceptive SCIEX). Spectra from the same fraction in uninfected/infected cells were manually aligned to the same mass range, locked, and 15 amu increments visually assessed for the presence of differences in the ions represented by the spectra (for an example, see Hickman et al. 2000. *Human Immunology.* 61:1339-1346 which is expressly incorporated herein by reference). Ions were selected for MS/MS sequencing based on upregulations or downregulation of 1.5 fold over the same ion in the uninfected cells, or the presence or absence of the ion in infected cells. Ions were thus categorized into multiple categories prior to MS/MS sequencing.

Tandem mass-spectrometric analysis of selected peptides. Lists of ions masses corresponding to each of the following categories were generated: 1) upregulated in infected cells, 2) downregulated in infected cells, 3) present only in infected cells, 4) absent in infected cells, and 5) no change in infected cells. The last category was generally disregarded for MS/MS analysis and the first 4 categories were subjected to MS/MS sequencing on the Q-Star mass spectrometer. Peptide-containing fractions were sprayed into the mass spectrometer in 3 μl aliquots. All MS settings were kept constant except for the Q0 and Cad gas settings, which were varied to achieve the best fragmentation. Fragmentation patterns generated were interpreted manually and with the aid of BioMultiView version 1.5 beta 9. No sequencing algorithms were used for interpretation of data, however multiple web-based applications were employed to aid in peptide identification including: MASCOT (Perkins, DN et al. 1999. *Electrophoresis.* 20(18):3551-3567), Protein Prospector (Clauser K. R. et al. 1999. *Analytical Chemistry.* 71:2871), PeptideSearch (European Molecular Biology Laboratory website) and BLAST search (National Center for Biotechnology website).

Quality control of epitope changes. Multiple parameters were established before peptides identified in the above fashion were deemed "upregulated," "downregulated," etc. First, the peptide fractions before and after the fraction in which the peptide was identified were subjected to MS/MS at the same amu under the identical collision conditions employed in fragmentation of the peptide-of-interest and the spectra generated overlaid and compared. This was done to make sure that, in the unlikely event that the peptides had fractionated differently (even with methyl-violet base B standardization) there was not the presence of the peptide in an earlier or later fraction of the uninfected or infected peptides (and that the peptides had truly fractionated in an identical manner.) Secondly, the same amu that was used to identify the first peptide was then subjected to MS/MS in the alternate fraction (either infected or uninfected, whichever was opposite of the fraction in which the peptide was identified.) Spectra again were overlaid in order to prove conclusively that the fragmentation patterns did not match and thus the peptide was not present in the uninfected cells;, or, in the case that the fragmentation patterns did match, that the peptides were upregulated in the infected cells. Finally, synthetic peptides were generated for each peptide identified. These peptides were resuspended in 10% acetic acid and RP-HPLC fractionated under the same conditions as employed for the original fractionation, ensuring that the peptide putatively identified had the same hydrophobicity as that of the ion MS/MS fragmented. This synthetic peptide was MS/MS fragmented under the same collision conditions as that of the ion, the spectra overlaid, and checked for an exact match with the original peptide fragment.

Functional Analysis\Literature Searches. After identification of epitopes, literature searches were performed on source proteins to determine their function within the infected cell. Broad inferences can be made from the function of the protein. Source proteins were classified into groups according to functions inside the cell. Again, broad inferences can be made as to the groups of proteins that would be available for specific presentation solely on infected cells. Secondly, source proteins were scanned for other possible epitopes which may be bound by other MHC class I alleles. Peptide binding predictions (Parker, K. C., et. al. 1994. *J. Immunol.* 152:163) were employed to determine if other peptides presented from the source proteins were predicted to bind. Proteasomal prediction algorithms (A. K. Nussbaum, et. Al. 2001. *Immunogenetics* 53:87-94) were likewise employed to determine the likelihood of a peptide being created by the proteasome.

Sequence Identification. A discussion of the results seen with the application of this procedure is included using the peptide GPRTAALGLL as an example. Other examples and data obtained based on the methodology are listed in TABLE VII.

TABLE VII

| ION | FRACTION | SEQUENCE | MW | OBS'D MW | SOURCE PROTEIN | START AA | ACCESSION # | CATEGORY | SEQ ID NO: |
|---|---|---|---|---|---|---|---|---|---|
| Peptides Identified on Infected cells that are not present on Uninfected Cells | | | | | | | | | |
| 612.720 | 32INF | EQMFEDIISL | 1223.582 | 1223.418 | HIV MN-1, ENV | 101 | | HIV-DERIVED | 29 |
| 509.680 | 31INF | IPCLLISFL | 1017.601 | 1017.334 | CHOLINERGIC RECEPTOR, ALPHA-3 POLYPEPTIDE | 250 | | | 30 |
| 469.180 | 31INF | STTAICATGL | 936.466 | 936.360 | UBIQUITIN-SPECIFIC PROTEASE | 152 | 10720340 | | 31 |
| 420.130 | 16INF | APAQNPEL | 838.426 | 838.259 | B-ASSOCIATED TRANSCRIPT PROTEIN 3 (BAT3) | | | MHC GENE PRODUCT | 32 |
| 500.190 | 28INF | LVMAPRTVL | 998.602 | 998.396 | HLA-B HEAVY CHAIN LEADER SEQUENCE | 2 | 4566550 | MHC GENE PRODUCT | 33 |
| 529.680 | 31INF | APFI[NS]PADX | 1057.388 | | UNKNOWN, CLOSE TO SEVERAL cDNA's | | | UNKNOWN | 34 |
| 523.166 | 12INF | TPQSNRPVm | 1044.500 | 1044.333 | RNA POLYMERASE II POLYPEPTIDE A | 527 | 4505939 | RNA MACHINERY/ BINDING PR | 35 |
| 444.140 | 16INF | AARPATSTL | 887.495 | 887.280 | EUK, TRANSLATION INITIATION FACTOR 4 | 1073 | Q04637 | RNA MACHINERY/ BINDING PR | 36 |
| 470.650 | 16INF | MAMMAALMA | 940.413 | 939.410 | SPARC-LIKE PROTEIN | 19 | 478522 | TUMOR SUPPRESSOR GENE? | 37 |
| 490.620 | 16INF | IATVDSYVI | | 979.240 | TENASCIN-C (HEXABRACHION) | 1823 | 13639246 | TUMOR SUPPRESSOR GENE? | 38 |
| 563.640 | 16INF | SPNQARAQAAL | 1126.597 | 1126.364 | POLYPYRIMIDINE TRACT-BINDING PROTEIN 1 | 141 | 131528 | RNA MACHINERY/ BINDING PR | 39 |

TABLE VII-continued

| ION | FRAC-TION | SEQUENCE | MW | OBS'D MW | SOURCE PROTEIN | START AA | ACCES-SION # | CATEGORY | SEQ ID NO: |
|---|---|---|---|---|---|---|---|---|---|
| | 30INF | GPRTAALGLL | 968.589 | 968.426 | RETICULOCALBIN | 4 | 4506457 | TUMOR SUP-PRESSOR GENE? | 40 |
| 556.150 | 16INF | NPNQNKNVAL | 11111.586 | 1111.300 | ELAV (HuR) | 188 | 4503551 | RNA MACHIN-ERY/BINDING PR | 41 |
| Peptides Identified on Uninfected cells that are not present on Infected cells | | | | | | | | | |
| | 16UNINF | GSHSMRY | | | MHC CLASS I HEAVY CHAIN (could derive from multiple alleles, i.e., HLA-B*0702 OR HLA-G, etc.) | vari-able | multiple | MHC Class I Product | 42 |

Figure 6:
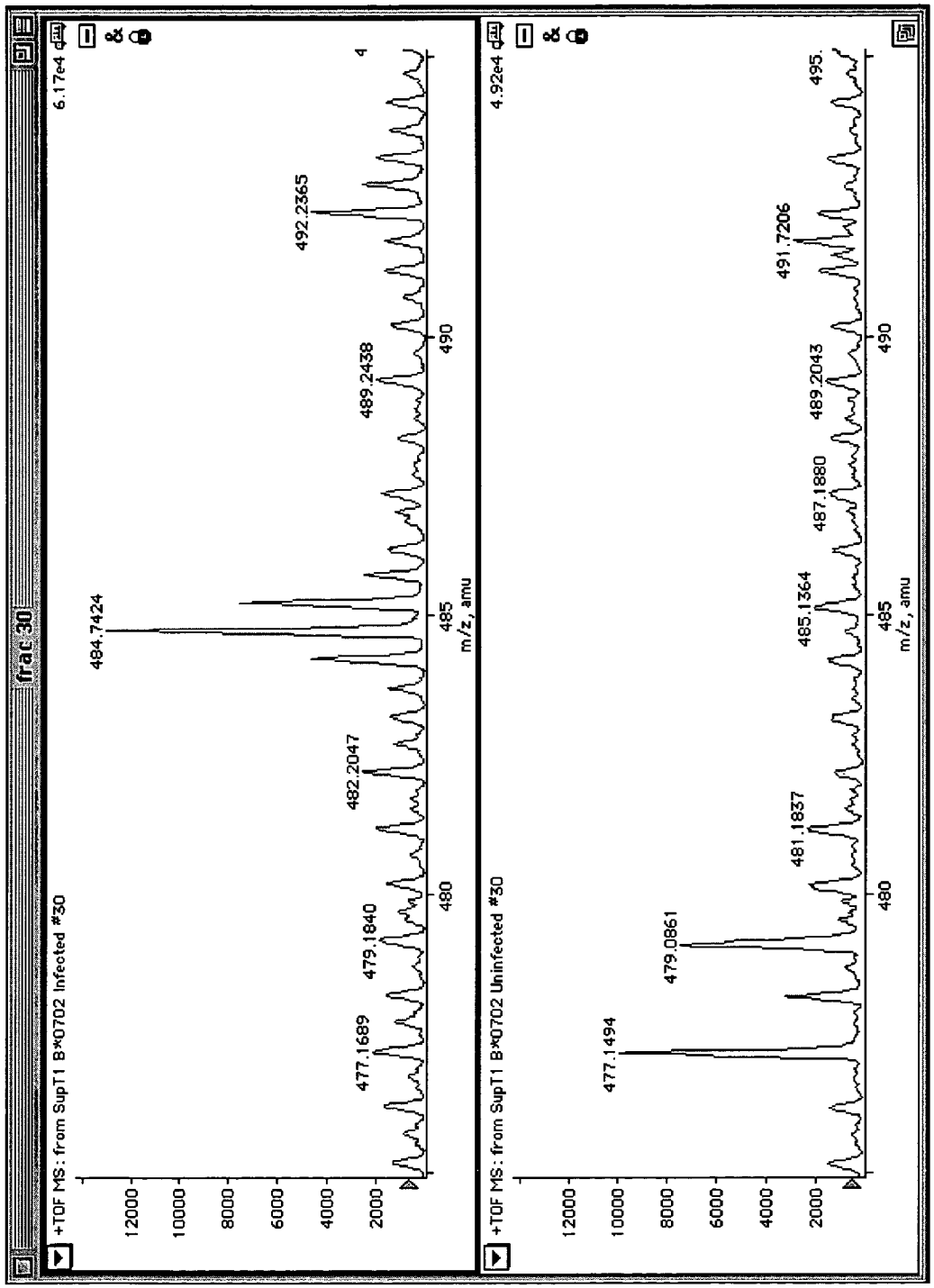
FIG. 6. MS ion map from soluble B*0702 SupT1 cells uninfected and infected with HIV MN-1. Pooled, acid-eluted peptides were fractionated by RP-HPLC, and fraction #30 was MS scanned.
Figure 7:
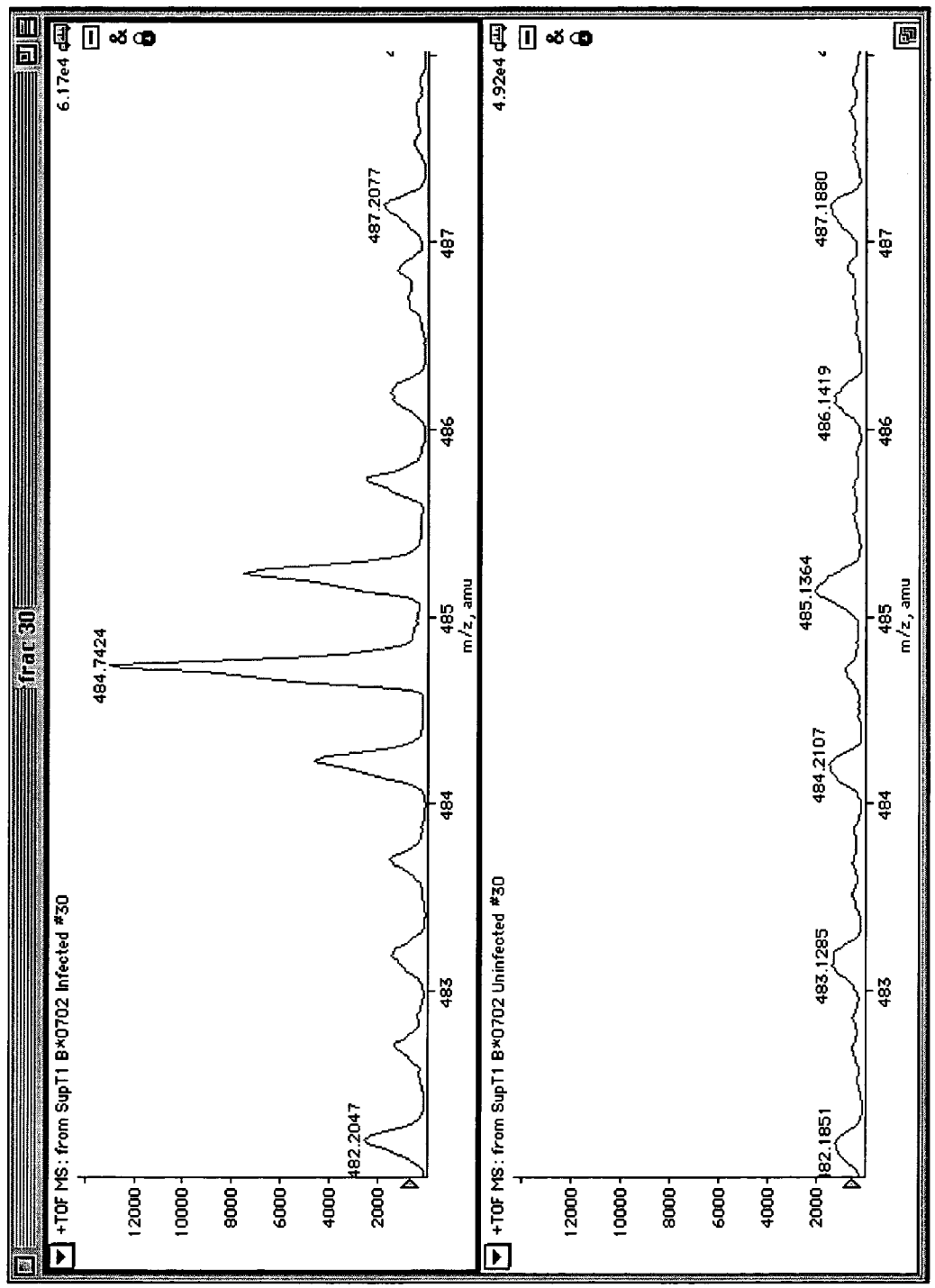
FIG. 7. MS ion map similar to FIG. 6 but zoomed in on the area from 482-488 amu to more clearly identify all ions in the immediate area.

The first step in identification of an epitope present only on uninfected cells is performing MS ion mapping. In this case, the reversed-phase HPLC fraction 30 obtained from HIV as disclosed hereinabove (which contains a fraction of the total class I peptides) was sprayed into the mass spectrometer and an ion spectrum created. FIG. 6 shows the sections of ion map in which an ion was first identified as upregulated. The ion at 484.74 can be seen to predominate in the upper map, which is the spectrum generated from peptides from the infected cells. One can also see that there are other peptides which differ in their intensities between the uninfected cells from one spectrum to another. After a peptide is initially identified, the area of the spectrum in which the peptide is found is zoomed in on in order to more fully see all the ions in the immediate area (FIG. 7). After zooming in on the area from 482-488 amu, the ion at 484.72 can be seen to only be present in the infected cells (which are seen in the spectrum on the top). A large difference such as this is not always seen, sometimes more minor differences are chosen for sequence determination. This ion, however, was considered an extremely good candidate for further analysis.

Figure 8:
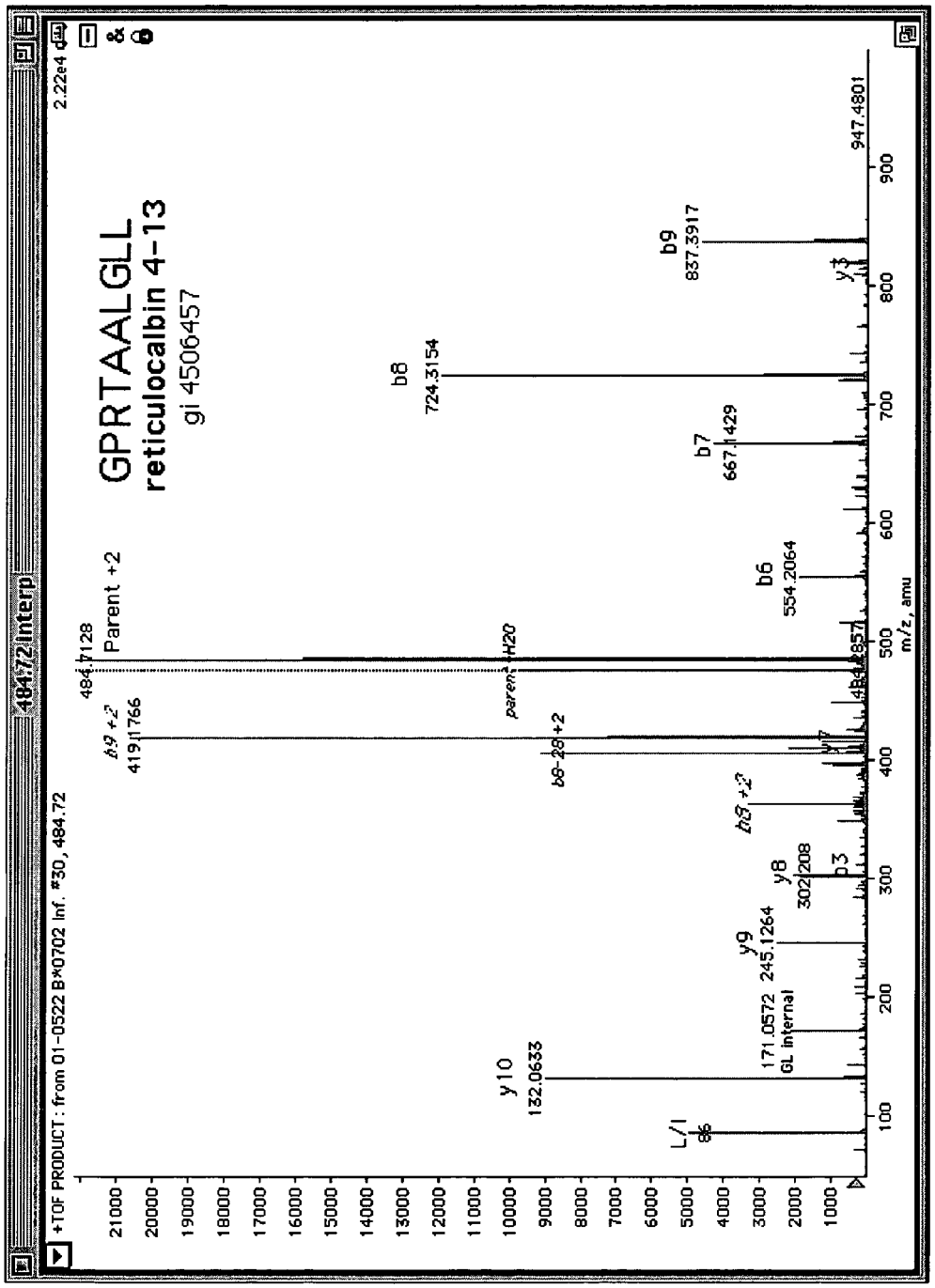
FIG. 8. Fragmentation pattern generated by tandem mass spectrometry of the peptide ion 484.72 isolated from infected soluble B*0702 SupT1 cells.

After identification of the ion, the next step in the process is to sequence the peptide by using tandem mass spectrometry. FIG. 8 shows the spectrum generated when the peptide is fragmented. These fragments are used to discern the amino acid sequence of the peptide. The sequence of this peptide was determined to be GPRTAALGLL (SEQ ID NO:40). This peptide was isolated from infected HLA-B*0702 molecules. One early quality control step is examining the peptide's sequence to see if it fits the sequences that were previously shown to be presented by this molecule. B*0702 binds peptides that have a G at their second position (P2) and an L as their C-terminal anchor. Based on this information, this sequence is likely to be a peptide presented by B*0702.

Descriptive characterization of peptide. Once the peptide sequence is obtained, information is gained on the source protein from which the peptide was derived in the cytosol of the infected cell. Initially, a BLAST search (available at the National Center for Biotechnology website) is done to provide protein information on the peptide. A BLAST search with the sequence GPRTAALGLL (SEQ ID NO:40) pulled up the protein reticulocalbin 2. After the source protein is known, information about the protein is ascertained first from the PubMed (again available at the National Center for Biotechnology website) and put into a format to which one can easily refer as seen in FIG. 9. All of the accession numbers for the protein, as well as the original description of the protein are included. This makes it easy to come back to the information for downstream use. Also, the protein sequence is copied, pasted, and saved as a text document for incorporation into later searches. The peptide is highlighted in the entire protein, giving some context as to where it is derived and how large the total protein is. This is the initial data gathering step post-sequence determination.

The next step in characterizing the ligand is doing literature searches on the source protein from which the peptide was derived. The protein is entered into the PubMed database and all entries with the word "reticulocalbin" are retrieved. FIG. 10 illustrates the listing that is done to summarize what has previously been described for this protein. It can be seen that for reticulocalbin, multiple articles have been published involving this protein. The literature is summarized in a paragraph following the PubMed listings and put into the report. For reticulocalbin, some of the most interesting points are that it is an ER resident protein, which can lead to speculation on why it is presented on infected cells. Secondly, it has been previously found to be upregulated in several other types of cancers, such as breast and colorectal cancers. This again leads to speculation that this protein may be broadly applicable to treat more maladies than those caused by HIV. It is also determined whether or not this protein has been previously cited as interacting with/or being interfered with by HIV. This was not seen for reticulocalbin and thus was not listed in the report, (although in some instances it is seen.) A broad understanding of the protein is gained through literature searches.

Predictive characterization of peptide. After the literature search, several secondary searches are performed. FIG. 11 illustrates the results of a peptide-binding algorithm performed using Parker's Prediction (which is described hereinabove). The entire source protein is used for input and the computer generates a list of peptides which are bound by the HLA allele chosen. In this case, B*0702 was chosen because that was the allele from which this peptide was derived. From the black arrow in the figure, it can be seen that the peptide sequenced by mass spectrometry is predicted to bind to HLA-B*0702 with a high affinity. Several other peptides are listed that are predicted to bind as well. FIG. 12 shows the same procedure being performed with the source peptide using another well-known search engine, SYPEITHI. Again, the results from this search engine for B*0702 shows that this peptide is predicted to bind to HLA-B*0702 with a high affinity. Also, multiple other peptides are predicted to be derived from this source protein and bound. This prediction allows us to determine several things. First, we can tell if the peptide is predicted to be bound by previous algorithms. This allows us to know how well the programs work, and/or if other people could identify this peptide (if they had the source protein) from peptide binding algorithms. All of this information can be translated into increasing importance for the present inventive methodology not only for the peptide but also for the source protein itself.

After peptide-binding algorithms are performed, searches are done to determine whether the peptides would be created by the proteasome during normal processing of proteins into peptides. It should be strongly noted that multiple pathways for class I peptide loading are now being demonstrated and that the cleavage algorithms for human proteasomes are not well established by any means. While a positive result may indicate that the proteasome is largely responsible for cleavage, a negative result by no means indicates that the peptide is not presented in the class I molecule. FIG. 13 shows the results of the first proteasomal cleavage done for the source protein reticulocalbin using the cleavage predictor PaProC. The epitope is outlined. By this prediction software, the peptide is not predicted to be cleaved by the normal proteasome. This may mean that in infected cells, alternative pathways of MHC class I presentation are being used, particularly in reference to the reticulocalbin peptide. This, in turn, may present novel methods for therapeutics during viral infection. A second proteasomal cleavage search is also employed using the prediction software NetChop (available on the worldwide web) as seen in FIG. 14. By this prediction and other data from current literature in the field, the peptide would be created by the proteasome and cleaved to form the GPRTAALGLL (SEQ ID NO:40) identified.

A third round of analysis involves only the source protein. All other alleles are tested for peptide binding and lists of the highest binders generated. The proteasomal cleavage predictions are then referred to in order to elucidate how these peptides are generated. This information is useful for downstream testing of peptides and for determining whether or not this protein will be applicable for vaccine trials covering a broad range of HLA alleles. For reticulocalbin, multiple high-affinity peptides were demonstrated for differing HLA alleles (some examples of which are shown in FIG. 15) In this figure, several high affinity peptides deriving from reticulocalbin were identified for HLA-A*0201 and A*0101.

Quality control of sequence determination. There currently exists no direct means to score the quality of MS/MS sequence data. Once all descriptive and predictive steps are concluded, we return again to the original peptide sequence for quality control to ensure that the peptide is indeed what we have identified as the amino acid sequence and that the peptide is truly present only in infected cells. We employ these multiple steps so there is no doubt that the sequence is truly what we claim it to be before we move on to downstream applications involving the peptide.

Figure 16:
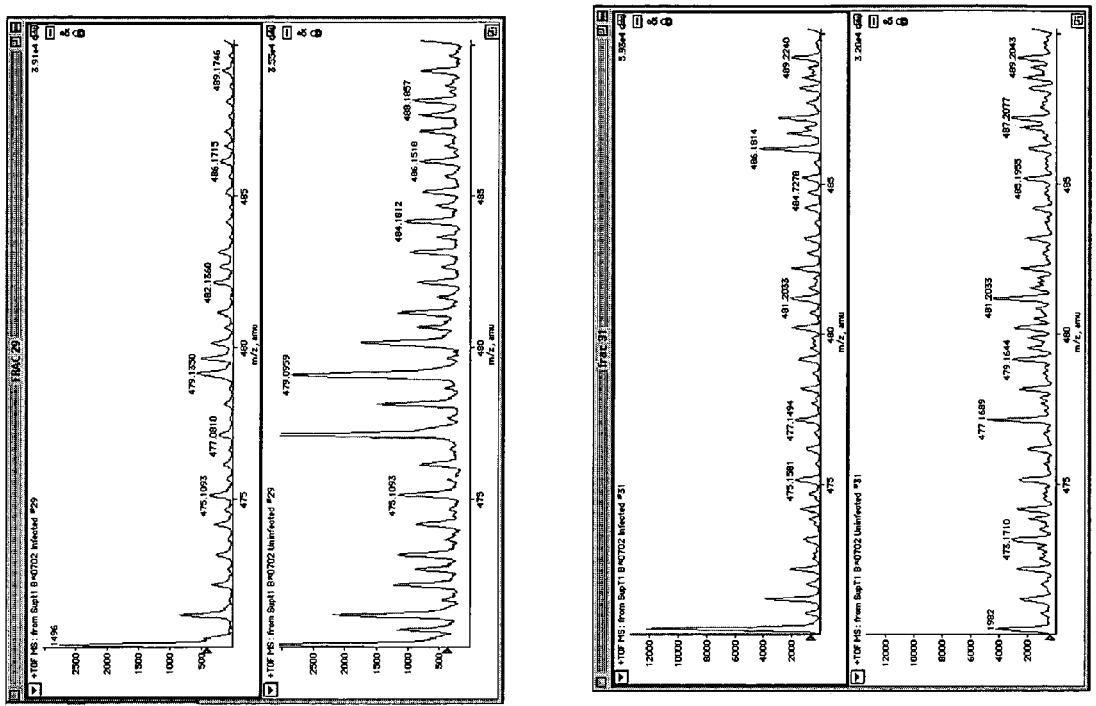
FIG. 16. MS ion maps from soluble B*0702 uninfected SupT1 cells of fractions 29 and 31 to determine that ion 484.72 was not present.

Initially, we determine that the peptide is truly upregulated or present only in infected cells. For the reticulocalbin peptide, we determined that this peptide was probably only present in infected cells. In order to make certain that the peptide was truly absent in the uninfected cells and that there was no chance that our RP-HPLC fractionation had differed (remembering that we use internal controls for our fractionation as well) we generated ion spectra using MS from the fractions before and after the one in which we identified the peptide. In the case of the reticulocalbin peptide, we identified the peptide in fraction 30, so we performed MS on fractions 29 and 31 (FIG. 16) In FIG. 16, it can be seen that there is no substantial peak at the m/z 484.72. This indicated that there was not differential fractionation and that the peptide truly was absent from uninfected cells. In the case that there was a peptide peak in one of the before or after fractions, we would then turn to MS/MS to determine whether this peak represented the ion we were characterizing or another ion with the same mass-to-charge ratio.

Figure 17:
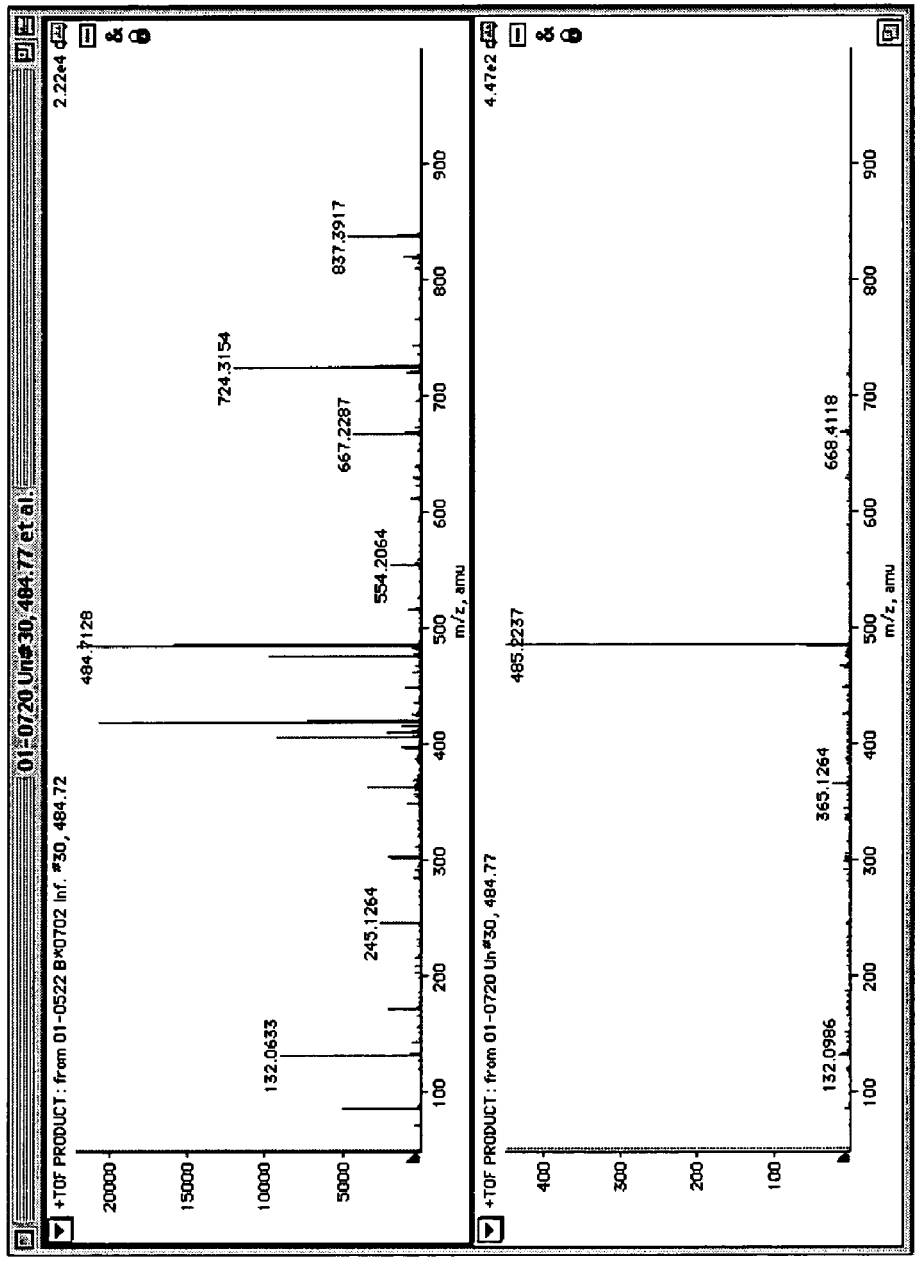
FIG. 17. Fragmentation patterns of soluble B*0702 uninfected SupT1 cells fraction 30 ion 484.72 under identical MS collision conditions to illustrate the absence of the reticulocalbin peptide in the uninfected cells.

After determining that the peptide is not present in another fraction, MS/MS was preformed on the same m/z in the uninfected spectrum (in the same fraction) in order to conclusively prove that there is no peptide present with the same sequence in the uninfected cells. In FIG. 17 one can see that the fragmentation patterns produced under identical MS collision conditions are totally different. This illustrates the absence of the reticulocalbin peptide in the uninfected cells.

Figure 18:
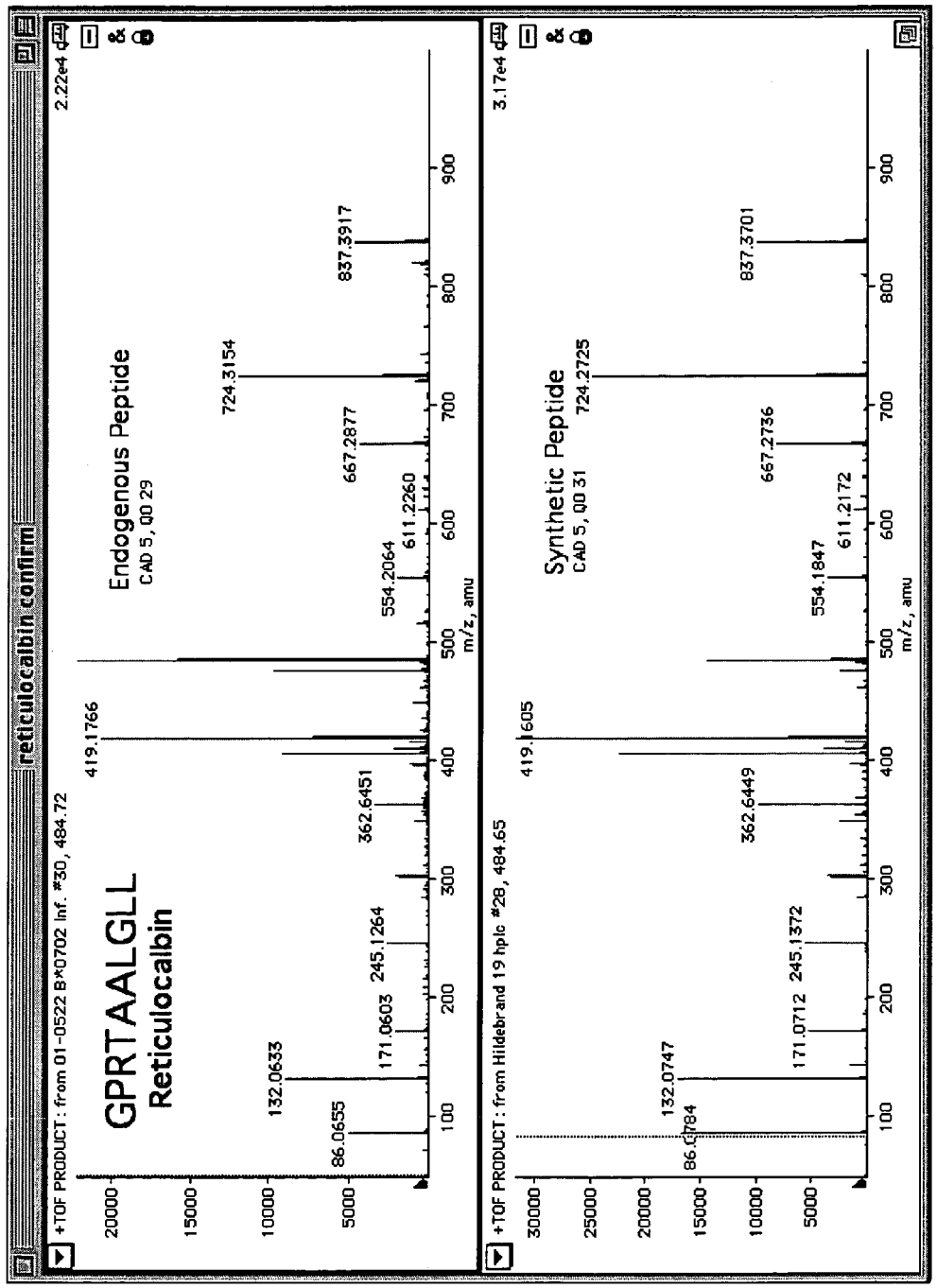
FIG. 18. Comparison of the MS/MS fragmentation patterns of synthetic peptide GPRTAALGLL and peptide ion 484.72 isolated from infected soluble B*0702 SupT1 cells.

Finally, in order to conclusively prove that the peptide sequence is the same as that originally identified, we synthesize synthetic peptides consisting of the same amino acids as the peptide sequence identified from the MS/MS fragmentation pattern. For the reticulocalbin peptide (i.e. the ion in fraction 30 at 484.72) we synthesized the peptide "GPRTAALGLL." (SEQ ID NO:40). We then took this peptide and did MS/MS on the peptide under identical conditions as previously used. FIG. 18 illustrates the spectrum generated from MS/MS of the endogenously loaded reticulocalbin peptide. Matching spectra, as seen here, are indicators that this peptide sequence is GPRTAALGLL (SEQ ID NO:40) as almost every amino acid combination will generate a completely different set of fragments, both in terms of production of fragments and in terms of intensity of those fragments present. FIG. 18 shows the MS/MS endogenous and synthetic "GPRTAALGLL" (SEQ ID NO:40) peptide under identical collision conditions. As can be seen, the MS/MS graphs are virtually identical.

In accordance with the present invention, one peptide ligand (i.e. "GPRTAALGLL"; SEQ ID NO:40) has been identified as being presented by the B*0702 class I MHC molecule in cells infected with the HIV MN-1 virus but not in uninfected cells. As one of ordinary skill in the art can appreciate the novelty and usefulness of the present methodology in directly identifying such peptide ligands and the importance such identification has for numerous therapeutic (vaccine development, drug targeting) and diagnostic tools. As such, numerous other peptide ligands have been uniquely identified in cells infected with HIV MN-1 (as opposed to uninfected cells_ and these results are summarized in TABLE VII. One of ordinary skill in the art given the present specification would be fully enabled to identify the "GPRTAAL-GLL" (SEQ ID NO:40) peptide ligand; as well as other uniquely presented peptide ligands found in cells infected with a microorganism of interest and/or tumorigenic cells.

As stated above, TABLE VII identifies the sequences of peptide ligands identified to date as being unique to HIV infected cells. Class I sHLA B*0702 was harvested for T cells infected and not infected with HIV. Peptide ligands were eluted from B*0702 and comparatively mapped on a mass spectrometer so that ions unique to infected cells were apparent. Ions unique to infected cells (and one ligand unique to uninfected cells) were subjected to mass spectrometric fragmentation for peptide sequencing. Column 1 indicates the ion selected for sequencing, column 2 is the HPLC fraction, column 3 is the peptide sequence, column 4 is the predicted molecular weight, column 5 is the molecular weight we found, column 6 is the source protein for the epitope sequenced, column 7 is where the epitope starts in the sequence of the source protein, column 8 is the accession number, and column 9 is a descriptor which briefly indicates what is known of that epitope and/or its source protein.

The methodology used herein is to use sHLA to determine what is unique to unhealthy cells as compared to healthy cells. Using sHLA to survey the contents of a cell provides a look at what is unique to unhealthy cells in terms of proteins that are processed into peptides. TABLE VII shows the utility of the method described herein for discovering epitopes and their source proteins which are unique to HIV infected cells. A detailed description of the peptide from Reticulocalbin is provided hereinabove. The other epitopes and corresponding source proteins described in TABLE VII were processed in the same manner as the reticulocalbin epitope and source protein were—i.e. as described herein above. The data summarized in TABLE VII shows that the epitope discovery technique described herein is capable of identifying sHLA bound epitopes and their corresponding source proteins which are unique to infected/unhealthy cells.

Likewise, and as is shown in TABLE VII, peptide ligands presented in individual class I MHC molecules in an uninfected cell that are not presented by individual class I MHC molecules in an uninfected cell can also be identified. The peptide "GSHSMRY" (SEQ ID NO:42), for example, was identified by the method of the present invention as being an individual class I MHC molecule which is presented in an uninfected cell but not in an infected cell.

The utility of this data is at least threefold. First, the data indicates what comes out of the cell with HLA. Such data can be used to target CTL to unhealthy cells. Second, antibodies can be targeted to specifically recognize HLA molecules carrying the ligand described. Third, realization of the source protein can lead to therapies and diagnostics which target the source protein. Thus, an epitope unique to unhealthy cells also indicates that the source protein is unique in the unhealthy cell.

The methods of epitope discovery and comparative ligand mapping described herein are not limited to cells infected by a microorganism such as HIV. Unhealthy cells analyzed by the epitope discovery process described herein can arise from virus infection or also cancerous transformation. In addition, the status of an unhealthy cell can also be mimicked by transfecting a particular gene known to be expressed during viral infection or tumor formation. For example, particular genes of HIV can be expressed in a cell line as described (Achour, A., et al., AIDS Res Hum Retroviruses, 1994. 10(1): p. 19-25; and Chiba, M., et al., CTL. Arch Virol, 1999. 144(8): p. 1469-85, all of which are expressly incorporated herein by reference) and then the epitope discovery process performed to identify how the expression of the transferred gene modifies epitope presentation by sHLA. In a similar fashion, genes known to be upregulated during cancer (Smith, E. S., et al., Nat Med, 2001. 7(8): p. 967-72, which is expressly incorporated herein by reference) can be transferred in cells with sHLA and epitope discovery then completed. Thus, epitope discovery with sHLA as described herein can be completed on cells infected with intact pathogens, cancerous cells or cell lines, or cells into which a particular cancer, viral, or bacterial gene has been transferred. In all these instances the sHLA described here will provide a means for detecting what changes in terms of epitope presentation and the source proteins for the epitopes.

Thus, in accordance with the present invention, there has been provided a methodology for epitope discovery and comparative ligand mapping which includes methodology for producing and manipulating Class I and Class II MHC molecules from gDNA that fully satisfies the objectives and advantages set forth herein above. Although the invention has been described in conjunction with the specific drawings, experimentation, results and language set forth herein above, it is evident that many alternatives, modifications, and variations will be apparent to those skilled in the art. Accordingly, it is intended to embrace all such alternatives, modifications and variations that fall within the spirit and broad scope of the invention.

What is claimed is:

1. An isolated peptide ligand for an individual class I MHC molecule, the peptide consisting of a sequence selected from the group consisting of SEQ ID NOS: 29-32 and 34-41 and being isolated by a method comprising the steps of:
   providing a cell line containing a construct that encodes an individual soluble class I MHC molecule, the cell line being able to naturally process proteins into peptide ligands capable of being loaded into antigen binding grooves of class I MHC molecules;
   culturing the cell line under conditions which allow for expression of the individual soluble class I MHC molecules from the construct, such conditions also allowing for endogenous loading of a peptide ligand into the antigen binding groove of each individual soluble class I MHC molecule prior to secretion of the individual soluble class I MHG molecules from the cell;
   isolating the secreted individual soluble class I MHC molecules having the endogenously loaded peptide ligands bound thereto; and
   separating the peptide ligands from the individual soluble class I MHC molecules.

2. An isolated peptide ligand for an individual class I MHC molecule consisting of a fragment of SEQ ID NO:46 comprising the peptide of SEQ ID NO:36.

3. The isolated peptide ligand of claim 2, wherein the isolated peptide ligand is obtained from EUK, Translation Initiation Factor 4.

4. An isolated peptide ligand for an individual class I MHC molecule, wherein the isolated peptide ligand is an endogenously loaded peptide ligand presented by an individual class I MHC molecule on an infected cell but not on an uninfected cell, and wherein the isolated peptide ligand consists of a sequence selected from the group consisting of SEQ ID NOS: 29-32 and 34-41.

5. An isolated peptide ligand identified as being presented by an individual class I MHC molecule on an infected cell but not on an uninfected cell, the isolated peptide ligand consisting of a sequence selected from the group consisting of SEQ ID NOS: 29-32 and 34-41 and being identified by a method comprising the steps of:
   providing an uninfected cell line containing a construct that encodes an individual soluble class I MHC molecule, the cell line being able to naturally process proteins into peptide ligands capable of being loaded into antigen binding grooves of class I MHC molecules;
   infecting a portion of the uninfected cell line with at least one of a microorganism and a gene from a microorganism, thereby providing an infected cell line;
   culturing the uninfected cell line and the infected cell line under conditions which allow for expression of the individual soluble class I MHC molecules from the construct, such conditions also allowing for endogenous loading of a peptide ligand in the antigen binding groove of each individual soluble class I MHC molecule prior to secretion of the individual soluble class I MHC molecules from the cell;
   isolating the secreted individual soluble class I MHC molecules having the endogenously loaded peptide ligands bound thereto from the uninfected cell line and the infected cell line;
   separating the endogenously loaded peptide ligands from the individual soluble class I MHC molecules from the uninfected cell and the endogenously loaded peptide ligands from the individual soluble class I MHC molecules from the infected cell;
   isolating the endogenously loaded peptide ligands from the uninfected cell line and the endogenously loaded peptide ligands from the infected cell line;

comparing the endogenously loaded peptide ligands isolated from the infected cell line to the endogenously loaded peptide ligands isolated from the uninfected cell line; and identifying at least one endogenously loaded peptide ligand presented by the individual soluble class I MHC molecule on the infected cell line that is not presented by the individual soluble class I MHC molecule on the uninfected cell line.

6. The isolated peptide ligand of claim 5 wherein, in the step of providing an uninfected cell line containing a construct that encodes an individual soluble class I MHC molecule, the uninfected cell line containing the construct that encodes the individual soluble class I MHC molecule is produced by a method comprising the steps of:

obtaining genomic DNA or cDNA encoding at least one class I MHC molecule;

identifying an allele encoding an individual class I MHC molecule in the genomic DNA or cDNA;

PCR amplifying the allele encoding the individual class I MHC molecule in a locus specific manner such that a PCR product produced therefrom encodes a truncated, soluble form of the individual class I MHC molecule;

cloning the PCR product into an expression vector, thereby forming a construct that encodes the individual soluble class I MHC molecule; and transfecting the construct into an uninfected cell line.

7. The isolated peptide ligand of claim 6, wherein the construct further encodes a tag which is attached to the individual soluble class I MHC molecule and aids in isolating the individual soluble class I MHC molecule.

8. The isolated peptide ligand of claim 7, wherein the tag is selected from the group consisting of a HIS tail and a FLAG tail.

9. The isolated peptide ligand of claim 7, wherein the tag is encoded by a PCR primer utilized in the step of PCR amplifying the allele encoding the individual class I MHC molecule.

10. The isolated peptide ligand of claim 7, wherein the tag is encoded by the expression vector into which the PCR product is cloned.

11. The isolated peptide ligand of claim 5, wherein the at least one endogenously loaded peptide ligand is obtained from a protein encoded by a gene from the microorganism with which the portion of the uninfected cell line is infected to form the infected cell line.

12. The isolated peptide ligand of claim 5, wherein the at least one endogenously loaded peptide ligand is obtained from a protein encoded by the uninfected cell line.

13. The isolated peptide ligand of claim 5, wherein the portion of the uninfected cell line is infected with HIV.

14. An isolated peptide ligand for an individual class I MHC molecule, wherein the isolated peptide ligand is an endogenously loaded peptide ligand presented by an individual class I MHC molecule on an infected cell but not on an uninfected cell, and wherein the isolated peptide ligand consists of a fragment of SEQ ID NO:46 comprising the peptide of SEQ ID NO:36.

15. An isolated peptide ligand for an individual class I MHC molecule, wherein the isolated peptide ligand is an endogenously loaded peptide ligand presented by an individual class I MHC molecule on an infected cell but not on an uninfected cell, and wherein the isolated, endogenously loaded peptide ligand consists of SEQ ID NO:36.

* * * * *

UNITED STATES PATENT AND TRADEMARK OFFICE
CERTIFICATE OF CORRECTION

PATENT NO. : 7,541,429 B2  Page 1 of 1
APPLICATION NO. : 09/974366
DATED : June 2, 2009
INVENTOR(S) : William H. Hildebrand and Heather D. Hickman It is certified that error appears in the above-identified patent and that said Letters Patent is hereby corrected as shown below:

Column 89, line 48: After "soluble class I" delete "MHG" and replace with -- MHC --.

Signed and Sealed this

Fourth Day of August, 2009

JOHN DOLL
*Acting Director of the United States Patent and Trademark Office*

SEQUENCE LISTING

<160> NUMBER OF SEQ ID NOS: 55

<210> SEQ ID NO 1
<211> LENGTH: 30
<212> TYPE: DNA
<213> ORGANISM: Artificial Sequence
<220> FEATURE:
<223> OTHER INFORMATION: Primer PP5UTA

<400> SEQUENCE: 1
gcgctctaga cccagacgcc gaggatggcc                                      30

<210> SEQ ID NO 2
<211> LENGTH: 20
<212> TYPE: DNA
<213> ORGANISM: Artificial Sequence
<220> FEATURE:
<223> OTHER INFORMATION: Primer 3PPI4A

<400> SEQUENCE: 2
gccctgaccc tgctaaaggt                                                 20

<210> SEQ ID NO 3
<211> LENGTH: 32
<212> TYPE: DNA

-continued

<213> ORGANISM: Artificial Sequence
<220> FEATURE:
<223> OTHER INFORMATION: Primer PP5UTB

<400> SEQUENCE: 3
gcgctctaga ccacccggac tcagaatctc ct                32

<210> SEQ ID NO 4
<211> LENGTH: 20
<212> TYPE: DNA
<213> ORGANISM: Artificial Sequence
<220> FEATURE:
<223> OTHER INFORMATION: Primer 3PPI4B

<400> SEQUENCE: 4
tgctttccct gagaagagat                              20

<210> SEQ ID NO 5
<211> LENGTH: 29
<212> TYPE: DNA
<213> ORGANISM: Artificial Sequence
<220> FEATURE:
<223> OTHER INFORMATION: Primer 5UTB39

<400> SEQUENCE: 5
aggcgaattc cagagtctcc tcagacgcg                    29

<210> SEQ ID NO 6
<211> LENGTH: 38
<212> TYPE: DNA
<213> ORGANISM: Artificial Sequence
<220> FEATURE:
<223> OTHER INFORMATION: Primer 5PKCE

<400> SEQUENCE: 6
gggcgaattc ccgccgccac catgcgggtc atggcgcc          38

<210> SEQ ID NO 7
<211> LENGTH: 20
<212> TYPE: DNA
<213> ORGANISM: Artificial Sequence
<220> FEATURE:
<223> OTHER INFORMATION: Primer 3PPI4C

<400> SEQUENCE: 7
ttctgctttc ctgagaagac                              20

<210> SEQ ID NO 8
<211> LENGTH: 37
<212> TYPE: DNA
<213> ORGANISM: Artificial Sequence
<220> FEATURE:
<223> OTHER INFORMATION: Primer PP5UT

<400> SEQUENCE: 8
gggcgaattc ggactcagaa tctccccaga cgccgag           37

<210> SEQ ID NO 9
<211> LENGTH: 30
<212> TYPE: DNA
<213> ORGANISM: Artificial Sequence
<220> FEATURE:
<223> OTHER INFORMATION: Primer PP3PEI

<400> SEQUENCE: 9
ccgcgaattc tcatctcagg gtgaggggct                   30

```
<210> SEQ ID NO 10
<211> LENGTH: 30
<212> TYPE: DNA
<213> ORGANISM: Artificial Sequence
<220> FEATURE:
<223> OTHER INFORMATION: Primer PP3PEIH

<400> SEQUENCE: 10
ccgcaagctt tcatctcagg gtgaggggct                                    30

<210> SEQ ID NO 11
<211> LENGTH: 30
<212> TYPE: DNA
<213> ORGANISM: Artificial Sequence
<220> FEATURE:
<223> OTHER INFORMATION: Primer 3PEIHC7

<400> SEQUENCE: 11
ccgcaagctt tcagctcagg gtgaggggct                                    30

<210> SEQ ID NO 12
<211> LENGTH: 20
<212> TYPE: DNA
<213> ORGANISM: Artificial Sequence
<220> FEATURE:
<223> OTHER INFORMATION: Primer T7Prom

<400> SEQUENCE: 12
taatacgact cactataggg                                               20

<210> SEQ ID NO 13
<211> LENGTH: 18
<212> TYPE: DNA
<213> ORGANISM: Artificial Sequence
<220> FEATURE:
<223> OTHER INFORMATION: Primer BGHrev

<400> SEQUENCE: 13
tagaaggcac agtcgagg                                                 18

<210> SEQ ID NO 14
<211> LENGTH: 17
<212> TYPE: DNA
<213> ORGANISM: Artificial Sequence
<220> FEATURE:
<223> OTHER INFORMATION: Primer PPI2E2R

<400> SEQUENCE: 14
gtcgtgacct gcgcccc                                                  17

<210> SEQ ID NO 15
<211> LENGTH: 21
<212> TYPE: DNA
<213> ORGANISM: Artificial Sequence
<220> FEATURE:
<223> OTHER INFORMATION: Primer PPI2E2F

<400> SEQUENCE: 15
tttcattttc agtttaggcc a                                             21

<210> SEQ ID NO 16
<211> LENGTH: 19
<212> TYPE: DNA
<213> ORGANISM: Artificial Sequence
<220> FEATURE:
```

<223> OTHER INFORMATION: Primer ABCI3E4F

<400> SEQUENCE: 16
ggtgtcctgt ccattctca							19

<210> SEQ ID NO 17
<211> LENGTH: 37
<212> TYPE: DNA
<213> ORGANISM: Artificial Sequence
<220> FEATURE:
<223> OTHER INFORMATION: Primer HLA5UT

<400> SEQUENCE: 17
gggcgtcgac ggactcagaa tctccccaga cgccgag					37

<210> SEQ ID NO 18
<211> LENGTH: 30
<212> TYPE: DNA
<213> ORGANISM: Artificial Sequence
<220> FEATURE:
<223> OTHER INFORMATION: Primer 5UTA

<400> SEQUENCE: 18
gcgcgtcgac cccagacgcc gaggatggcc						30

<210> SEQ ID NO 19
<211> LENGTH: 37
<212> TYPE: DNA
<213> ORGANISM: Artificial Sequence
<220> FEATURE:
<223> OTHER INFORMATION: Primer 5PXI

<400> SEQUENCE: 19
gggctctaga ggactcagaa tctccccaga cgccgag					37

<210> SEQ ID NO 20
<211> LENGTH: 36
<212> TYPE: DNA
<213> ORGANISM: Artificial Sequence
<220> FEATURE:
<223> OTHER INFORMATION: Primer CLSP23

<400> SEQUENCE: 20
ccgcgtcgac tcagattctc cccagacgcc gagatg					36

<210> SEQ ID NO 21
<211> LENGTH: 28
<212> TYPE: DNA
<213> ORGANISM: Artificial Sequence
<220> FEATURE:
<223> OTHER INFORMATION: Primer LDC3UTA

<400> SEQUENCE: 21
ccgcaagctt agaaacaaag tcagggtt						28

<210> SEQ ID NO 22
<211> LENGTH: 37
<212> TYPE: DNA
<213> ORGANISM: Artificial Sequence
<220> FEATURE:
<223> OTHER INFORMATION: Primer CLSP1085

<400> SEQUENCE: 22
ccgcaagctt ggcagctgtc tcaggcttta caagctg					37

-continued

<210> SEQ ID NO 23
<211> LENGTH: 41
<212> TYPE: DNA
<213> ORGANISM: Artificial Sequence
<220> FEATURE:
<223> OTHER INFORMATION: Primer 3UTA

<400> SEQUENCE: 23
ccgcaagctt ttggggaggg agcacaggtc agcgtgggaa g                41

<210> SEQ ID NO 24
<211> LENGTH: 41
<212> TYPE: DNA
<213> ORGANISM: Artificial Sequence
<220> FEATURE:
<223> OTHER INFORMATION: Primer 3UTB

<400> SEQUENCE: 24
ccgcaagctt ctggggagga aacataggtc agcatgggaa c                41

<210> SEQ ID NO 25
<211> LENGTH: 25
<212> TYPE: DNA
<213> ORGANISM: Artificial Sequence
<220> FEATURE:
<223> OTHER INFORMATION: Primer 3PEI

<400> SEQUENCE: 25
ccgcgaattc tcatctcagg gtgag                                  25

<210> SEQ ID NO 26
<211> LENGTH: 46
<212> TYPE: DNA
<213> ORGANISM: Artificial Sequence
<220> FEATURE:
<223> OTHER INFORMATION: Primer 3PEIHIS

<400> SEQUENCE: 26
ccgcgaattc tcagtggtgg tggtggtggt gccatctcag ggtgag           46

<210> SEQ ID NO 27
<211> LENGTH: 51
<212> TYPE: DNA
<213> ORGANISM: Artificial Sequence
<220> FEATURE:
<223> OTHER INFORMATION: Primer 3PEIFLAG

<400> SEQUENCE: 27
ccgcgattct cacttgtcat cgtcgtcctt gtaatcccat ctcagggtga g     51

<210> SEQ ID NO 28
<211> LENGTH: 38
<212> TYPE: DNA
<213> ORGANISM: Artificial Sequence
<220> FEATURE:
<223> OTHER INFORMATION: Primer 5PKOZXB

<400> SEQUENCE: 28
gggctctaga ccgccgccac catgcgggtc atggcgcc                    38

<210> SEQ ID NO 29
<211> LENGTH: 10
<212> TYPE: PRT
<213> ORGANISM: Human immunodeficiency virus

<400> SEQUENCE: 29

```
Glu Gln Met Phe Glu Asp Ile Ile Ser Leu
1               5                   10

<210> SEQ ID NO 30
<211> LENGTH: 9
<212> TYPE: PRT
<213> ORGANISM: Homo sapiens

<400> SEQUENCE: 30

Ile Pro Cys Leu Leu Ile Ser Phe Leu
1               5

<210> SEQ ID NO 31
<211> LENGTH: 10
<212> TYPE: PRT
<213> ORGANISM: Homo sapiens

<400> SEQUENCE: 31

Ser Thr Thr Ala Ile Cys Ala Thr Gly Leu
1               5                   10

<210> SEQ ID NO 32
<211> LENGTH: 8
<212> TYPE: PRT
<213> ORGANISM: Homo sapiens

<400> SEQUENCE: 32

Ala Pro Ala Gln Asn Pro Glu Leu
1               5

<210> SEQ ID NO 33
<211> LENGTH: 9
<212> TYPE: PRT
<213> ORGANISM: Homo sapiens

<400> SEQUENCE: 33

Leu Val Met Ala Pro Arg Thr Val Leu
1               5

<210> SEQ ID NO 34
<211> LENGTH: 10
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa = any amino acid

<400> SEQUENCE: 34

Ala Pro Phe Ile Asn Ser Pro Ala Asp Xaa
1               5                   10

<210> SEQ ID NO 35
<211> LENGTH: 9
<212> TYPE: PRT
<213> ORGANISM: Homo sapiens

<400> SEQUENCE: 35

Thr Pro Gln Ser Asn Arg Pro Val Met
1               5

<210> SEQ ID NO 36
<211> LENGTH: 9
<212> TYPE: PRT
<213> ORGANISM: Homo sapiens
```

```
<400> SEQUENCE: 36

Ala Ala Arg Pro Ala Thr Ser Thr Leu
1               5

<210> SEQ ID NO 37
<211> LENGTH: 9
<212> TYPE: PRT
<213> ORGANISM: Homo sapiens

<400> SEQUENCE: 37

Met Ala Met Met Ala Ala Leu Met Ala
1               5

<210> SEQ ID NO 38
<211> LENGTH: 9
<212> TYPE: PRT
<213> ORGANISM: Homo sapiens

<400> SEQUENCE: 38

Ile Ala Thr Val Asp Ser Tyr Val Ile
1               5

<210> SEQ ID NO 39
<211> LENGTH: 11
<212> TYPE: PRT
<213> ORGANISM: Homo sapiens

<400> SEQUENCE: 39

Ser Pro Asn Gln Ala Arg Ala Gln Ala Ala Leu
1               5                   10

<210> SEQ ID NO 40
<211> LENGTH: 10
<212> TYPE: PRT
<213> ORGANISM: Homo sapiens

<400> SEQUENCE: 40

Gly Pro Arg Thr Ala Ala Leu Gly Leu Leu
1               5                   10

<210> SEQ ID NO 41
<211> LENGTH: 10
<212> TYPE: PRT
<213> ORGANISM: Homo sapiens

<400> SEQUENCE: 41

Asn Pro Asn Gln Asn Lys Asn Val Ala Leu
1               5                   10

<210> SEQ ID NO 42
<211> LENGTH: 7
<212> TYPE: PRT
<213> ORGANISM: Homo sapiens

<400> SEQUENCE: 42

Gly Ser His Ser Met Arg Tyr
1               5

<210> SEQ ID NO 43
<211> LENGTH: 521
<212> TYPE: PRT
<213> ORGANISM: Homo sapiens

<400> SEQUENCE: 43
```

```
Met Glu Cys Pro His Leu Ser Ser Ser Val Cys Ile Ala Pro Asp Ser
 1               5                  10                  15

Ala Lys Phe Pro Asn Gly Ser Pro Ser Ser Trp Cys Ser Cys Val Cys
             20                  25                  30

Arg Ser Asn Lys Ser Pro Trp Val Cys Leu Thr Cys Ser Ser Val His
         35                  40                  45

Cys Gly Arg Tyr Val Asn Gly His Ala Lys Lys His Tyr Glu Asp Ala
     50                  55                  60

Gln Val Pro Leu Thr Asn His Lys Lys Ser Glu Lys Gln Asp Lys Val
 65                  70                  75                  80

Gln His Thr Val Cys Met Asp Cys Ser Ser Tyr Ser Tyr Cys Tyr
                 85                  90                  95

Arg Cys Asp Asp Phe Val Val Asn Asp Thr Lys Leu Gly Leu Val Gln
             100                 105                 110

Lys Val Arg Glu His Leu Gln Asn Leu Glu Asn Ser Ala Phe Thr Ala
         115                 120                 125

Asp Arg His Lys Lys Arg Lys Leu Leu Glu Asn Ser Thr Leu Asn Ser
     130                 135                 140

Lys Leu Leu Lys Val Asn Gly Ser Thr Thr Ala Ile Cys Ala Thr Gly
145                 150                 155                 160

Leu Arg Asn Leu Gly Asn Thr Cys Phe Met Asn Ala Ile Leu Gln Ser
                 165                 170                 175

Leu Ser Asn Ile Glu Gln Phe Cys Cys Tyr Phe Lys Glu Leu Pro Ala
             180                 185                 190

Val Glu Leu Arg Asn Gly Lys Thr Ala Gly Arg Thr Tyr His Thr
         195                 200                 205

Arg Ser Gln Gly Asp Asn Val Ser Leu Val Glu Glu Phe Arg Lys
 210                 215                 220

Thr Leu Cys Ala Leu Trp Gln Gly Ser Gln Thr Ala Phe Ser Pro Glu
225                 230                 235                 240

Ser Leu Phe Tyr Val Val Trp Lys Ile Met Pro Asn Phe Arg Gly Tyr
                 245                 250                 255

Gln Gln Gln Asp Ala His Glu Phe Asn Ala Leu Pro Phe Gly Pro Pro
             260                 265                 270

Thr Leu Gly Asn Phe Arg Ala Val Ser Thr Val Phe Pro Ala Gln Gln
         275                 280                 285

Phe Cys Arg Arg Ile Leu Leu Cys Leu Gln Val Asn Lys Cys Cys Ile
 290                 295                 300

Asn Gly Ala Ser Thr Val Thr Ala Ile Phe Gly Gly Ile Leu Gln
305                 310                 315                 320

Asn Glu Val Asn Cys Leu Ile Cys Gly Thr Glu Ser Arg Lys Phe Asp
                 325                 330                 335

Pro Phe Leu Asp Leu Ser Leu Asp Ile Pro Ser Gln Phe Arg Ser Lys
             340                 345                 350

Arg Ser Lys Asn Gln Glu Asn Gly Pro Val Cys Ser Leu Arg Asp Cys
         355                 360                 365

Leu Arg Ser Phe Thr Asp Leu Glu Glu Leu Asp Glu Thr Glu Leu Tyr
     370                 375                 380

Met Cys His Lys Cys Lys Lys Gln Lys Ser Thr Lys Lys Phe Trp
385                 390                 395                 400

Ile Gln Lys Leu Pro Lys Val Leu Cys Leu His Leu Lys Arg Phe His
             405                 410                 415

Trp Thr Ala Tyr Leu Arg Asn Lys Val Asp Thr Tyr Val Glu Phe Pro
```

420                 425                 430
Leu Arg Gly Leu Asp Met Lys Trp Tyr Leu Glu Pro Glu Asn Ser
            435                 440                 445

Gly Pro Glu Ser Cys Leu Tyr Asp Leu Ala Ala Val Val His His
            450                 455                 460

Gly Ser Gly Val Gly Ser Gly His Tyr Thr Ala Tyr Ala Thr His Glu
465                 470                 475                 480

Gly Arg Trp Phe His Phe Asn Asp Ser Thr Val Thr Leu Thr Asp Glu
                        485                 490                 495

Glu Thr Val Val Lys Ala Lys Ala Tyr Ile Leu Phe Tyr Val Glu His
                500                 505                 510

Gln Ala Lys Ala Gly Ser Asp Lys Leu
            515                 520

<210> SEQ ID NO 44
<211> LENGTH: 206
<212> TYPE: PRT
<213> ORGANISM: Homo sapiens

<400> SEQUENCE: 44

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Cys Lys Thr Asn Thr Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly Tyr Asn Gln Phe Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Thr Cys Val Glu Trp Leu
            180                 185                 190

Arg Arg His Leu Glu Asn Gly Lys Glu Thr Leu Gln Arg Ala
        195                 200                 205

<210> SEQ ID NO 45
<211> LENGTH: 1970
<212> TYPE: PRT
<213> ORGANISM: Homo sapiens

<400> SEQUENCE: 45

Met His Gly Gly Gly Pro Pro Ser Gly Asp Ser Ala Cys Pro Leu Arg
1               5                   10                  15

Thr Ile Lys Arg Val Gln Phe Gly Val Leu Ser Pro Asp Glu Leu Lys

-continued

```
                    20                  25                  30
Arg Met Ser Val Thr Glu Gly Gly Ile Lys Tyr Pro Glu Thr Thr Glu
                35                  40                  45
Gly Gly Arg Pro Lys Leu Gly Gly Leu Met Asp Pro Arg Gln Gly Val
            50                  55                  60
Ile Glu Arg Thr Gly Arg Cys Gln Thr Cys Ala Gly Asn Met Thr Glu
65                  70                  75                  80
Cys Pro Gly His Phe Gly His Ile Glu Leu Ala Lys Pro Val Phe His
                    85                  90                  95
Val Gly Phe Leu Val Lys Thr Met Lys Val Leu Arg Cys Val Cys Phe
                100                 105                 110
Phe Cys Ser Lys Leu Leu Val Asp Ser Asn Asn Pro Lys Ile Lys Asp
                115                 120                 125
Ile Leu Ala Lys Ser Lys Gly Gln Pro Lys Lys Arg Leu Thr His Val
            130                 135                 140
Tyr Asp Leu Cys Lys Gly Lys Asn Ile Cys Glu Gly Gly Glu Glu Met
145                 150                 155                 160
Asp Asn Lys Phe Gly Val Glu Gln Pro Glu Gly Asp Glu Asp Leu Thr
                165                 170                 175
Lys Glu Lys Gly His Gly Gly Cys Gly Arg Tyr Gln Pro Arg Ile Arg
                180                 185                 190
Arg Ser Gly Leu Glu Leu Tyr Ala Glu Trp Lys His Val Asn Glu Asp
            195                 200                 205
Ser Gln Glu Lys Lys Ile Leu Leu Ser Pro Arg Val His Glu Ile
            210                 215                 220
Phe Lys Arg Ile Ser Asp Glu Glu Cys Phe Val Leu Gly Met Glu Pro
225                 230                 235                 240
Arg Tyr Ala Arg Pro Glu Trp Met Ile Val Thr Val Leu Pro Val Pro
                245                 250                 255
Pro Leu Ser Val Arg Pro Ala Val Val Met Gln Gly Ser Ala Arg Asn
                260                 265                 270
Gln Asp Asp Leu Thr His Lys Leu Ala Asp Ile Val Lys Ile Asn Asn
            275                 280                 285
Gln Leu Arg Arg Asn Glu Gln Asn Gly Ala Ala Ala His Val Ile Ala
        290                 295                 300
Glu Asp Val Lys Leu Leu Gln Phe His Val Ala Thr Met Val Asp Asn
305                 310                 315                 320
Glu Leu Pro Gly Leu Pro Arg Ala Met Gln Lys Ser Gly Arg Pro Leu
                325                 330                 335
Lys Ser Leu Lys Gln Arg Leu Lys Gly Lys Glu Gly Arg Val Arg Gly
                340                 345                 350
Asn Leu Met Gly Lys Arg Val Asp Phe Ser Ala Arg Thr Val Ile Thr
            355                 360                 365
Pro Asp Pro Asn Leu Ser Ile Asp Gln Val Gly Val Pro Arg Ser Ile
        370                 375                 380
Ala Ala Asn Met Thr Phe Ala Glu Ile Val Thr Pro Phe Asn Ile Asp
385                 390                 395                 400
Arg Leu Gln Glu Leu Val Arg Arg Gly Asn Ser Gln Tyr Pro Gly Ala
                405                 410                 415
Lys Tyr Ile Ile Arg Asp Asn Gly Asp Arg Ile Asp Leu Arg Phe His
                420                 425                 430
Pro Lys Pro Ser Asp Leu His Leu Gln Thr Gly Tyr Lys Val Glu Arg
            435                 440                 445
```

-continued

His Met Cys Asp Gly Asp Ile Val Ile Phe Asn Arg Gln Pro Thr Leu
450                 455                 460

His Lys Met Ser Met Met Gly His Arg Val Arg Ile Leu Pro Trp Ser
465                 470                 475                 480

Thr Phe Arg Leu Asn Leu Ser Val Thr Thr Pro Tyr Asn Ala Asp Phe
            485                 490                 495

Asp Gly Asp Glu Met Asn Leu His Leu Pro Gln Ser Leu Glu Thr Arg
            500                 505                 510

Ala Glu Ile Gln Glu Leu Ala Met Val Pro Arg Met Ile Val Thr Pro
            515                 520                 525

Gln Ser Asn Arg Pro Val Met Gly Ile Val Gln Asp Thr Leu Thr Ala
530                 535                 540

Val Arg Lys Phe Thr Lys Arg Asp Val Phe Leu Glu Arg Gly Glu Val
545                 550                 555                 560

Met Asn Leu Leu Met Phe Leu Ser Thr Trp Asp Gly Lys Val Pro Gln
                565                 570                 575

Pro Ala Ile Leu Lys Pro Arg Pro Leu Trp Thr Gly Lys Gln Ile Phe
            580                 585                 590

Ser Leu Ile Ile Pro Gly His Ile Asn Cys Ile Arg Thr His Ser Thr
            595                 600                 605

His Pro Asp Asp Glu Asp Ser Gly Pro Tyr Lys His Ile Ser Pro Gly
610                 615                 620

Asp Thr Lys Val Val Glu Asn Gly Glu Leu Ile Met Gly Ile Leu
625                 630                 635                 640

Cys Lys Lys Ser Leu Gly Thr Ser Ala Gly Ser Leu Val His Ile Ser
                645                 650                 655

Tyr Leu Glu Met Gly His Asp Ile Thr Arg Leu Phe Tyr Ser Asn Ile
            660                 665                 670

Gln Thr Val Ile Asn Asn Trp Leu Leu Ile Glu Gly His Thr Ile Gly
            675                 680                 685

Ile Gly Asp Ser Ile Ala Asp Ser Lys Thr Tyr Gln Asp Ile Gln Asn
        690                 695                 700

Thr Ile Lys Lys Ala Lys Gln Asp Val Ile Glu Val Ile Glu Lys Ala
705                 710                 715                 720

His Asn Asn Glu Leu Glu Pro Thr Pro Gly Asn Thr Leu Arg Gln Thr
                725                 730                 735

Phe Glu Asn Gln Val Asn Arg Ile Leu Asn Asp Ala Arg Asp Lys Thr
            740                 745                 750

Gly Ser Ser Ala Gln Lys Ser Leu Ser Glu Tyr Asn Asn Phe Lys Ser
            755                 760                 765

Met Val Val Ser Gly Ala Lys Gly Ser Lys Ile Asn Ile Ser Gln Val
770                 775                 780

Ile Ala Val Val Gly Gln Gln Asn Val Glu Gly Lys Arg Ile Pro Phe
785                 790                 795                 800

Gly Phe Lys His Arg Thr Leu Pro His Phe Ile Lys Asp Asp Tyr Gly
                805                 810                 815

Pro Glu Ser Arg Gly Phe Val Glu Asn Ser Tyr Leu Ala Gly Leu Thr
            820                 825                 830

Pro Thr Glu Phe Phe His Ala Met Gly Gly Arg Glu Gly Leu Ile
            835                 840                 845

Asp Thr Ala Val Lys Thr Ala Glu Thr Gly Tyr Ile Gln Arg Arg Leu
850                 855                 860

-continued

```
Ile Lys Ser Met Glu Ser Val Met Val Lys Tyr Asp Ala Thr Val Arg
865                 870                 875                 880

Asn Ser Ile Asn Gln Val Val Gln Leu Arg Tyr Gly Glu Asp Gly Leu
            885                 890                 895

Ala Gly Glu Ser Val Glu Phe Gln Asn Leu Ala Thr Leu Lys Pro Ser
        900                 905                 910

Asn Lys Ala Phe Glu Lys Lys Phe Arg Phe Asp Tyr Thr Asn Glu Arg
    915                 920                 925

Ala Leu Arg Arg Thr Leu Gln Glu Asp Leu Val Lys Asp Val Leu Ser
930                 935                 940

Asn Ala His Ile Gln Asn Glu Leu Glu Arg Glu Phe Glu Arg Met Arg
945                 950                 955                 960

Glu Asp Arg Glu Val Leu Arg Val Ile Phe Pro Thr Gly Asp Ser Lys
            965                 970                 975

Val Val Leu Pro Cys Asn Leu Leu Arg Met Ile Trp Asn Ala Gln Lys
        980                 985                 990

Ile Phe His Ile Asn Pro Arg Leu Pro Ser Asp Leu His Pro Ile Lys
    995                 1000                1005

Val Val Glu Gly Val Lys Glu Leu Ser Lys Leu Val Ile Val
1010                1015                1020

Asn Gly Asp Asp Pro Leu Ser Arg Gln Ala Gln Glu Asn Ala Thr
1025                1030                1035

Leu Leu Phe Asn Ile His Leu Arg Ser Thr Leu Cys Ser Arg Arg
1040                1045                1050

Met Ala Glu Glu Phe Arg Leu Ser Gly Glu Ala Phe Asp Trp Leu
1055                1060                1065

Leu Gly Glu Ile Glu Ser Lys Phe Asn Gln Ala Ile Ala His Pro
1070                1075                1080

Gly Glu Met Val Gly Ala Leu Ala Ala Gln Ser Leu Gly Glu Pro
1085                1090                1095

Ala Thr Gln Met Thr Leu Asn Thr Phe His Tyr Ala Gly Val Ser
1100                1105                1110

Ala Lys Asn Val Thr Leu Gly Val Pro Arg Leu Lys Glu Leu Ile
1115                1120                1125

Asn Ile Ser Lys Lys Pro Lys Thr Pro Ser Leu Thr Val Phe Leu
1130                1135                1140

Leu Gly Gln Ser Ala Arg Asp Ala Glu Arg Ala Lys Asp Ile Leu
1145                1150                1155

Cys Arg Leu Glu His Thr Thr Leu Arg Lys Val Thr Ala Asn Thr
1160                1165                1170

Ala Ile Tyr Tyr Asp Pro Asn Pro Gln Ser Thr Val Val Ala Glu
1175                1180                1185

Asp Gln Glu Trp Val Asn Val Tyr Tyr Glu Met Pro Asp Phe Asp
1190                1195                1200

Val Ala Arg Ile Ser Pro Trp Leu Leu Arg Val Glu Leu Asp Arg
1205                1210                1215

Lys His Met Thr Asp Arg Lys Leu Thr Met Glu Gln Ile Ala Glu
1220                1225                1230

Lys Ile Asn Ala Gly Phe Gly Asp Asp Leu Asn Cys Ile Phe Asn
1235                1240                1245

Asp Asp Asn Ala Glu Lys Leu Val Leu Arg Ile Arg Ile Met Asn
1250                1255                1260

Ser Asp Glu Asn Lys Met Gln Glu Glu Glu Val Val Asp Lys
```

-continued

```
        1265                1270                1275
Met Asp Asp Asp Val Phe Leu Arg Cys Ile Glu Ser Asn Met Leu
    1280                1285                1290

Thr Asp Met Thr Leu Gln Gly Ile Glu Gln Ile Ser Lys Val Tyr
    1295                1300                1305

Met His Leu Pro Gln Thr Asp Asn Lys Lys Ile Ile Ile Thr
    1310                1315                1320

Glu Asp Gly Glu Phe Lys Ala Leu Gln Glu Trp Ile Leu Glu Thr
    1325                1330                1335

Asp Gly Val Ser Leu Met Arg Val Leu Ser Glu Lys Asp Val Asp
    1340                1345                1350

Pro Val Arg Thr Thr Ser Asn Asp Ile Val Glu Ile Phe Thr Val
    1355                1360                1365

Leu Gly Ile Glu Ala Val Arg Lys Ala Leu Glu Arg Glu Leu Tyr
    1370                1375                1380

His Val Ile Ser Phe Asp Gly Ser Tyr Val Asn Tyr Arg His Leu
    1385                1390                1395

Ala Leu Leu Cys Asp Thr Met Thr Cys Arg Gly His Leu Met Ala
    1400                1405                1410

Ile Thr Arg His Gly Val Asn Arg Gln Asp Thr Gly Pro Leu Met
    1415                1420                1425

Lys Cys Ser Phe Glu Glu Thr Val Asp Val Leu Met Glu Ala Ala
    1430                1435                1440

Ala His Gly Glu Ser Asp Pro Met Lys Gly Val Ser Glu Asn Ile
    1445                1450                1455

Met Leu Gly Gln Leu Ala Pro Ala Gly Thr Gly Cys Phe Asp Leu
    1460                1465                1470

Leu Leu Asp Ala Glu Lys Cys Lys Tyr Gly Met Glu Ile Pro Thr
    1475                1480                1485

Asn Ile Pro Gly Leu Gly Ala Ala Gly Pro Thr Gly Met Phe Phe
    1490                1495                1500

Gly Ser Ala Pro Ser Pro Met Gly Gly Ile Ser Pro Ala Met Thr
    1505                1510                1515

Pro Trp Asn Gln Gly Ala Thr Pro Ala Tyr Gly Ala Trp Ser Pro
    1520                1525                1530

Ser Val Gly Ser Gly Met Thr Pro Gly Ala Ala Gly Phe Ser Pro
    1535                1540                1545

Ser Ala Ala Ser Asp Ala Ser Gly Phe Ser Pro Gly Tyr Ser Pro
    1550                1555                1560

Ala Trp Ser Pro Thr Pro Gly Ser Pro Gly Ser Pro Gly Pro Ser
    1565                1570                1575

Ser Pro Tyr Ile Pro Ser Pro Gly Gly Ala Met Ser Pro Ser Tyr
    1580                1585                1590

Ser Pro Thr Ser Pro Ala Tyr Glu Pro Arg Ser Pro Gly Gly Tyr
    1595                1600                1605

Thr Pro Gln Ser Pro Ser Tyr Ser Pro Thr Ser Pro Ser Tyr Ser
    1610                1615                1620

Pro Thr Ser Pro Ser Tyr Ser Pro Thr Ser Pro Asn Tyr Ser Pro
    1625                1630                1635

Thr Ser Pro Ser Tyr Ser Pro Thr Ser Pro Ser Tyr Ser Pro Thr
    1640                1645                1650

Ser Pro Ser Tyr Ser Pro Thr Ser Pro Ser Tyr Ser Pro Thr Ser
    1655                1660                1665
```

Pro Ser Tyr Ser Pro Thr Ser Pro Ser Tyr Ser Pro Thr Ser Pro
             1670                1675                1680

Ser Tyr Ser Pro Thr Ser Pro Ser Tyr Ser Pro Thr Ser Pro Ser
        1685                1690                1695

Tyr Ser Pro Thr Ser Pro Ser Tyr Ser Pro Thr Ser Pro Ser Tyr
    1700                1705                1710

Ser Pro Thr Ser Pro Ser Tyr Ser Pro Thr Ser Pro Ser Tyr Ser
1715                1720                1725

Pro Thr Ser Pro Ser Tyr Ser Pro Thr Ser Pro Ser Tyr Ser Pro
        1730                1735                1740

Thr Ser Pro Asn Tyr Ser Pro Thr Ser Pro Asn Tyr Thr Pro Thr
            1745                1750                1755

Ser Pro Ser Tyr Ser Pro Thr Ser Pro Ser Tyr Ser Pro Thr Ser
                1760                1765                1770

Pro Asn Tyr Thr Pro Thr Ser Pro Asn Tyr Ser Pro Thr Ser Pro
    1775                1780                1785

Ser Tyr Ser Pro Thr Ser Pro Ser Tyr Ser Pro Thr Ser Pro Ser
        1790                1795                1800

Tyr Ser Pro Ser Ser Pro Arg Tyr Thr Pro Gln Ser Pro Thr Tyr
            1805                1810                1815

Thr Pro Ser Ser Pro Ser Tyr Ser Pro Ser Ser Pro Ser Tyr Ser
    1820                1825                1830

Pro Thr Ser Pro Lys Tyr Thr Pro Thr Ser Pro Ser Tyr Ser Pro
        1835                1840                1845

Ser Ser Pro Glu Tyr Thr Pro Thr Ser Pro Lys Tyr Ser Pro Thr
            1850                1855                1860

Ser Pro Lys Tyr Ser Pro Thr Ser Pro Lys Tyr Ser Pro Thr Ser
                1865                1870                1875

Pro Thr Tyr Ser Pro Thr Thr Pro Lys Tyr Ser Pro Thr Ser Pro
    1880                1885                1890

Thr Tyr Ser Pro Thr Ser Pro Val Tyr Thr Pro Thr Ser Pro Lys
        1895                1900                1905

Tyr Ser Pro Thr Ser Pro Thr Tyr Ser Pro Thr Ser Pro Lys Tyr
            1910                1915                1920

Ser Pro Thr Ser Pro Thr Tyr Ser Pro Thr Ser Pro Lys Gly Ser
                1925                1930                1935

Thr Tyr Ser Pro Thr Ser Pro Gly Tyr Ser Pro Thr Ser Pro Thr
    1940                1945                1950

Tyr Ser Leu Thr Ser Pro Ala Ile Ser Pro Asp Asp Ser Asp Glu
        1955                1960                1965

Glu Asn
    1970

<210> SEQ ID NO 46
<211> LENGTH: 1600
<212> TYPE: PRT
<213> ORGANISM: Homo sapiens

<400> SEQUENCE: 46

Met Asn Lys Ala Pro Gln Ser Thr Gly Pro Pro Ala Pro Ser Pro
1               5                   10                  15

Gly Leu Pro Gln Pro Ala Phe Pro Pro Gly Gln Thr Ala Pro Val Val
                20                  25                  30

Phe Ser Thr Pro Gln Ala Thr Gln Met Asn Thr Pro Ser Gln Pro Arg

-continued

```
                35                  40                  45
Gln His Phe Tyr Pro Ser Arg Ala Gln Pro Ser Ser Ala Ala Ser
        50                  55                  60

Arg Val Gln Ser Ala Ala Pro Ala Arg Pro Gly Pro Ala Ala His Val
 65                  70                  75                  80

Tyr Pro Ala Gly Ser Gln Val Met Met Ile Pro Ser Gln Ile Ser Tyr
                85                  90                  95

Pro Ala Ser Gln Gly Ala Tyr Tyr Ile Pro Gly Gln Gly Arg Ser Thr
            100                 105                 110

Tyr Val Val Pro Thr Gln Gln Tyr Pro Val Gln Pro Gly Ala Pro Gly
            115                 120                 125

Phe Tyr Pro Gly Ala Ser Pro Thr Glu Leu Gly Thr Tyr Ala Gly Ala
        130                 135                 140

Tyr Tyr Pro Ala Arg Gly Val Gln Gln Phe Pro Thr Gly Val Ala Pro
145                 150                 155                 160

Ala Pro Val Leu Met Asn Gln Pro Pro Gln Ile Ala Pro Lys Arg Glu
                165                 170                 175

Arg Lys Thr Ile Arg Ile Arg Asp Pro Asn Gln Gly Gly Lys Asp Ile
            180                 185                 190

Thr Glu Glu Ile Met Ser Gly Ala Arg Thr Ala Ser Thr Pro Thr Pro
            195                 200                 205

Pro Gln Thr Gly Gly Gly Leu Glu Pro Gln Ala Asn Gly Glu Thr Pro
        210                 215                 220

Gln Val Ala Val Ile Val Arg Pro Asp Asp Arg Ser Gln Gly Ala Ile
225                 230                 235                 240

Ile Ala Asp Arg Pro Gly Leu Pro Gly Pro Glu His Ser Pro Ser Glu
                245                 250                 255

Ser Gln Pro Ser Ser Pro Ser Pro Thr Pro Ser Pro Ser Pro Val Leu
            260                 265                 270

Glu Pro Gly Ser Glu Pro Asn Leu Ala Val Leu Ser Ile Pro Gly Asp
            275                 280                 285

Thr Met Thr Thr Ile Gln Met Ser Val Glu Glu Ser Thr Pro Ile Ser
        290                 295                 300

Arg Glu Thr Gly Glu Pro Tyr Arg Leu Ser Pro Glu Pro Thr Pro Leu
305                 310                 315                 320

Ala Glu Pro Ile Leu Glu Val Glu Val Thr Leu Ser Lys Pro Val Pro
                325                 330                 335

Glu Ser Glu Phe Ser Ser Pro Leu Gln Ala Pro Thr Pro Leu Ala
            340                 345                 350

Ser His Thr Val Glu Ile His Glu Pro Asn Gly Met Val Pro Ser Glu
            355                 360                 365

Asp Leu Glu Pro Glu Val Glu Ser Ser Pro Glu Leu Ala Pro Pro Pro
        370                 375                 380

Ala Cys Pro Ser Glu Ser Pro Val Pro Ile Ala Pro Thr Ala Gln Pro
385                 390                 395                 400

Glu Glu Leu Leu Asn Gly Ala Pro Ser Pro Ala Val Asp Leu Ser
                405                 410                 415

Pro Val Ser Glu Pro Glu Glu Gln Ala Lys Glu Val Thr Ala Ser Val
            420                 425                 430

Ala Pro Pro Thr Ile Pro Ser Ala Thr Pro Ala Thr Ala Pro Ser Ala
        435                 440                 445

Thr Ser Pro Ala Gln Glu Glu Glu Met Glu Glu Glu Glu Glu Glu Glu
450                 455                 460
```

-continued

```
Glu Gly Glu Ala Gly Glu Ala Gly Ala Glu Ser Glu Lys Gly Gly
465                 470                 475                 480

Glu Glu Leu Leu Pro Pro Glu Ser Thr Pro Ile Pro Ala Asn Leu Ser
                485                 490                 495

Gln Asn Leu Glu Ala Ala Ala Thr Gln Val Ala Val Ser Val Pro
            500                 505                 510

Lys Arg Arg Arg Lys Ile Lys Glu Leu Asn Lys Lys Glu Ala Val Gly
            515                 520                 525

Asp Leu Leu Asp Ala Phe Lys Glu Ala Asn Pro Ala Val Pro Glu Val
        530                 535                 540

Glu Asn Gln Pro Pro Ala Gly Ser Asn Pro Gly Pro Glu Ser Glu Gly
545                 550                 555                 560

Ser Gly Val Pro Pro Arg Pro Glu Glu Ala Asp Glu Thr Trp Asp Ser
                565                 570                 575

Lys Glu Asp Lys Ile His Asn Ala Glu Asn Ile Gln Pro Gly Glu Gln
            580                 585                 590

Lys Tyr Glu Tyr Lys Ser Asp Gln Trp Lys Pro Pro Asn Leu Glu Glu
        595                 600                 605

Lys Lys Arg Tyr Asp Arg Glu Phe Leu Leu Gly Phe Gln Phe Ile Phe
    610                 615                 620

Ala Ser Met Gln Lys Pro Glu Gly Leu Pro His Ile Ser Asp Val Val
625                 630                 635                 640

Leu Asp Lys Ala Asn Lys Thr Pro Leu Arg Pro Leu Asp Pro Thr Arg
                645                 650                 655

Leu Gln Gly Ile Asn Cys Gly Pro Asp Phe Thr Pro Ser Phe Ala Asn
            660                 665                 670

Leu Gly Arg Thr Thr Leu Ser Thr Arg Gly Pro Pro Arg Gly Gly Pro
        675                 680                 685

Gly Gly Glu Leu Pro Arg Gly Pro Gln Ala Gly Leu Gly Pro Arg Arg
    690                 695                 700

Ser Gln Gln Gly Pro Arg Lys Glu Pro Arg Lys Ile Ile Ala Thr Val
705                 710                 715                 720

Leu Met Thr Glu Asp Ile Lys Leu Asn Lys Ala Glu Lys Ala Trp Lys
                725                 730                 735

Pro Ser Ser Lys Arg Thr Ala Ala Asp Lys Asp Arg Gly Glu Glu Asp
            740                 745                 750

Ala Asp Gly Ser Lys Thr Gln Asp Leu Phe Arg Arg Val Arg Ser Ile
        755                 760                 765

Leu Asn Lys Leu Thr Pro Gln Met Phe Gln Gln Leu Met Lys Gln Val
    770                 775                 780

Thr Gln Leu Ala Ile Asp Thr Glu Glu Arg Leu Lys Gly Val Ile Asp
785                 790                 795                 800

Leu Ile Phe Glu Lys Ala Ile Ser Glu Pro Asn Phe Ser Val Ala Tyr
                805                 810                 815

Ala Asn Met Cys Arg Cys Leu Met Ala Leu Lys Val Pro Thr Thr Glu
            820                 825                 830

Lys Pro Thr Val Thr Val Asn Phe Arg Lys Leu Leu Leu Asn Arg Cys
        835                 840                 845

Gln Lys Glu Phe Glu Lys Asp Lys Asp Asp Glu Val Phe Glu Lys
    850                 855                 860

Lys Gln Lys Glu Met Asp Glu Ala Ala Thr Ala Glu Glu Arg Gly Arg
865                 870                 875                 880
```

-continued

```
Leu Lys Glu Glu Leu Glu Ala Arg Asp Ile Ala Arg Arg Arg Ser
            885                 890                 895
Leu Gly Asn Ile Lys Phe Ile Gly Glu Leu Phe Lys Leu Lys Met Leu
            900                 905                 910
Thr Glu Ala Ile Met His Asp Cys Val Val Lys Leu Leu Lys Asn His
            915                 920                 925
Asp Glu Glu Ser Leu Glu Cys Leu Cys Arg Leu Leu Thr Thr Ile Gly
            930                 935                 940
Lys Asp Leu Asp Phe Glu Lys Ala Lys Pro Arg Met Asp Gln Tyr Phe
945                 950                 955                 960
Asn Gln Met Glu Lys Ile Ile Lys Glu Lys Lys Thr Ser Ser Arg Ile
            965                 970                 975
Arg Phe Met Leu Gln Asp Val Leu Asp Leu Arg Gly Ser Asn Trp Val
            980                 985                 990
Pro Arg Arg Gly Asp Gln Gly Pro Lys Thr Ile Asp Gln Ile His Lys
            995                 1000                1005
Glu Ala Glu Met Glu Glu His Arg Glu His Ile Lys Val Gln Gln
            1010                1015                1020
Leu Met Ala Lys Gly Ser Asp Lys Arg Arg Gly Gly Pro Pro Gly
            1025                1030                1035
Pro Pro Ile Ser Arg Gly Leu Pro Leu Val Asp Asp Gly Gly Trp
            1040                1045                1050
Asn Thr Val Pro Ile Ser Lys Gly Ser Arg Pro Ile Asp Thr Ser
            1055                1060                1065
Arg Leu Thr Lys Ile Thr Lys Pro Gly Ser Ile Asp Ser Asn Asn
            1070                1075                1080
Gln Leu Phe Ala Pro Gly Gly Arg Leu Ser Trp Gly Lys Gly Ser
            1085                1090                1095
Ser Gly Gly Ser Gly Ala Lys Pro Ser Asp Ala Ala Ser Glu Ala
            1100                1105                1110
Ala Arg Pro Ala Thr Ser Thr Leu Asn Arg Phe Ser Ala Leu Gln
            1115                1120                1125
Gln Ala Val Pro Thr Glu Ser Thr Asp Asn Arg Arg Val Val Gln
            1130                1135                1140
Arg Ser Ser Leu Ser Arg Glu Arg Gly Glu Lys Ala Gly Asp Arg
            1145                1150                1155
Gly Asp Arg Leu Glu Arg Ser Glu Arg Gly Gly Asp Arg Gly Asp
            1160                1165                1170
Arg Leu Asp Arg Ala Arg Thr Pro Ala Thr Lys Arg Ser Phe Ser
            1175                1180                1185
Lys Glu Val Glu Glu Arg Ser Arg Glu Arg Pro Ser Gln Pro Glu
            1190                1195                1200
Gly Leu Arg Lys Ala Ala Ser Leu Thr Glu Asp Arg Asp Arg Gly
            1205                1210                1215
Arg Asp Ala Val Lys Arg Glu Ala Ala Leu Pro Pro Val Ser Pro
            1220                1225                1230
Leu Lys Ala Ala Leu Ser Glu Glu Leu Glu Lys Lys Ser Lys
            1235                1240                1245
Ala Ile Ile Glu Glu Tyr Leu His Leu Asn Asp Met Lys Glu Ala
            1250                1255                1260
Val Gln Cys Val Gln Glu Leu Ala Ser Pro Ser Leu Leu Phe Ile
            1265                1270                1275
Phe Val Arg His Gly Val Glu Ser Thr Leu Glu Arg Ser Ala Ile
```

```
                    1280                1285                1290

Ala Arg Glu His Met Gly Gln Leu Leu His Gln Leu Leu Cys Ala
    1295                1300                1305

Gly His Leu Ser Thr Ala Gln Tyr Tyr Gln Gly Leu Tyr Glu Ile
    1310                1315                1320

Leu Glu Leu Ala Glu Asp Met Glu Ile Asp Ile Pro His Val Trp
    1325                1330                1335

Leu Tyr Leu Ala Glu Leu Val Thr Pro Ile Leu Gln Gly Gly
    1340                1345                1350

Val Pro Met Gly Glu Leu Phe Arg Glu Ile Thr Lys Pro Leu Arg
    1355                1360                1365

Pro Leu Gly Lys Ala Ala Ser Leu Leu Leu Glu Ile Leu Gly Leu
    1370                1375                1380

Leu Cys Lys Ser Met Gly Pro Lys Lys Val Gly Thr Leu Trp Arg
    1385                1390                1395

Glu Ala Gly Leu Ser Trp Lys Glu Phe Leu Pro Glu Gly Gln Asp
    1400                1405                1410

Ile Gly Ala Phe Val Ala Glu Gln Lys Val Glu Tyr Thr Leu Gly
    1415                1420                1425

Glu Glu Ser Glu Ala Pro Gly Gln Arg Ala Leu Pro Ser Glu Glu
    1430                1435                1440

Leu Asn Arg Gln Leu Glu Lys Leu Leu Lys Glu Gly Ser Ser Asn
    1445                1450                1455

Gln Arg Val Phe Asp Trp Ile Glu Ala Asn Leu Ser Glu Gln Gln
    1460                1465                1470

Ile Val Ser Asn Thr Leu Val Arg Ala Leu Met Thr Ala Val Cys
    1475                1480                1485

Tyr Ser Ala Ile Ile Phe Glu Thr Pro Leu Arg Val Asp Val Ala
    1490                1495                1500

Val Leu Lys Ala Arg Ala Lys Leu Leu Gln Lys Tyr Leu Cys Asp
    1505                1510                1515

Glu Gln Lys Glu Leu Gln Ala Leu Tyr Ala Leu Gln Ala Leu Val
    1520                1525                1530

Val Thr Leu Glu Gln Pro Pro Asn Leu Leu Arg Met Phe Phe Asp
    1535                1540                1545

Ala Leu Tyr Asp Glu Asp Val Val Lys Glu Asp Ala Phe Tyr Ser
    1550                1555                1560

Trp Glu Ser Ser Lys Asp Pro Ala Glu Gln Gln Gly Lys Gly Val
    1565                1570                1575

Ala Leu Lys Ser Val Thr Ala Phe Phe Lys Trp Leu Arg Glu Ala
    1580                1585                1590

Glu Glu Glu Ser Asp His Asn
    1595                1600

<210> SEQ ID NO 47
<211> LENGTH: 25
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
```

<221> NAME/KEY: misc_feature
<222> LOCATION: (21)..(22)
<223> OTHER INFORMATION: Xaa can be any naturally occurring amino acid

<400> SEQUENCE: 47

Asp Ile Ser Gly Leu Thr Pro Xaa Lys Glu Ser Lys Gln Phe Ala Lys
1               5                   10                  15

Xaa Glu Lys Gln Xaa Xaa Lys Lys Leu
            20                  25

<210> SEQ ID NO 48
<211> LENGTH: 2201
<212> TYPE: PRT
<213> ORGANISM: Homo sapiens

<400> SEQUENCE: 48

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Glu Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

-continued

```
Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Val Asp Cys Ser Glu Lys Arg Cys Pro Ala Asp Cys His Asn Arg
    370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
    450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
        515                 520                 525

Glu Leu Ser Cys Pro Asn Asp Cys His Gly Gln Gly Arg Cys Val Asn
    530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
    610                 615                 620

Pro Pro Lys Asp Leu Val Val Thr Glu Val Thr Glu Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
        675                 680                 685

Phe Ile Arg Val Phe Ala Ile Leu Glu Asn Lys Lys Ser Ile Pro Val
    690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735
```

-continued

```
Ile Ala Phe Glu Thr Trp Glu Ile Ile Phe Arg Asn Met Asn Lys Glu
                740                 745                 750

Asp Glu Gly Glu Ile Thr Lys Ser Leu Arg Arg Pro Glu Thr Ser Tyr
            755                 760                 765

Arg Gln Thr Gly Leu Ala Pro Gly Gln Glu Tyr Glu Ile Ser Leu His
        770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
        850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
        915                 920                 925

Pro Ile Ser Gly Gly Asp His Ala Glu Val Asp Val Pro Lys Ser Gln
        930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser Leu Thr Leu Leu Trp Lys Thr Pro
        995                 1000                1005

Leu Ala Lys Phe Asp Arg Tyr Arg Leu Asn Tyr Ser Leu Pro Thr
        1010                1015                1020

Gly Gln Trp Val Gly Val Gln Leu Pro Arg Asn Thr Thr Ser Tyr
    1025                1030                1035

Val Leu Arg Gly Leu Glu Pro Gly Gln Glu Tyr Asn Val Leu Leu
    1040                1045                1050

Thr Ala Glu Lys Gly Arg His Lys Ser Lys Pro Ala Arg Val Lys
    1055                1060                1065

Ala Ser Thr Glu Gln Ala Pro Glu Leu Glu Asn Leu Thr Val Thr
    1070                1075                1080

Glu Val Gly Trp Asp Gly Leu Arg Leu Asn Trp Thr Ala Ala Asp
    1085                1090                1095

Gln Ala Tyr Glu His Phe Ile Ile Gln Val Gln Glu Ala Asn Lys
    1100                1105                1110

Val Glu Ala Ala Arg Asn Leu Thr Val Pro Gly Ser Leu Arg Ala
    1115                1120                1125

Val Asp Ile Pro Gly Leu Lys Ala Ala Thr Pro Tyr Thr Val Ser
    1130                1135                1140

Ile Tyr Gly Val Ile Gln Gly Tyr Arg Thr Pro Val Leu Ser Ala
```

-continued

|  | 1145 |  |  |  | 1150 |  |  |  | 1155 |  |  |
|---|---|---|---|---|---|---|---|---|---|---|---|

Glu Ala Ser Thr Gly Glu Thr Pro Asn Leu Gly Glu Val Val Val
1160              1165              1170

Ala Glu Val Gly Trp Asp Ala Leu Lys Leu Asn Trp Thr Ala Pro
1175              1180              1185

Glu Gly Ala Tyr Glu Tyr Phe Phe Ile Gln Val Gln Glu Ala Asp
1190              1195              1200

Thr Val Glu Ala Ala Gln Asn Leu Thr Val Pro Gly Gly Leu Arg
1205              1210              1215

Ser Thr Asp Leu Pro Gly Leu Lys Ala Ala Thr His Tyr Thr Ile
1220              1225              1230

Thr Ile Arg Gly Val Thr Gln Asp Phe Ser Thr Thr Pro Leu Ser
1235              1240              1245

Val Glu Val Leu Thr Glu Glu Val Pro Asp Met Gly Asn Leu Thr
1250              1255              1260

Val Thr Glu Val Ser Trp Asp Ala Leu Arg Leu Asn Trp Thr Thr
1265              1270              1275

Pro Asp Gly Thr Tyr Asp Gln Phe Thr Ile Gln Val Gln Glu Ala
1280              1285              1290

Asp Gln Val Glu Glu Ala His Asn Leu Thr Val Pro Gly Ser Leu
1295              1300              1305

Arg Ser Met Glu Ile Pro Gly Leu Arg Ala Gly Thr Pro Tyr Thr
1310              1315              1320

Val Thr Leu His Gly Glu Val Arg Gly His Ser Thr Arg Pro Leu
1325              1330              1335

Ala Val Glu Val Val Thr Glu Asp Leu Pro Gln Leu Gly Asp Leu
1340              1345              1350

Ala Val Ser Glu Val Gly Trp Asp Gly Leu Arg Leu Asn Trp Thr
1355              1360              1365

Ala Ala Asp Asn Ala Tyr Glu His Phe Val Ile Gln Val Gln Glu
1370              1375              1380

Val Asn Lys Val Glu Ala Ala Gln Asn Leu Thr Leu Pro Gly Ser
1385              1390              1395

Leu Arg Ala Val Asp Ile Pro Gly Leu Glu Ala Ala Thr Pro Tyr
1400              1405              1410

Arg Val Ser Ile Tyr Gly Val Ile Arg Gly Tyr Arg Thr Pro Val
1415              1420              1425

Leu Ser Ala Glu Ala Ser Thr Ala Lys Glu Pro Glu Ile Gly Asn
1430              1435              1440

Leu Asn Val Ser Asp Ile Thr Pro Glu Ser Phe Asn Leu Ser Trp
1445              1450              1455

Met Ala Thr Asp Gly Ile Phe Glu Thr Phe Thr Ile Glu Ile Ile
1460              1465              1470

Asp Ser Asn Arg Leu Leu Glu Thr Val Glu Tyr Asn Ile Ser Gly
1475              1480              1485

Ala Glu Arg Thr Ala His Ile Ser Gly Leu Pro Pro Ser Thr Asp
1490              1495              1500

Phe Ile Val Tyr Leu Ser Gly Leu Ala Pro Ser Ile Arg Thr Lys
1505              1510              1515

Thr Ile Ser Ala Thr Ala Thr Glu Ala Leu Pro Leu Leu Glu
1520              1525              1530

Asn Leu Thr Ile Ser Asp Ile Asn Pro Tyr Gly Phe Thr Val Ser
1535              1540              1545

-continued

```
Trp Met Ala Ser Glu Asn Ala Phe Asp Ser Phe Leu Val Thr Val
    1550            1555                1560

Val Asp Ser Gly Lys Leu Leu Asp Pro Gln Glu Phe Thr Leu Ser
1565            1570                1575

Gly Thr Gln Arg Lys Leu Glu Leu Arg Gly Leu Ile Thr Gly Ile
    1580            1585                1590

Gly Tyr Glu Val Met Val Ser Gly Phe Thr Gln Gly His Gln Thr
1595            1600                1605

Lys Pro Leu Arg Ala Glu Ile Val Thr Glu Ala Glu Pro Glu Val
    1610            1615                1620

Asp Asn Leu Leu Val Ser Asp Ala Thr Pro Asp Gly Phe Arg Leu
1625            1630                1635

Ser Trp Thr Ala Asp Glu Gly Val Phe Asp Asn Phe Val Leu Lys
    1640            1645                1650

Ile Arg Asp Thr Lys Lys Gln Ser Glu Pro Leu Glu Ile Thr Leu
1655            1660                1665

Leu Ala Pro Glu Arg Thr Arg Asp Ile Thr Gly Leu Arg Glu Ala
    1670            1675                1680

Thr Glu Tyr Glu Ile Glu Leu Tyr Gly Ile Ser Lys Gly Arg Arg
1685            1690                1695

Ser Gln Thr Val Ser Ala Ile Ala Thr Thr Ala Met Gly Ser Pro
    1700            1705                1710

Lys Glu Val Ile Phe Ser Asp Ile Thr Glu Asn Ser Ala Thr Val
1715            1720                1725

Ser Trp Arg Ala Pro Thr Ala Gln Val Glu Ser Phe Arg Ile Thr
    1730            1735                1740

Tyr Val Pro Ile Thr Gly Gly Thr Pro Ser Met Val Thr Val Asp
1745            1750                1755

Gly Thr Lys Thr Gln Thr Arg Leu Val Lys Leu Ile Pro Gly Val
    1760            1765                1770

Glu Tyr Leu Val Ser Ile Ile Ala Met Lys Gly Phe Glu Glu Ser
1775            1780                1785

Glu Pro Val Ser Gly Ser Phe Thr Thr Ala Leu Asp Gly Pro Ser
    1790            1795                1800

Gly Leu Val Thr Ala Asn Ile Thr Asp Ser Glu Ala Leu Ala Arg
1805            1810                1815

Trp Gln Pro Ala Ile Ala Thr Val Asp Ser Tyr Val Ile Ser Tyr
    1820            1825                1830

Thr Gly Glu Lys Val Pro Glu Ile Thr Arg Thr Val Ser Gly Asn
1835            1840                1845

Thr Val Glu Tyr Ala Leu Thr Asp Leu Glu Pro Ala Thr Glu Tyr
    1850            1855                1860

Thr Leu Arg Ile Phe Ala Glu Lys Gly Pro Gln Lys Ser Ser Thr
1865            1870                1875

Ile Thr Ala Lys Phe Thr Thr Asp Leu Asp Ser Pro Arg Asp Leu
    1880            1885                1890

Thr Ala Thr Glu Val Gln Ser Glu Thr Ala Leu Leu Thr Trp Arg
1895            1900                1905

Pro Pro Arg Ala Ser Val Thr Gly Tyr Leu Leu Val Tyr Glu Ser
    1910            1915                1920

Val Asp Gly Thr Val Lys Glu Val Ile Val Gly Pro Asp Thr Thr
1925            1930                1935
```

```
Ser Tyr Ser Leu Ala Asp Leu Ser Pro Ser Thr His Tyr Thr Ala
    1940                1945                1950

Lys Ile Gln Ala Leu Asn Gly Pro Leu Arg Ser Asn Met Ile Gln
    1955                1960                1965

Thr Ile Phe Thr Thr Ile Gly Leu Leu Tyr Pro Phe Pro Lys Asp
    1970                1975                1980

Cys Ser Gln Ala Met Leu Asn Gly Asp Thr Thr Ser Gly Leu Tyr
    1985                1990                1995

Thr Ile Tyr Leu Asn Gly Asp Lys Ala Glu Ala Leu Glu Val Phe
    2000                2005                2010

Cys Asp Met Thr Ser Asp Gly Gly Trp Ile Val Phe Leu Arg
    2015                2020                2025

Arg Lys Asn Gly Arg Glu Asn Phe Tyr Gln Asn Trp Lys Ala Tyr
    2030                2035                2040

Ala Ala Gly Phe Gly Asp Arg Arg Glu Glu Phe Trp Leu Gly Leu
    2045                2050                2055

Asp Asn Leu Asn Lys Ile Thr Ala Gln Gly Gln Tyr Glu Leu Arg
    2060                2065                2070

Val Asp Leu Arg Asp His Gly Glu Thr Ala Phe Ala Val Tyr Asp
    2075                2080                2085

Lys Phe Ser Val Gly Asp Ala Lys Thr Arg Tyr Lys Leu Lys Val
    2090                2095                2100

Glu Gly Tyr Ser Gly Thr Ala Gly Asp Ser Met Ala Tyr His Asn
    2105                2110                2115

Gly Arg Ser Phe Ser Thr Phe Asp Lys Asp Thr Asp Ser Ala Ile
    2120                2125                2130

Thr Asn Cys Ala Leu Ser Tyr Lys Gly Ala Phe Trp Tyr Arg Asn
    2135                2140                2145

Cys His Arg Val Asn Leu Met Gly Arg Tyr Gly Asp Asn Asn His
    2150                2155                2160

Ser Gln Gly Val Asn Trp Phe His Trp Lys Gly His Glu His Ser
    2165                2170                2175

Ile Gln Phe Ala Glu Met Lys Leu Arg Pro Ser Asn Phe Arg Asn
    2180                2185                2190

Leu Glu Gly Arg Arg Lys Arg Ala
    2195                2200

<210> SEQ ID NO 49
<211> LENGTH: 531
<212> TYPE: PRT
<213> ORGANISM: Homo sapiens

<400> SEQUENCE: 49

Met Asp Gly Ile Val Pro Asp Ile Ala Val Gly Thr Lys Arg Gly Ser
1               5                   10                  15

Asp Glu Leu Phe Ser Thr Cys Val Thr Asn Gly Pro Phe Ile Met Ser
            20                  25                  30

Ser Asn Ser Ala Ser Ala Ala Asn Gly Asn Asp Ser Lys Lys Phe Lys
        35                  40                  45

Gly Asp Ser Arg Ser Ala Gly Val Pro Ser Arg Val Ile His Ile Arg
    50                  55                  60

Lys Leu Pro Ile Asp Val Thr Glu Gly Glu Val Ile Ser Leu Gly Leu
65                  70                  75                  80

Pro Phe Gly Lys Val Thr Asn Leu Leu Met Leu Lys Gly Lys Asn Gln
                85                  90                  95
```

-continued

```
Ala Phe Ile Glu Met Asn Thr Glu Glu Ala Asn Thr Met Val Asn
            100                 105                 110

Tyr Tyr Thr Ser Val Thr Pro Val Leu Arg Gly Gln Pro Ile Tyr Ile
            115                 120                 125

Gln Phe Ser Asn His Lys Glu Leu Lys Thr Asp Ser Ser Pro Asn Gln
        130                 135                 140

Ala Arg Ala Gln Ala Ala Leu Gln Ala Val Asn Ser Val Gln Ser Gly
145                 150                 155                 160

Asn Leu Ala Leu Ala Ala Ser Ala Ala Val Asp Ala Gly Met Ala
                165                 170                 175

Met Ala Gly Gln Ser Pro Val Leu Arg Ile Ile Val Glu Asn Leu Phe
            180                 185                 190

Tyr Pro Val Thr Leu Asp Val Leu His Gln Ile Phe Ser Lys Phe Gly
            195                 200                 205

Thr Val Leu Lys Ile Ile Thr Phe Thr Lys Asn Asn Gln Phe Gln Ala
        210                 215                 220

Leu Leu Gln Tyr Ala Asp Pro Val Ser Ala Gln His Ala Lys Leu Ser
225                 230                 235                 240

Leu Asp Gly Gln Asn Ile Tyr Asn Ala Cys Cys Thr Leu Arg Ile Asp
                245                 250                 255

Phe Ser Lys Leu Thr Ser Leu Asn Val Lys Tyr Asn Asn Asp Lys Ser
            260                 265                 270

Arg Asp Tyr Thr Arg Pro Asp Leu Pro Ser Gly Asp Ser Gln Pro Ser
            275                 280                 285

Leu Asp Gln Thr Met Ala Ala Ala Phe Gly Leu Ser Val Pro Asn Val
        290                 295                 300

His Gly Ala Leu Ala Pro Leu Ala Ile Pro Ser Ala Ala Ala Ala
305                 310                 315                 320

Ala Ala Ala Gly Arg Ile Ala Ile Pro Gly Leu Ala Gly Ala Gly Asn
                325                 330                 335

Ser Val Leu Leu Val Ser Asn Leu Asn Pro Glu Arg Val Thr Pro Gln
            340                 345                 350

Ser Leu Phe Ile Leu Phe Gly Val Tyr Gly Asp Val Gln Arg Val Lys
        355                 360                 365

Ile Leu Phe Asn Lys Lys Glu Asn Ala Leu Val Gln Met Ala Asp Gly
        370                 375                 380

Asn Gln Ala Gln Leu Ala Met Ser His Leu Asn Gly His Lys Leu His
385                 390                 395                 400

Gly Lys Pro Ile Arg Ile Thr Leu Ser Lys His Gln Asn Val Gln Leu
                405                 410                 415

Pro Arg Glu Gly Gln Glu Asp Gln Gly Leu Thr Lys Asp Tyr Gly Asn
            420                 425                 430

Ser Pro Leu His Arg Phe Lys Lys Pro Gly Ser Lys Asn Phe Gln Asn
        435                 440                 445

Ile Phe Pro Pro Ser Ala Thr Leu His Leu Ser Asn Ile Pro Pro Ser
        450                 455                 460

Val Ser Glu Glu Asp Leu Lys Val Leu Phe Ser Ser Asn Gly Gly Val
465                 470                 475                 480

Val Lys Gly Phe Lys Phe Phe Gln Lys Asp Arg Lys Met Ala Leu Ile
                485                 490                 495

Gln Met Gly Ser Val Glu Glu Ala Val Gln Ala Leu Ile Asp Leu His
            500                 505                 510
```

-continued

Asn His Asp Leu Gly Glu Asn His His Leu Arg Val Ser Phe Ser Lys
            515                 520                 525

Ser Thr Ile
    530

<210> SEQ ID NO 50
<211> LENGTH: 317
<212> TYPE: PRT
<213> ORGANISM: Homo sapiens

<400> SEQUENCE: 50

Met Arg Leu Gly Pro Arg Thr Ala Ala Leu Gly Leu Leu Leu Leu Cys
1               5                   10                  15

Ala Ala Ala Gly Ala Gly Lys Ala Glu Glu Leu His Tyr Pro Leu
            20                  25                  30

Gly Glu Arg Arg Ser Asp Tyr Asp Arg Glu Ala Leu Leu Gly Val Gln
            35                  40                  45

Glu Asp Val Asp Glu Tyr Val Lys Leu Gly His Glu Glu Gln Gln Lys
50                  55                  60

Arg Leu Gln Ala Ile Ile Lys Lys Ile Asp Leu Asp Ser Asp Gly Phe
65                  70                  75                  80

Leu Thr Glu Ser Glu Leu Ser Ser Trp Ile Gln Met Ser Phe Lys His
                85                  90                  95

Tyr Ala Met Gln Glu Ala Lys Gln Gln Phe Val Glu Tyr Asp Lys Asn
            100                 105                 110

Ser Asp Asp Thr Val Thr Trp Asp Glu Tyr Asn Ile Gln Met Tyr Asp
            115                 120                 125

Arg Val Ile Asp Phe Asp Glu Asn Thr Ala Leu Asp Asp Ala Glu Glu
130                 135                 140

Glu Ser Phe Arg Lys Leu His Leu Lys Asp Lys Lys Arg Phe Glu Lys
145                 150                 155                 160

Ala Asn Gln Asp Ser Gly Pro Gly Leu Ser Leu Glu Glu Phe Ile Ala
                165                 170                 175

Phe Glu His Pro Glu Glu Val Asp Tyr Met Thr Glu Phe Val Ile Gln
            180                 185                 190

Glu Ala Leu Glu Glu His Asp Lys Asn Gly Asp Gly Phe Val Ser Leu
            195                 200                 205

Glu Glu Phe Leu Gly Asp Tyr Arg Trp Asp Pro Thr Ala Asn Glu Asp
210                 215                 220

Pro Glu Trp Ile Leu Val Glu Lys Asp Arg Phe Val Asn Asp Tyr Asp
225                 230                 235                 240

Lys Asp Asn Asp Gly Arg Leu Asp Pro Gln Glu Leu Leu Pro Trp Val
                245                 250                 255

Val Pro Asn Asn Gln Gly Ile Ala Gln Glu Glu Ala Leu His Leu Ile
            260                 265                 270

Asp Glu Met Asp Leu Asn Gly Asp Lys Lys Leu Ser Glu Glu Glu Ile
            275                 280                 285

Leu Glu Asn Pro Asp Leu Phe Leu Thr Ser Glu Ala Thr Asp Tyr Gly
            290                 295                 300

Arg Gln Leu His Asp Asp Tyr Phe Tyr His Asp Glu Leu
305                 310                 315

<210> SEQ ID NO 51
<211> LENGTH: 326
<212> TYPE: PRT
<213> ORGANISM: Homo sapiens

```
<400> SEQUENCE: 51

Met Ser Asn Gly Tyr Glu Asp His Met Ala Glu Asp Cys Arg Gly Asp
1               5                   10                  15

Ile Gly Arg Thr Asn Leu Ile Val Asn Tyr Leu Pro Gln Asn Met Thr
            20                  25                  30

Gln Asp Glu Leu Arg Ser Leu Phe Ser Ser Ile Gly Glu Val Glu Ser
        35                  40                  45

Ala Lys Leu Ile Arg Asp Lys Val Ala Gly His Ser Leu Gly Tyr Gly
    50                  55                  60

Phe Val Asn Tyr Val Thr Ala Lys Asp Ala Glu Arg Ala Ile Asn Thr
65                  70                  75                  80

Leu Asn Gly Leu Arg Leu Gln Ser Lys Thr Ile Lys Val Ser Tyr Ala
                85                  90                  95

Arg Pro Ser Ser Glu Val Ile Lys Asp Ala Asn Leu Tyr Ile Ser Gly
            100                 105                 110

Leu Pro Arg Thr Met Thr Gln Lys Asp Val Glu Asp Met Phe Ser Arg
        115                 120                 125

Phe Gly Arg Ile Ile Asn Ser Arg Val Leu Val Asp Gln Thr Thr Gly
    130                 135                 140

Leu Ser Arg Gly Val Ala Phe Ile Arg Phe Asp Lys Arg Ser Glu Ala
145                 150                 155                 160

Glu Glu Ala Ile Thr Ser Phe Asn Gly His Lys Pro Pro Gly Ser Ser
                165                 170                 175

Glu Pro Ile Ala Val Lys Phe Ala Ala Asn Pro Asn Gln Asn Lys Asn
            180                 185                 190

Val Ala Leu Leu Ser Gln Leu Tyr His Ser Pro Ala Arg Arg Phe Gly
        195                 200                 205

Gly Pro Val His His Gln Ala Gln Arg Phe Arg Phe Ser Pro Met Gly
    210                 215                 220

Val Asp His Met Ser Gly Leu Ser Gly Val Asn Val Pro Gly Asn Ala
225                 230                 235                 240

Ser Ser Gly Trp Cys Ile Phe Ile Tyr Asn Leu Gly Gln Asp Ala Asp
                245                 250                 255

Glu Gly Ile Leu Trp Gln Met Phe Gly Pro Phe Gly Ala Val Thr Asn
            260                 265                 270

Val Lys Val Ile Arg Asp Phe Asn Thr Asn Lys Cys Lys Gly Phe Gly
        275                 280                 285

Phe Val Thr Met Thr Asn Tyr Glu Glu Ala Ala Met Ala Ile Ala Ser
    290                 295                 300

Leu Asn Gly Tyr Arg Leu Gly Asp Lys Ile Leu Gln Val Ser Phe Lys
305                 310                 315                 320

Thr Asn Lys Ser His Lys
                325

<210> SEQ ID NO 52
<211> LENGTH: 25
<212> TYPE: DNA
<213> ORGANISM: Artificial Sequence
<220> FEATURE:
<223> OTHER INFORMATION: Primer 3PEI

<400> SEQUENCE: 52
ccgcgaattc tcatctcagg gtgag                                          25
```

```
-continued

<210> SEQ ID NO 53
<211> LENGTH: 8
<212> TYPE: PRT
<213> ORGANISM: Artificial Sequence
<220> FEATURE:
<223> OTHER INFORMATION: FLAG epitope

<400> SEQUENCE: 53

Asp Tyr Lys Asp Asp Asp Asp Lys
1               5

<210> SEQ ID NO 54
<211> LENGTH: 10
<212> TYPE: PRT
<213> ORGANISM: Homo sapiens

<400> SEQUENCE: 54

Gln Gly Leu Ile Ser Arg Gly Tyr Ser Tyr
1               5                   10

<210> SEQ ID NO 55
<211> LENGTH: 11
<212> TYPE: PRT
<213> ORGANISM: Homo sapiens

<400> SEQUENCE: 55

Ala Val Arg Asp Ile Ser Glu Ala Ser Val Phe
1               5                   10
```